US011945798B2

(12) United States Patent
Lee et al.

(10) Patent No.: US 11,945,798 B2
(45) Date of Patent: Apr. 2, 2024

(54) SUBSTITUTED AMINOPYRIDINE COMPOUNDS AS EGFR INHIBITORS

(71) Applicants: YUHAN CORPORATION, Seoul (KR); JANSSEN BIOTECH, INC., Horsham, PA (US)

(72) Inventors: Hyunjoo Lee, Suwon-si (KR); Su Bin Choi, Hwaseong-si (KR); Young Ae Yoon, Seongnam-si (KR); Kwan Hoon Hyun, Incheon (KR); Jae Young Sim, Yongin-si (KR); Marian C. Bryan, Spring House, PA (US); Scott Kuduk, Spring House, PA (US); James Campbell Robertson, Spring House, PA (US); Jaekyoo Lee, North Andover, MA (US); Paresh Devidas Salgaonkar, Lexington, MA (US); Byung-Chul Suh, Lexington, MA (US); Jong Sung Koh, Cambridge, MA (US); So Young Hwang, Lexington, MA (US)

(73) Assignees: YUHAN CORPORATION, Seoul (KR); JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 17/822,438

(22) Filed: Aug. 26, 2022

(65) Prior Publication Data
US 2023/0086795 A1    Mar. 23, 2023

Related U.S. Application Data

(60) Provisional application No. 63/237,653, filed on Aug. 27, 2021.

(51) Int. Cl.
*C07D 401/14*    (2006.01)
*C07D 413/14*    (2006.01)
(52) U.S. Cl.
CPC ......... *C07D 401/14* (2013.01); *C07D 413/14* (2013.01)
(58) Field of Classification Search
CPC .............................. A61P 35/00; C07D 401/14
See application file for complete search history.

(56) References Cited

U.S. PATENT DOCUMENTS

| | | |
|---|---|---|
| 6,884,804 B2 | 4/2005 | Choon-Moon |
| 7,560,464 B2 | 7/2009 | Wang et al. |
| 7,642,354 B2 | 1/2010 | Wang et al. |
| 8,058,045 B2 | 11/2011 | Collins et al. |
| 8,367,658 B2 | 2/2013 | Collins et al. |
| 9,242,984 B2 | 1/2016 | Machacek et al. |
| 9,868,720 B2 | 1/2018 | Cohen et al. |
| 10,822,327 B2 | 11/2020 | Liu et al. |
| 2003/0144309 A1 | 7/2003 | Choon-Moon |
| 2004/0236084 A1 | 11/2004 | Biwersi et al. |
| 2005/0239800 A1 | 10/2005 | Wang et al. |
| 2005/0267089 A1 | 12/2005 | Wang et al. |
| 2008/0108600 A1 | 5/2008 | Wang et al. |
| 2010/0311730 A1 | 12/2010 | Collins et al. |
| 2012/0040967 A1 | 2/2012 | Collins et al. |
| 2015/0191461 A1* | 7/2015 | Machacek ............ C07D 403/14 544/122 |
| 2016/0046608 A1 | 2/2016 | Cohen et al. |
| 2019/0375727 A1 | 12/2019 | Liu et al. |
| 2020/0392156 A1 | 12/2020 | Kesicki |
| 2021/0317136 A1 | 10/2021 | Lindstrom et al. |
| 2022/0177459 A1 | 6/2022 | Du et al. |
| 2022/0298140 A1 | 9/2022 | Chen |
| 2022/0411407 A1 | 12/2022 | Wang et al. |

FOREIGN PATENT DOCUMENTS

| | | | |
|---|---|---|---|
| CN | 104761585 A | 7/2015 | |
| KR | 10-2020-0016567 A | 2/2020 | |
| WO | 2019/222538 A1 | 11/2019 | |
| WO | WO-2021159993 A1 * | 8/2021 | ........... A61K 31/444 |

OTHER PUBLICATIONS

Hanan et al., "Discovery of Selective and Noncovalent Diaminopyrimidine-Based Inhibitors of Epidermal Growth Factor Receptor Containing the T790M Resistance Mutation", J. Med. Chem., 2014, vol. 57, pp. 10176-10191.

* cited by examiner

Primary Examiner — Jeffrey S Lundgren
Assistant Examiner — Eric Tran
(74) Attorney, Agent, or Firm — Vorys, Sater, Seymour and Pease LLP; Mih Suhn Koh

(57) ABSTRACT

Provided are aminopyridine compounds and pharmaceutically acceptable compositions thereof which exhibit inhibition activity against certain mutated forms of EGFR.

39 Claims, No Drawings

SUBSTITUTED AMINOPYRIDINE COMPOUNDS AS EGFR INHIBITORS

FIELD OF THE INVENTION

The present invention relates to novel aminopyridine compounds and pharmaceutically acceptable compositions thereof which exhibit inhibition activity against certain mutated forms of EGFR.

BACKGROUND

A distinct subtype of lung cancer is epidermal growth factor receptor (EGFR) mutation positive non-small cell lung cancer (NSCLC). The human EGFR is a membrane-bound receptor tyrosine kinase of the ErbB family. The activation causes downstream effects via several signaling pathways including the RAS/RAF/MEK/ERK/MAPK and PI3K/PTEN/Akt/mTOR (Chen et al., 2020). The EGFR signaling pathway regulate a series of important events including proliferation, migration, differentiation, apoptosis, as well as those that regulate intercellular communication during development (Wee et al., 2017; Huang et al., 2015; Yewale et al., 2013).

Approximately 10% to 50% of NSCLC patients have EGFR activating mutations, such as in-frame deletions in exon 19 deletion (Del19) or a missense mutation in exon 21 (L858R). (Yang et al., 2018; Shigematsu et al., 2005; Shu et al., 2017; Zhang et al., 2010). These patients respond well to first and second-generation EGFR tyrosine kinase inhibitors (TKI), including gefitinib (IRESSA™), erlotinib (TARCEVA™), and afatinib (GIOTRIF™) allowing them as the initial therapy for in patients with advanced NSCLC harboring common EGFR mutations (Kashima et al., 2020; Mok et al., 2009; Zhou et al., 2011; Sequist et al., 2013). But ultimately acquired resistance to therapy with gefitinib or erlotinib arises predominantly by mutation of the gatekeeper residue T790M, which is detected in approximately half of clinically resistant patients, resulting in double mutants, L858R/T790M and Del19/T790M.

Several third-generation EGFR TKIs were being explored to overcome this resistance. Currently, osimertinib is the third-generation EGFR-TKI approved by major regulatory agencies for treatment of T790M-positive patients who have progressed on first- or second generation EGFR-TKIs (Leonetti et al., 2019; Soria et al., 2018).

Osimertinib is a powerful inhibitor that inhibits EGFR mutations and T790M resistant mutations, but it causes ineffective binding and C797S subsequent resistance in NSCLC patients (Arulananda et al., 2017). Unfortunately, it has been reported that acquired resistance mutations occur in lung cancer patients after the treatment with third-generation EGFR-TKIs. The C797S mutation is the frequently arise after the use of third generation EGFR TKIs in 10% to 30% of these patients. (Ramalingam et al., 2018; Thress et al., 2015; Oxnard et al., 2018; Starrett et al., 2020; Mehlman et al., 2019; Rangachari et al., 2019; Zhou et al., 2019). Osimertinib resistance resulting from EGFR triple mutations (Del19/T790M/C797S and L858R/T790M/C797S) has been reported, requiring the next generation EGFR-TKI to overcome the osimertinib resistant EGFR triple mutations (Kashima et al., 2020).

In front-line therapy with third generation TKI, C797S develops in the absence of T790M (Chen et al., 2020). Osimertinib was also approved in 2018 as first-line therapy for locally advanced or metastatic EGFR-mutated NSCLC, regardless of T790M mutation status (Leonetti et al., 2019). When osimertinib was administered as a front-line therapy, the frequency of the C797S mutation was 7%, making it the second most frequent mechanism, behind MET amplification, of drug resistance in this setting (Leonetti et al., 2019; Ramalingam et al., 2018).

When osimertinib was administered as a front-line therapy, the most common resistance mechanisms resulted to be the C797S mutation (7%) and MET amplification (15%). Other mechanisms included HER2 amplification, PIK3CA and RAS mutations (Ramalingam et al., 2018). Also, selectivity to wild-type (WT) EGFR is important for EGFR-TKIs, because WT EGFR inhibition causes adverse effects such as rashes and/or diarrhea, and these WT EGFR-derived toxicities cause dose-limiting effects (Kashima et al., 2020; Fakih et al., 2010; Takeda et al., 2015).

The next generation EGFR compounds would need to inhibit Del19/T790M/C797S, L858R/T790M/C797S, Del19/C797S and L858R/C797S and be highly selective versus WT EGFR to avoid adverse effects. Recently, mutant selective inhibitors, BI-4020 and BLU-945 were reported as potential therapeutic strategies to overcome the EGFR Del19/T790M/C797S mutations (Engelhardt et al., 2019; Schalm et al., 2020).

However, there have been no reports of these compounds inhibiting Del19/C797S and L858R/C797S. Therefore, novel EGFR-TKIs potently effective against EGFR triple/double mutations are urgently needed.

To address this unmet need, we are developing a next generation TKI targeting both C797S triple and double mutants. It is necessary to develop a novel selective (next generation) inhibitor for NSCLC patients with advanced or metastatic diseases carrying Del19/T790M/C797S, L858R/T790M/C797S, Del19/C797S and L858R/C797S mutation following second-line or upfront use of third-generation EGFR TKIs.

REFERENCES

Arulananda S, John T, Dobrovic A. et al. Combination Osimertinib and Gefitinib in C797S and T790M EGFR-Mutated Non-Small Cell Lung Cancer. Journal of Thoracic Oncology Vol. 12 No. 11: 1728-1732, 2017.

Chen J S, Riess J W. Advances in targeting acquired resistance mechanisms to epidermal growth factor receptor tyrosine kinase inhibitors. Justin A. Chen, Jonathan W. Riess. J Thorac Dis 2020; 12(5):2859-2876.

Engelhardt H, et al. Start Selective and Rigidify: The Discovery Path toward a Next Generation of EGFR Tyrosine Kinase Inhibitors. Cite This: J. Med. Chem. 2019, 62, 10272-10293.

Fakih M, Vincent M. Adverse events associated with anti-EGFR therapies for the treatment of metastatic colorectal cancer. Curr. Oncol. 2010; 17: S18-30.

Huang L, Fu L. Mechanisms of resistance to EGFR tyrosine kinase inhibitors. Acta Pharm Sin B 2015; 5:390-401.

Kashima K, et al. $CH_{7233163}$ Overcomes Osimertinib-Resistant EGFR-Del19/T790M/C797S Mutation. Mol Cancer Ther; 19(11) November 2020.

Leonetti A, et al. Resistance mechanisms to osimertinib in EGFR-mutated non-small cell lung cancer. British Journal of Cancer (2019) 121:725-737.

Mok T S, Wu Y L, Thongprasert S, Yang C H, Chu D T, Saijo N, et al. Gefitinib or carboplatin-paclitaxel in pulmonary adenocarcinoma. N Engl J Med 2009; 361: 947-57.

Mehlman C, Cadranel J, Rousseau-Bussac G, Lacave R, Pujals A, Girard N, et al. Resistance mechanisms to osimertinib in EGFR-mutated advanced non-small cell lung cancer: A multicentric retrospective French study. Lung Cancer 2019; 137:149-56.

Oxnard G R, Hu Y, Mileham K F, Husain H, Costa D B, Tracy P, et al. Assessment of resistance mechanisms and clinical implications in patients with EGFR T790M-positive lung cancer and acquired resistance to osimertinib. JAMA Oncol. 2018; 4:1527-34.

Ramalingam S S, Yang J C, Lee C K, Kurata T, Kim D W, John T, et al. Osimertinib as first-line treatment of EGFR mutation-positive advanced non-small-cell lung cancer. J. Clin. Oncol. 2018; 36:841-9.

Rangachari D, To C, Shpilsky J E, VanderLaan P A, Kobayashi S S, Mushajiang M, et al. EGFR-mutated lung cancers resistant to osimertinib through EGFR C797S respond to first-generation reversible EGFR inhibitors but eventually acquire EGFR T790M/C797S in preclinical models and clinical samples. J. Thorac. Oncol. 2019; 14:1995-2002.

Schalm S, et al. BLU-945, a highly potent and selective 4th-generation EGFR TKI for the treatment of EGFR+/T790M/C797S resistant NSCLC. 2020, ESMO.

Sequist L V, Yang J C, Yamamoto N, O'Byme K, Hirsh V, Mok T, et al. Phase III study of afatinib or cisplatin plus pemetrexed in patients with metastatic lung adenocarcinoma with EGFR mutations. J. Clin. Oncol. 2013; 31:3327-34.

Shigematsu H, Lin L, Takahashi T, Nomura M, Suzuki M, Wistuba I I, et al. Clinical and biological features associated with epidermal growth factor receptor gene mutations in lung cancers. J Natl Cancer Inst 2005; 97:339-46.

Shu Y, WuX, Tong X, WangX, Chang Z, MaoY, et al. Circulating tumor DNA mutation profiling by targeted next generation sequencing provides guidance for personalized treatments in multiple cancer types. Sci Rep 2017; 7:583.

Soria, J.-C., Ohe, Y., Vansteenkiste, J., Reungwetwattana, T., Chewaskulyong, B., Lee, K. H. et al. Osimertinib in untreated EGFR-mutated advanced non-small cell lung cancer. N. Engl. J. Med 378, 113-125 (2018).

Starrett J H, Guernet A A, Cuomo M E, Poels K E, van Alderwerelt van Rosenburgh I K, Nagelberg A, et al. Drug sensitivity and allele-specificity of first-line osimertinib resistance EGFR mutations. Cancer Res 2020; 80:2017-30.

Takeda M, Okamoto I, Nakagawa K. Pooled safety analysis of EGFR-TKI treatment for EGFR mutation-positive non-small cell lung cancer. Lung Cancer 2015; 88:74-9.

Thress K S, Paweletz C P, Felip E, Cho B C, Stetson D, Dougherty B, et al. Acquired EGFR C797S mutation mediates resistance to AZD9291 in non-small cell lung cancer harboring EGFR T790M. Nat Med 2015; 21:560-2.

Wee, P.; Wang, Z. Epidermal Growth Factor Receptor Cell Proliferation Signaling Pathways. Cancers 2017, 9, 52.

Yewale C, Baradia D, Vhora I, et al. Epidermal growth factor receptor targeting in cancer: a review of trends and strategies. Biomaterials 2013; 34:8690-707.

Yang Z, Yang N, et al. Investigating Novel Resistance Mechanisms to Third-Generation EGFR Tyrosine Clin Cancer Res; 2018

Zhang Z, Stiegler A L, Boggon T J, Kobayashi S, Halmos B. EGFR-mutated lung cancer: a paradigm of molecular oncology. Oncotarget 2010; 1:497-514.

Zhou C, Wu Y L, Chen G, Feng J, Liu X Q, Wang C, et al. Erlotinib versus chemotherapy as first-line treatment for patients with advanced EGFR mutation-positive non-small-cell lung cancer (OPTIMAL, CTONG-0802): a multicentre, open-label, randomised, phase 3 study. Lancet Oncol. 2011; 12:735-42.

Zhou Z, Zhao Y, Shen S, Gu L, Niu X, Xu Y, et al. Durable clinical response of lung adenocarcinoma harboring EGFR 19Del/T790M/in trans-C797S to combination therapy of first- and third-generation EGFR tyrosine kinase inhibitors. J. Thorac. Oncol. 2019; 14:e157-e9.

SUMMARY OF INVENTION

The present invention relates to novel aminopyridine compounds of Formula (I) shown below, or a pharmaceutically acceptable salt thereof:

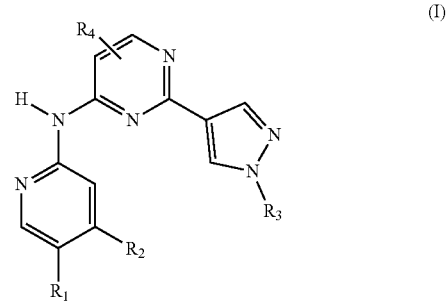

wherein $R_1$ is selected from the group consisting of halogen;

$C_{1-6}$alkyl optionally substituted by one or more substituents selected from the group consisting of OH, halogen, $C_{3-6}$cycloalkyl, —$NHC_{1-6}$alkyl, and $N(C_{1-6}alkyl)_2$;

$C_{1-3}$alkoxy;

—C(O)—$C_{1-6}$alkyl, optionally substituted by one or more substituents selected from the group consisting of halogen, —$NHC_{1-6}$alkyl, —$N(C_{1-6}alkyl)_2$, and 4-7 membered heterocyclyl;

—C(O)—$C_{3-6}$cycloalkyl, optionally substituted by one or more substituents selected from the group consisting of OH and halogen;

—C(O)—$C_{6-10}$ aryl optionally substituted by one or more halogens;

—C(O)-5-6 membered heteroaryl optionally substituted by one or more halogens;

—$N(C_{1-6}alkyl)_2$;

—$NHC(O)C_{1-6}$alkyl;

—$NHC(O)C_{3-6}$cycloalkyl, optionally substituted by one or more substituents selected from the group consisting of OH and halogen;

—$C(O)NHC_{1-6}$alkyl optionally substituted by one or more substituents selected from the group consisting of OH and halogen;

—$C(O)NHC_{3-6}$cycloalkyl optionally substituted by one or more substituents selected from the group consisting of OH, halogen and —$N(C_{1-6}alkyl)_2$;

—C(O)-3-7 membered heterocyclyl optionally substituted by one or more substituents selected from the group consisting of OH, halogen, $C_{1-6}$alkyl, and $C_{1-6}$hydroxyalkyl; and 4-7 membered heterocyclyl optionally substituted by one or more substituents selected from the group consisting of OH and halogen, $R_2$ is selected from the group consisting of —$XC_{1-6}$alkyl optionally substituted by one or more substituents selected from the group consisting of OH, halogen, and —N($C_{1-6}$alkyl)$_2$; and —X(CH$_2$)$_n$-A-(R$_{2A}$)$_o$, X is —NH—, —O—, bond or —C≡C—, n is an integer of 0 to 2, is an integer of 0 to 3, A is selected from the group consisting of $C_{3-8}$cycloalkyl; $C_{6-10}$ aryl; 4-11 membered heterocyclyl; and 5-6 membered heteroaryl, $R_{2A}$ is independently selected from the group consisting of

H;

halogen;

OH;

NH$_2$;

$C_{1-6}$alkyl optionally substituted by one or more substituents selected from the group consisting of OH, NH$_2$, halogen, $C_{3-6}$cycloalkyl, $C_{1-3}$alkoxy, —NHC$_{1-6}$alkyl, —NHC$_{1-6}$ hydroxyalkyl, —NHC$_{1-6}$haloalkyl, —NHC$_{3-6}$cycloalkyl, —N(C$_{1-6}$alkyl)$_2$, —N(C$_{1-6}$haloalkyl)$_2$, —NHC(O)C$_{1-6}$alkyl, —C(O)NHC$_{1-6}$alkyl, —C(O)N(C$_{1-6}$alkyl)$_2$, 3-7 membered heterocyclyl and 5-6 membered heteroaryl;

$C_{3-6}$cycloalkyl;

$C_{1-3}$alkoxy optionally substituted by one or more halogens;

—C(O)NHC$_{1-6}$alkyl optionally substituted by one or more substituents selected from the group consisting of OH and halogen;

—C(O)N(C$_{1-6}$alkyl)$_2$ optionally substituted by one or more substituents selected from the group consisting of OH and halogen;

—NHC$_{1-6}$alkyl optionally substituted by one or more substituents selected from the group consisting of OH, halogen, —NHC$_{1-6}$alkyl, —N(C$_{1-6}$alkyl)$_2$, and 3-7 membered heterocyclyl optionally substituted by halogen or —N(C$_{1-6}$alkyl)$_2$;

—N(C$_{1-6}$alkyl)$_2$ where C$_{1-6}$alkyl is optionally substituted by one or more halogens;

—NH-4-7 membered heterocyclyl optionally substituted by C$_{1-6}$alkyl; and 4-7 membered heterocyclyl, $R_3$ is selected from the group consisting of

H;

$C_{1-6}$alkyl optionally substituted by one or more substituents selected from the group consisting of halogen and $C_{3-6}$cycloalkyl; $C_{3-6}$cycloalkyl;

4-7 membered heterocyclyl;

—S(O)$_2$C$_{1-6}$alkyl optionally substituted by one or more halogens; and

—S(O)$_2$C$_{3-6}$cycloalkyl optionally substituted by one or more halogens, and $R_4$ is selected from the group consisting of H, halogen and $C_{1-6}$alkyl.

The present invention also relates to methods of treating protein kinase-mediated disease, particularly mutant EGFR-mediated disease in a subject in need thereof comprising administering to said subject a therapeutically effective amount of said compounds of Formula (I) or a pharmaceutically acceptable salt thereof.

The present invention also relates to pharmaceutically acceptable compositions comprising said compounds of Formula (I) or a pharmaceutically acceptable salt thereof, which exhibit inhibition activity against at least one mutant EGFR selectively as compared to wild type EGFR.

DETAILED DESCRIPTION OF THE INVENTION

Hereinafter, the present invention will be described in more detail.

Unless otherwise defined, all technical terms used herein have the same meaning as commonly understood by one of ordinary skill in the art to which this invention belongs. Also, although the invention has been described in conjunction with specific methods and samples, their analogs or equivalents should be within the scope of the present invention. Furthermore, the numerical values set forth herein are considered to include the meaning of "about" unless explicitly stated. All publications and other references mentioned herein are hereby incorporated by reference in their entirety.

The definition of residues used herein is described in detail. Unless otherwise indicated, each residue has the following definition and is used in the sense as commonly understood by one of ordinary skill in the art.

As used herein, the term "halo" "halogen", "halide (s)" includes fluoro, chloro, bromo and iodo.

As used herein, the "alkyl" refers to an aliphatic hydrocarbon radical, and includes both linear and branched hydrocarbon radicals. For example, $C_{1-6}$ alkyl is an aliphatic hydrocarbon having 1 to 6 carbon atoms and includes methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl. Unless otherwise defined, the alkyl refers to $C_{1-6}$ alkyl, preferably $C_{1-4}$ alkyl, more preferably $C_{1-3}$ alkyl.

As used herein, the "alkenyl" refers to an aliphatic hydrocarbon radical comprising at least one carbon-carbon double bond, and includes both linear and branched hydrocarbon radicals. The unlimited example of the "alkenyl" is vinyl, allyl, but-1-enyl or but-2-enyl.

As used herein, the "alkynyl" refers to an aliphatic hydrocarbon radical comprising at least one carbon-carbon triple bond, and includes both linear and branched hydrocarbon radicals. The unlimited example of the "alkynyl" is ethynyl, propargyl, but-1-ynyl or but-2-ynyl.

As used herein, the "haloalkyl" refers to an alkyl group substituted with one or more halogen atom, and the alkyl group is defined as above. The "halo" refers to F, Cl, Br, or I, and the term is compatibly used with the term "halogen". Unless otherwise defined, the haloalkyl refers tofluoromethyl, difluoromethyl, chloromethyl, trifluoromethyl or 2,2, 2-trifluoroethyl.

As used herein, the term "alkoxy" refers to —O-alkyl or alkyl-O— group, and the alkyl group is defined as shown above. For example, it includes methoxy, ethoxy, n-propoxy, n-butoxy and t-butoxy.

As used herein, the term "hydroxy" or "hydroxyl" alone or in combination with other terms means —OH.

As used herein, the term "hydroxyalkyl" refers to any hydroxyl derivative of alkyl radical. The term "hydroxyalkyl" includes any alkyl radical having one or more hydrogen atoms replaced by a hydroxy group.

As used herein, "amino" refers to —NH$_2$.

As used herein, the term "cycloalkyl" refers to a cyclic alkyl which may be substituted or unsubstituted, and for example, the $C_{3-20}$ cycloalkyl represents a monovalent saturated hydrocarbon ring system having 3 to 20 carbon atoms. Examples of the cycloalkyl include, but are not limited to, cyclopropyl, cyclobutyl, cyclopentyl, cyclohexyl, cycloheptyl, cyclooctyl and the like. Preferably, unless otherwise defined, the cycloalkyl may be $C_{3-8}$ cycloalkyl, or $C_{3-6}$ cycloalkyl.

As used herein, the term "aryl" refers to a monovalent aromatic hydrocarbon having, for example, 6 to 20 carbon atoms ($C_{6-20}$) that is derived by the removal of one hydrogen atom from a single carbon atom of a parent aromatic ring system. The aryl may include a bicyclic radical containing an aromatic ring fused to a saturated or partially unsaturated ring. Exemplary aryl groups may include radicals derived from benzene (phenyl), substituted phenyl, biphenyl, naphthyl, toluyl, naphthalenyl, anthracenyl, indenyl, indanyl, and the like. Unless otherwise defined, the aryl refers to $C_{6-12}$ aryl, preferably $C_{6-10}$ aryl.

As used herein, the "heterocycle" refers to an aromatic, saturated or partially unsaturated mono-, bi- or poly-ring system containing the specified number of ring atoms, and include one or more heteroatoms selected from N, O, and S as a ring member, wherein the heterocyclic ring is connected to the base molecule via a ring atom, which may be C or N. Bicyclic systems may be connected via a 1,1-fusion (spiro), a 1,2-fusion (fused) or a 1,>2-fusion (bridgehead).

As used herein, the "heteroaryl" refers to a monovalent or divalent substituent derived from a monoheterocyclic or polyheterocyclic aromatic hydrocarbon having 1 to 10 carbon ring members containing one or more, preferably one to three, heteroatoms selected among N, O, and S. Examples of the heteroaryl include, but are not limited to, thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazoly, 1,1,3,4-oxadiazolyl, 1,2,4-thiadiazolyl, 1,3,4-thiadiazolyl, triazolyl, tetrazolyl, triazinyl, indolyl, and the like. Examples of the bicyclic heteroaryl include indolyl, benzothiophenyl, benzofuranyl, benzimidazolyl, benzoxazolyl, benzisoxazolyl, benzthiazolyl, benzthiadiazolyl, quinolinyl, isoquinolinyl, furopyridinyl and similar groups thereof, but are not limited thereto. Unless otherwise defined, the heteroaryl is 4-12 membered heteroaryl 1, preferably 4-10 membered heteroaryl, more preferably 4-7 heteroaryl.

As used herein, the "heterocycloalkyl" refers to monocyclic, bicyclic, tricyclic or higher cyclic alkyl having 3 to 10 carbon ring members containing one or more, for example, one to four, heteroatoms selected among N, O, and S. In addition, the heterocycle according to the present invention may also be a fused or bridged heterocycloalkyl. Examples of non-aromatic rings include azetidinyl, oxetanyl, tetrahydrothienyl, tetrahydrofuranyl, pyrrolinyl, pyrrolidinyl, imidazolinyl, imidazolidinyl, oxazolinyl, oxazolidinyl, oxapiperazinyl, oxapiperidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyranyl, dihydropyranyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, teterahydropyrazolopyridinyl, morpholinyl, indolinyl, thiomorpholinyl, azepanyl, diazepanyl, azaadamantanyl, diazamantanyl, and the like, but are not limited thereto. Attachment of a heterocycloalkyl substituent can occur via a carbon atom or a heteroatom. A heterocycloalkyl group may be optionally substituted with one or more suitable groups via one or more aforementioned groups. Unless otherwise defined, heterocycloalkyl refers to 4-12 membered heterocycloalkyl, preferably 4-10 membered heterocycloalkyl, more preferably 4-7 heterocycloalkyl.

The present invention provides novel compounds, a pharmaceutically acceptable salt, diastereomers, enantiomers, racemates, tautomers, prodrugs, hydrates, and solvates thereof that are useful for inhibiting epidermal growth factor receptor (EGFR) and for treating diseases and disorders that are mediated by the protein kinase, for example, cell proliferative diseases and disorders such as cancer, immune diseases such as arthritis, rheumatoid arthritis or autoimmune diseases, infections, cardiovascular diseases, and neurodegenerative diseases and disorders.

The present invention also provides pharmaceutical compositions comprising at least one of the compounds of Formula (I) together with a pharmaceutically acceptable carrier, diluent or excipient therefor.

The present invention provides compositions and methods for modulating the activity of the epidermal growth factor receptor (EGFR) mutants. In one aspect, the present invention provides compounds which act as inhibitors of EGFR mutants.

In one embodiment, provided herein is a compound of Formula (I) shown below, a pharmaceutically acceptable salt, diastereomers, enantiomers, racemates, tautomers, prodrugs, hydrates, or solvates thereof:

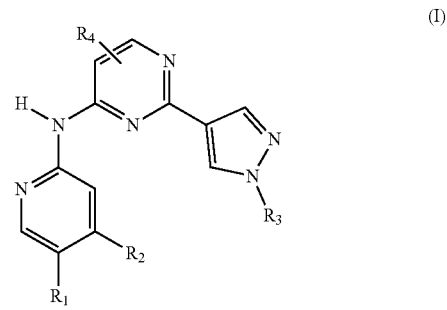

(I)

wherein
$R_1$ is selected from the group consisting of
halogen;
$C_{1-6}$alkyl optionally substituted by one or more substituents selected from the group consisting of OH, halogen, $C_{3-6}$cycloalkyl, —NHC$_{1-6}$alkyl, and N(C$_{1-6}$alkyl)$_2$;
$C_{1-3}$alkoxy;
—C(O)—C$_{1-6}$alkyl, optionally substituted by one or more substituents selected from the group consisting of halogen, —NHC$_{1-6}$alkyl, —N(C$_{1-6}$alkyl)$_2$, and 4-7 membered heterocyclyl;
—C(O)—C$_{3-6}$cycloalkyl, optionally substituted by one or more substituents selected from the group consisting of OH and halogen;
—C(O)—C$_{6-10}$ aryl optionally substituted by one or more halogens;
—C(O)-5-6 membered heteroaryl optionally substituted by one or more halogens;
—N(C$_{1-6}$alkyl)$_2$;
—NHC(O)C$_{1-6}$alkyl;
—NHC(O)C$_{3-6}$cycloalkyl, optionally substituted by one or more substituents selected from the group consisting of OH and halogen;
—C(O)NHC$_{1-6}$alkyl optionally substituted by one or more substituents selected from the group consisting of OH and halogen;
—C(O)NHC$_{3-6}$cycloalkyl optionally substituted by one or more substituents selected from the group consisting of OH, halogen and —N(C$_{1-6}$alkyl)$_2$;
—C(O)-3-7 membered heterocyclyl optionally substituted by one or more substituents selected from the group consisting of OH, halogen, C$_{1-6}$alkyl, and C$_{1-6}$hydroxyalkyl; and
4-7 membered heterocyclyl optionally substituted by one or more substituents selected from the group consisting of OH and halogen, $R_2$ is selected from the group consisting of —$XC_{1-6}$alkyl optionally substituted by one or more substituents selected from the group consisting of OH, halogen, and —$N(C_{1-6}$alkyl$)_2$; and —$X(CH_2)_n$-A-$(R_{2A})_o$, X is —NH—, —O—, bond or —C≡C—, n is an integer of 0 to 2, is an integer of 0 to 3, A is selected from the group consisting of $C_{3-8}$cycloalkyl; $C_{6-10}$ aryl; 4-11 membered heterocyclyl; and 5-6 membered heteroaryl, $R_{2A}$ is independently selected from the group consisting of

H;

halogen;

OH;

$NH_2$;

$C_{1-6}$alkyl optionally substituted by one or more substituents selected from the group consisting of OH, $NH_2$, halogen, $C_{3-6}$cycloalkyl, $C_{1-3}$alkoxy, —$NHC_{1-6}$alkyl, —$NHC_{1-6}$hydroxyalkyl, —$NHC_{1-6}$haloalkyl, —$NHC_{3-6}$cycloalkyl, —$N(C_{1-6}$alkyl$)_2$, —$N(C_{1-6}$haloalkyl$)_2$, —$NHC(O)C_{1-6}$alkyl, —$C(O)NHC_{1-6}$alkyl, —$C(O)N(C_{1-6}$alkyl$)_2$, 3-7 membered heterocyclyl and 5-6 membered heteroaryl;

$C_{3-6}$cycloalkyl;

$C_{1-3}$alkoxy optionally substituted by one or more halogens;

—$C(O)NHC_{1-6}$alkyl optionally substituted by one or more substituents selected from the group consisting of OH and halogen;

—$C(O)N(C_{1-6}$alkyl$)_2$ optionally substituted by one or more substituents selected from the group consisting of OH and halogen;

—$NHC_{1-6}$alkyl optionally substituted by one or more substituents selected from the group consisting of OH, halogen, —$NHC_{1-6}$alkyl, —$N(C_{1-6}$alkyl$)_2$, and 3-7 membered heterocyclyl optionally substituted by halogen or —$N(C_{1-6}$alkyl$)_2$;

—$N(C_{1-6}$alkyl$)_2$ where $C_{1-6}$alkyl is optionally substituted by one or more halogens;

—NH-4-7 membered heterocyclyl optionally substituted by $C_{1-6}$alkyl; and 4-7 membered heterocyclyl, $R_3$ is selected from the group consisting of

H;

$C_{1-6}$alkyl optionally substituted by one or more substituents selected from the group consisting of halogen and $C_{3-6}$cycloalkyl;

$C_{3-6}$cycloalkyl;

4-7 membered heterocyclyl;

—$S(O)_2C_{1-6}$alkyl optionally substituted by one or more halogens; and

—$S(O)_2C_{3-6}$cycloalkyl optionally substituted by one or more halogens, and $R_4$ is selected from the group consisting of H, halogen and $C_{1-6}$alkyl.

In certain embodiment, $R_1$ is F; Cl; $C_{1-3}$alkyl optionally substituted by one to three substituents selected from the group consisting of OH, F, Cl, $C_{3-6}$cycloalkyl, —$NHC_{1-3}$alkyl, and $N(C_{1-3}$alkyl$)_2$; $C_{1-2}$alkoxy; —C(O)—$C_{1-3}$alkyl, optionally substituted by one to three substituents selected from the group consisting of F, and Cl, —$NHC_{1-3}$alkyl, —$N(C_{1-3}$alkyl$)_2$, and 4-7 membered heterocyclyl having one to three heteroatoms selected from a group consisting of N, O and S; —C(O)—$C_{3-6}$cycloalkyl, optionally substituted by one to three substituents selected from the group consisting of OH and halogen; —C(O)phenyl optionally substituted by one to three F, or Cl; —C(O)-5-6 membered heteroaryl optionally substituted by one to three F, Br, Cl or I; —$N(C_{1-3}$alkyl$)_2$; —$NHC(O)C_{1-3}$alkyl; —NHC(O)$C_{3-6}$cycloalkyl, optionally substituted by one to three substituents selected from the group consisting of OH, F, Br, Cl and I; —$C(O)NHC_{1-3}$alkyl optionally substituted by one to three substituents selected from the group consisting of OH, F and Cl; —$C(O)NHC_{3-6}$cycloalkyl optionally substituted by one or more substituents selected from the group consisting of OH, F, Br, Cl, I and —$N(C_{1-3}$alkyl$)_2$; —C(O)-3-7 membered heterocyclyl optionally substituted by one to three substituents selected from the group consisting of OH, F, Cl, $C_{1-6}$alkyl, and $C_{1-6}$hydroxyalkyl; or 4-7 membered heterocyclyl.

In further certain embodiment, $R_1$ is —C(O)—$C_{1-6}$alkyl, optionally substituted by one or more substituents selected from the group consisting of halogen, —$NHC_{1-6}$alkyl, —$N(C_{1-6}$alkyl$)_2$, and 4-7 membered heterocyclyl; —C(O)—$C_{3-6}$cycloalkyl, optionally substituted by one or more substituents selected from the group consisting of OH and halogen; or —$C(O)NHC_{1-3}$alkyl optionally substituted by one to three substituents selected from the group consisting of OH, F and Cl.

In another certain embodiment, $R_1$ is —C(O)—$C_{1-6}$alkyl, optionally substituted by one or more substituents selected from the group consisting of halogen, —$NHC_{1-6}$alkyl, —$N(C_{1-6}$alkyl$)_2$, and 4-7 membered heterocyclyl.

In another certain embodiment, $R_1$ is —C(O)—$C_{3-6}$cycloalkyl, optionally substituted by one or more substituents selected from the group consisting of OH and halogen.

In another certain embodiment, $R_1$ is —$C(O)NHC_{1-3}$alkyl optionally substituted by one to three substituents selected from the group consisting of OH, F and Cl.

In another certain embodiment, $R_1$ is selected from the group consisting of halogen;

—C(O)—$C_{1-6}$alkyl, optionally substituted by one or more substituents selected from the group consisting of halogen and 4-7 membered heterocyclyl;

—C(O)—$C_{3-6}$cycloalkyl;

—C(O)-phenyl optionally substituted by one or more halogens;

—NHC(O)$C_{3-6}$cycloalkyl;

—$C(O)NHC_{1-6}$alkyl optionally substituted by one or more halogens;

—$C(O)NHC_{3-6}$cycloalkyl optionally substituted by one or more OHs;

—C(O)-3-7 membered heterocyclyl optionally substituted by one or more halogens; and 4-7 membered heterocyclyl.

In the above embodiments of $R_1$, the 3-7 membered heterocyclyl or 4-7 membered heterocyclyl may be tetrahydropyranyl, azetidinyl, or 3,4-dihydropyranyl.

In certain embodiment, $R_2$ is —$XC_{1-6}$alkyl optionally substituted by one or more substituents selected from the group consisting of OH, halogen, and —$N(C_{1-6}$alkyl$)_2$.

In further certain embodiment, $R_2$ is —$X(CH_2)_n$-A-$(R_{2A})_o$.

In certain embodiment, X is —NH—, —O—, or bond.

In certain embodiment, A is $C_{3-6}$cycloalkyl; phenyl; 4-10 membered heterocyclyl having one to three heteroatoms selected from a group consisting of N, O and S; or 5-6 membered heteroaryl having one to three heteroatoms selected from a group consisting of N, O and S.

In further certain embodiment, A is $C_{3-6}$cycloalkyl.

In another certain embodiment, A is 4-10 membered heterocyclyl or 5-6 membered heteroaryl having one to three heteroatoms selected from a group consisting of N and O.

In another certain embodiment, A is $C_{3-8}$cycloalkyl, phenyl, pyrazolyl, pyridinyl, tetrahydrofuranyl, tetrahydropyranyl, thienyl, or piperidinyl.

In certain embodiment, $R_{2A}$ is H; F; Cl; OH; $NH_2$; $C_{1-4}$alkyl optionally substituted by one or more substituents selected from the group consisting of OH, $NH_2$, F, Cl, $C_{3-6}$cycloalkyl, $C_{1-3}$alkoxy, —$NHC_{1-3}$alkyl, —$NHC_{1-3}$hydroxyalkyl, —$NHC_{1-3}$haloalkyl, —$NHC_{3-6}$cycloalkyl, —$N(C_{1-3}$alkyl$)_2$, —$N(C_{1-3}$haloalkyl$)_2$, —$NHC(O)C_{1-3}$alkyl, —$C(O)NHC_{1-3}$alkyl, —$C(O)N(C_{1-6}$alkyl$)_2$, 3-7 membered heterocyclyl, and 5-6 membered heteroaryl having one to three heteroatoms selected from a group consisting of N, O and S; $C_{3-6}$cycloalkyl; $C_{1-3}$alkoxy optionally substituted by one to three F or Cl; —$C(O)NHC_{1-3}$alkyl optionally substituted by one to three substituents selected from the group consisting of OH, F and Cl; —$C(O)N(C_{1-3}$alkyl$)_2$ optionally substituted by one to three substituents selected from the group consisting of OH, F and Cl; —$NHC_{1-3}$alkyl optionally substituted by one to three substituents selected from the group consisting of OH, F, Cl, —$NHC_{1-3}$alkyl, —$N(C_{1-3}$alkyl$)_2$, 3-6 membered heterocyclyl one to three heteroatoms selected from a group consisting of N, O and S optionally substituted by F, Cl or —$N(C_{1-3}$alkyl$)_2$; —$N(C_{1-3}$alkyl$)_2$ where $C_{1-3}$alkyl is optionally substituted by one to three F or Cl; —NH-4-6 membered heterocyclyl one to three heteroatoms selected from a group consisting of N, O and S optionally substituted by $C_{1-3}$alkyl; or 4-7 membered heterocyclyl.

In further certain embodiment, $R_{2A}$ is OH; $C_{1-6}$alkyl optionally substituted by one or more substituents selected from the group consisting of OH, $NH_2$, halogen, $C_{3-6}$cycloalkyl, $C_{1-3}$alkoxy, —$NHC_{1-6}$alkyl, —$NHC_{1-6}$hydroxyalkyl, —$NHC_{1-6}$haloalkyl, —$NHC_{3-6}$cycloalkyl, —$N(C_{1-6}$alkyl$)_2$, —$N(C_{1-6}$haloalkyl$)_2$, —$NHC(O)C_{1-6}$alkyl, —$C(O)NHC_{1-6}$alkyl, —$C(O)N(C_{1-6}$alkyl$)_2$, 3-7 membered heterocyclyl, and 5-6 membered heteroaryl having one to three heteroatoms selected from a group consisting of N, O and S; —$C(O)NHC_{1-3}$alkyl optionally substituted by one to three substituents selected from the group consisting of OH, F and Cl; or —$NHC_{1-3}$alkyl optionally substituted by one to three substituents selected from the group consisting of OH, halogen, —$NHC_{1-3}$alkyl, —$N(C_{1-3}$alkyl$)_2$, 3-7 membered heterocyclyl one to three heteroatoms selected from a group consisting of N, O and S optionally substituted by halogen or —$N(C_{1-3}$alkyl$)_2$.

In another further certain embodiment, $R_{2A}$ is independently selected from the group consisting of

H;

halogen;

OH;

$C_{1-6}$alkyl optionally substituted by one or more substituents selected from the group consisting of OH, $NH_2$, halogen, $C_{3-6}$cycloalkyl, —$NHC_{1-6}$alkyl, —$NHC_{1-6}$hydroxyalkyl, —$NHC_{1-6}$ haloalkyl, —$NHC_{3-6}$cycloalkyl, —$N(C_{1-6}$alkyl$)_2$, —$NHC(O)C_{1-6}$alkyl, 3-7 membered heterocyclyl, imidazolyl, and pyrazolyl;

—$NHC_{1-6}$alkyl optionally substituted by one or more substituents selected from the group consisting of OH, halogen, —$N(C_{1-6}$alkyl$)_2$, and 3-7 membered heterocyclyl optionally substituted by halogen or —$N(C_{1-6}$alkyl$)_2$;

—$N(C_{1-6}$alkyl$)_2$;

—NH-4-7 membered heterocyclyl optionally substituted by $C_{1-6}$alkyl; and 4-7 membered heterocyclyl.

In the above embodiments of $R_{2A}$, the 3-7 membered heterocyclyl or 4-7 membered heterocyclyl may be oxetanyl, piperazinyl, azetidinyl, or piperidinyl.

In certain embodiment, $R_3$ is H, $C_{1-4}$alkyl optionally substituted by one to three substituents selected from the group consisting of F, Cl and $C_{3-6}$cycloalkyl; $C_{3-6}$cycloalkyl; 4-6 membered heterocyclyl; —$S(O)_2C_{1-3}$alkyl optionally substituted by one to three F or Cl; or —$S(O)_2C_{3-6}$cycloalkyl optionally substituted by one to three F or Cl.

In further certain embodiment, $R_3$ is —$S(O)_2C_{1-3}$alkyl optionally substituted by one to three F or Cl; or —$S(O)_2C_{3-6}$cycloalkyl optionally substituted by one to three F or Cl.

In another further certain embodiment, $R_3$ is selected from the group consisting of

H;

$C_{1-6}$alkyl optionally substituted by one or more substituents selected from the group consisting of halogen and $C_{3-6}$cycloalkyl;

$C_{3-6}$cycloalkyl;

tetrahydrofuranyl; and

—$S(O)_2C_{3-6}$cycloalkyl.

In certain embodiment, $R_4$ is H.

Representative compounds of Formula (I) are listed below:

(1) Cyclopropyl(6-((2-(1-(cyclopropylsulfonyl)-1H-pyrazol-4-yl)pyrimidin-4-yl)amino)-4-(isopropylamino)pyridin-3-yl)methanone;

(2) Cyclopropyl(4-(cyclopropylamino)-6-((2-(1-(cyclopropylsulfonyl)-1H-pyrazol-4-yl)pyrimidin-4-yl)amino)pyridin-3-yl)methanone;

(3) Cyclopropyl(6-((2-(1-(cyclopropylsulfonyl)-1H-pyrazol-4-yl)pyrimidin-4-yl)amino)-4-((2-fluoroethyl)amino)pyridin-3-yl)methanone;

(4) Cyclopropyl(6-((2-(1-(cyclopropylsulfonyl)-1H-pyrazol-4-yl)pyrimidin-4-yl)amino)-4-((4-fluorobutyl)amino)pyridin-3-yl)methanone;

(5) Cyclopropyl(6-((2-(1-(cyclopropylsulfonyl)-1H-pyrazol-4-yl)pyrimidin-4-yl)amino)-4-((4,4-difluorobutyl)amino)pyridin-3-yl)methanone;

(6) Cyclopropyl(6-((2-(1-(cyclopropylsulfonyl)-1H-pyrazol-4-yl)pyrimidin-4-yl)amino)-4-((2-(tetrahydrofuran-3-yl)ethyl)amino)pyridin-3-yl)methanone;

(7) (R)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone;

(8) (S)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone;

(9) Cyclopropyl(6-((2-(1-(cyclopropylsulfonyl)-1H-pyrazol-4-yl)pyrimidin-4-yl)amino)-4-((3-hydroxypropyl)amino)pyridin-3-yl)methanone;

(10) Cyclopropyl(6-((2-(1-(cyclopropylsulfonyl)-1H-pyrazol-4-yl)pyrimidin-4-yl)amino)-4-(((tetrahydro-2H-pyran-2-yl)methyl)amino)pyridin-3-yl)methanone;

(11) (R)-Cyclopropyl(6-((2-(1-(cyclopropylsulfonyl)-1H-pyrazol-4-yl)pyrimidin-4-yl)amino)-4-((3-hydroxybutyl)amino)pyridin-3-yl)methanone;

(12) Cyclopropyl(6-((2-(1-(cyclopropylsulfonyl)-1H-pyrazol-4-yl)pyrimidin-4-yl)amino)-4-((3-hydroxy-2-methylbutan-2-yl)amino)pyridin-3-yl)methanone;

(13) Cyclopropyl(6-((2-(1-(cyclopropylsulfonyl)-1H-pyrazol-4-yl)pyrimidin-4-yl)amino)-4-((3-(hydroxymethyl)cyclopentyl)amino)pyridin-3-yl)methanone;

(14) Cyclopropyl(6-((2-(1-(cyclopropylsulfonyl)-1H-pyrazol-4-yl)pyrimidin-4-yl)amino)-4-((2-(dimethylamino)ethyl)amino)pyridin-3-yl)methanone;
(15) Cyclopropyl(6-((2-(1-(cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)methanone;
(16) Cyclopropyl(6-((2-(1-(difluoromethyl)-1H-pyrazol-4-yl)pyrimidin-4-yl)amino)-4-((4-((dimethylamino)methyl)benzyl)amino)pyridin-3-yl)methanone;
(17) Cyclopropyl(6-((2-(1-(cyclopropylsulfonyl)-1H-pyrazol-4-yl)pyrimidin-4-yl)amino)-4-(((1-(2-fluoroethyl)-1H-pyrazol-4-yl)methyl)amino)pyridin-3-yl)methanone;
(18) Cyclopropyl(4-(((1-(cyclopropylmethyl)piperidin-4-yl)methyl)amino)-6-((2-(1-(cyclopropylsulfonyl)-1H-pyrazol-4-yl)pyrimidin-4-yl)amino)pyridin-3-yl)methanone;
(19) Cyclopropyl(6-((2-(1-(cyclopropylsulfonyl)-1H-pyrazol-4-yl)pyrimidin-4-yl)amino)-4-(((6-((dimethylamino)methyl)pyridin-3-yl)methyl)amino)pyridin-3-yl)methanone;
(20) Cyclopropyl(6-((2-(1-(cyclopropylsulfonyl)-1H-pyrazol-4-yl)pyrimidin-4-yl)amino)-4-(((5-((dimethylamino)methyl)thiophen-2-yl)methyl)amino)pyridin-3-yl)methanone;
(21) Cyclopropyl(6-((2-(1-(cyclopropylsulfonyl)-1H-pyrazol-4-yl)pyrimidin-4-yl)amino)-4-((2-(4-(dimethylamino)piperidin-1-yl)ethyl)amino)pyridin-3-yl)methanone;
(22) Cyclopropyl(6-((2-(1-(cyclopropylsulfonyl)-1H-pyrazol-4-yl)pyrimidin-4-yl)amino)-4-(((1S,3S)-3-hydroxycyclohexyl)amino)pyridin-3-yl)methanone;
(23) Cyclopropyl(6-((2-(1-(cyclopropylsulfonyl)-1H-pyrazol-4-yl)pyrimidin-4-yl)amino)-4-(((1s,4s)-4-hydroxycyclohexyl)amino)pyridin-3-yl)methanone;
(24) Cyclopropyl(6-((2-(1-(cyclopropylsulfonyl)-1H-pyrazol-4-yl)pyrimidin-4-yl)amino)-4-(((1S,3S)-3-hydroxycyclopentyl)amino)pyridin-3-yl)methanone;
(25) Cyclopropyl(6-((2-(1-(cyclopropylsulfonyl)-1H-pyrazol-4-yl)pyrimidin-4-yl)amino)-4-(((1S,3R)-3-hydroxycyclopentyl)amino)pyridin-3-yl)methanone;
(26) Cyclopropyl(6-((2-(1-(cyclopropylsulfonyl)-1H-pyrazol-4-yl)pyrimidin-4-yl)amino)-4-(((1R,3R)-3-hydroxycyclopentyl)amino)pyridin-3-yl)methanone;
(27) Cyclopropyl(6-((2-(1-(cyclopropylsulfonyl)-1H-pyrazol-4-yl)pyrimidin-4-yl)amino)-4-(((1R,3S)-3-hydroxycyclohexyl)amino)pyridin-3-yl)methanone;
(28) Cyclopropyl(6-((2-(1-(cyclopropylsulfonyl)-1H-pyrazol-4-yl)pyrimidin-4-yl)amino)-4-((3-hydroxy-2,2-dimethylpropyl)amino)pyridin-3-yl)methanone;
(29) Cyclopropyl(6-((2-(1-(cyclopropylsulfonyl)-1H-pyrazol-4-yl)pyrimidin-4-yl)amino)-4-((2-(1-hydroxycyclopropyl)ethyl)amino)pyridin-3-yl)methanone;
(30) Cyclopropyl(6-((2-(1-(cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)methanone;
(31) Cyclopropyl(6-((2-(1-(cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)methanone;
(32) Cyclopropyl-(6-((2-(1-(cyclopropylsulfonyl)-1H-pyrazol-4-yl)pyrimidin-4-yl)amino)-4-(((1s,4s)-4-(methylamino)cyclohexyl)amino)pyridin-3-yl)methanone;
(33) Cyclopropyl(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)methanone;
(34) Cyclopropyl(6-((2-(1-(cyclopropylsulfonyl)-1H-pyrazol-4-yl)pyrimidin-4-yl)amino)-4-((tetrahydro-2H-pyran-3-yl)amino)pyridin-3-yl)methanone;
(35) Cyclopropyl(6-((2-(1-(cyclopropylsulfonyl)-1H-pyrazol-4-yl)pyrimidin-4-yl)amino)-4-((tetrahydro-2H-pyran-4-yl)amino)pyridin-3-yl)methanone;
(36) Cyclopropyl(6-((2-(1-(cyclopropylsulfonyl)-1H-pyrazol-4-yl)pyrimidin-4-yl)amino)-4-(((3S,4R)-3,4-dihydroxycyclohexyl)amino)pyridin-3-yl)methanone;
(37) Cyclopropyl(6-((2-(1-(cyclopropylsulfonyl)-1H-pyrazol-4-yl)pyrimidin-4-yl)amino)-4-((1-(2-(dimethylamino)ethyl)piperidin-4-yl)amino)pyridin-3-yl)methanone;
(38) Cyclopropyl(6-((2-(1-(cyclopropylsulfonyl)-1H-pyrazol-4-yl)pyrimidin-4-yl)amino)-4-((1-(oxetan-3-yl)piperidin-4-yl)amino)pyridin-3-yl)methanone;
(39) Cyclopropyl(6-((2-(1-(cyclopropylsulfonyl)-1H-pyrazol-4-yl)pyrimidin-4-yl)amino)-4-((1-(2-fluoroethyl)piperidin-3-yl)amino)pyridin-3-yl)methanone;
(40) 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2-(tetrahydro-2H-pyran-4-yl)ethan-1-one;
(41) $N^2$-(2-(1-(Cyclopropylsulfonyl)-1H-pyrazol-4-yl)pyrimidin-4-yl)-5-fluoro-$N^4$-isopropylpyridine-2,4-diamine;
(42) N-(6-((2-(1-(Cyclopropylsulfonyl)-1H-pyrazol-4-yl)pyrimidin-4-yl)amino)-4-isopropoxypyridin-3-yl)cyclopropanecarboxamide;
(43) (4-((((1r,4r)-4-((1H-Imidazol-1-yl)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;
(44) (4-((((1r,4r)-4-((1H-Pyrazol-1-yl)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;
(45) 1-(6-((2-(1-(Cyclopropylsulfonyl)-1H-pyrazol-4-yl)pyrimidin-4-yl)amino)-4-(propylamino)pyridin-3-yl)ethan-1-one;
(46) 1-(6-((2-(1-(Cyclopropylsulfonyl)-1H-pyrazol-4-yl)pyrimidin-4-yl)amino)-4-((3-hydroxy-2-methylbutan-2-yl)amino)pyridin-3-yl)ethan-1-one;
(47) 1-(6-((2-(1-Cyclopropylsulfonylpyrazol-4-yl)pyrimidin-4-yl)amino)-4-((3-(hydroxymethyl)cyclopentyl)amino)-3-pyridyl)ethanone;
(48) 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2,2-difluoroethan-1-one;
(49) 1-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)-2,2-difluoroethan-1-one;
(50) 1-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-2,2-difluoroethan-1-one;
(51) 1-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)-2,2-difluoroethan-1-one;
(52) Cyclopropyl(6-((2-(1-(cyclopropylsulfonyl)-1H-pyrazol-4-yl)pyrimidin-4-yl)amino)-4-((4-((2-hydroxyethyl)amino)cyclohexyl)amino)pyridin-3-yl)methanone;
(53) Cyclopropyl(6-((2-(1-(cyclopropylsulfonyl)-1H-pyrazol-4-yl)pyrimidin-4-yl)amino)-4-((4-((2-(dimethylamino)ethyl)amino)cyclohexyl)amino)pyridin-3-yl)methanone;

(54) Cyclopropyl(6-((2-(1-(cyclopropylsulfonyl)-1H-pyrazol-4-yl)pyrimidin-4-yl)amino)-4-((4-((4-methylpiperazin-1-yl)amino)cyclohexyl)amino)pyridin-3-yl)methanone;
(55) Cyclopropyl(6-((2-(1-(cyclopropylsulfonyl)-1H-pyrazol-4-yl)pyrimidin-4-yl)amino)-4-((4-((2-(3-fluoroazetidin-1-yl)ethyl)amino)cyclohexyl)amino)pyridin-3-yl)methanone;
(56) Cyclopropyl(6-((2-(1-(cyclopropylsulfonyl)-1H-pyrazol-4-yl)pyrimidin-4-yl)amino)-4-((4-((2-(piperidin-1-yl)ethyl)amino)cyclohexyl)amino)pyridin-3-yl)methanone;
(57) Cyclopropyl(6-((2-(1-(cyclopropylsulfonyl)-1H-pyrazol-4-yl)pyrimidin-4-yl)amino)-4-((4-((2-(4-(dimethylamino)piperidin-1-yl)ethyl)amino)cyclohexyl)amino)pyridin-3-yl)methanone;
(58) Cyclopropyl(6-((2-(1-(cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)methanone;
(59) (6-((2-(1H-Pyrazol-4-yl)pyrimidin-4-yl)amino)-4-((((1r,4r)-4-((dimethylamino)methyl)cyclohexyl)methyl)amino)pyridin-3-yl)(cyclopropyl)methanone;
(60) Cyclopropyl(6-((2-(1-cyclopropyl-1H-pyrazol-4-yl)pyrimidin-4-yl)amino)-4-((((1r,4r)-4-((dimethylamino)methyl)cyclohexyl)methyl)amino)pyridin-3-yl)methanone;
(61) Cyclopropyl(6-((2-(1-(cyclopropylmethyl)-1H-pyrazol-4-yl)pyrimidin-4-yl)amino)-4-((((1r,4r)-4-((dimethylamino)methyl)cyclohexyl)methyl)amino)pyridin-3-yl)methanone;
(62) Cyclopropyl(4-((((1r,4r)-4-((dimethylamino)methyl)cyclohexyl)methyl)amino)-6-((2-(1-(tetrahydrofuran-3-yl)-1H-pyrazol-4-yl)pyrimidin-4-yl)amino)pyridin-3-yl)methanone;
(63) 1-(6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)ethan-1-one;
(64) (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(4-fluorophenyl)methanone;
(65) 1-(6-((2-(1-(Cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)ethan-1-one;
(66) Cyclopropyl(6-((2-(1-(cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)methanone;
(67) (4-((((1r,4r)-4-(Aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;
(68) N-(((1r,4r)-4-(((5-(Cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)acetamide;
(69) Cyclopropyl(6-((2-(1-(cyclopropylsulfonyl)-1H-pyrazol-4-yl)pyrimidin-4-yl)amino)-4-((((1r,4r)-4-((isopropylamino)methyl)cyclohexyl)methyl)amino)pyridin-3-yl)methanone;
(70) (4-((((1r,4r)-4-((Cyclopentylamino)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;
(71) Cyclopropyl(6-((2-(1-(cyclopropylsulfonyl)-1H-pyrazol-4-yl)pyrimidin-4-yl)amino)-4-((((1r,4r)-4-(((3-hydroxy-3-methylbutan-2-yl)amino)methyl)cyclohexyl)methyl)amino)pyridin-3-yl)methanone;
(72) N-(((1r,4r)-4-(((5-(Cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)isobutyramide;
(73) Cyclopropyl(6-((2-(1-(cyclopropylsulfonyl)-1H-pyrazol-4-yl)pyrimidin-4-yl)amino)-4-((((1r,4r)-4-(((1,1-difluoropropan-2-yl)amino)methyl)cyclohexyl)methyl)amino)pyridin-3-yl)methanone;
(74) 6-((2-(1-(Cyclopropylsulfonyl)-1H-pyrazol-4-yl)pyrimidin-4-yl)amino)-N-(2-fluoroethyl)-4-(isopropylamino)nicotinamide;
(75) 6-((2-(1-(Cyclopropylsulfonyl)-1H-pyrazol-4-yl)pyrimidin-4-yl)amino)-N-(2-fluoroethyl)-4-(((1R,3S)-3-(hydroxymethyl)cyclopentyl)amino)nicotinamide;
(76) 6-((2-(1-(Cyclopropylsulfonyl)-1H-pyrazol-4-yl)pyrimidin-4-yl)amino)-N-(2-fluoroethyl)-4-(((1s,4s)-4-hydroxy-4-methylcyclohexyl)amino)nicotinamide;
(77) 6-((2-(1-(Cyclopropylsulfonyl)-1H-pyrazol-4-yl)pyrimidin-4-yl)amino)-N-(2-fluoroethyl)-4-(((1s,4s)-4-((2-fluoroethyl)amino)cyclohexyl)amino)nicotinamide;
(78) 6-((2-(1-(Cyclopropylsulfonyl)-1H-pyrazol-4-yl)pyrimidin-4-yl)amino)-N-(2,2-difluoroethyl)-4-(isopropylamino)nicotinamide;
(79) 6-((2-(1-(Cyclopropylsulfonyl)-1H-pyrazol-4-yl)pyrimidin-4-yl)amino)-N-(2,2-difluoroethyl)-4-(((1s,4s)-4-hydroxycyclohexyl)amino)nicotinamide;
(80) 6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)-N-((1r,4r)-4-hydroxycyclohexyl)nicotinamide;
(81) 6-((2-(1-(Cyclopropylsulfonyl)-1H-pyrazol-4-yl)pyrimidin-4-yl)amino)-N-(2,2-difluoroethyl)-4-((((1r,4r)-4-((dimethylamino)methyl)cyclohexyl)methyl)amino)nicotinamide;
(82) (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(3,3-difluoroazetidin-1-yl)methanone;
(83) 6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)-N-(2-fluoroethyl)nicotinamide;
(84) $N^2$-(2-(1-(Cyclopropylsulfonyl)-1H-pyrazol-4-yl)pyrimidin-4-yl)-5-(3,4-dihydro-2H-pyran-6-yl)-$N^4$-isopropylpyridine-2,4-diamine;
(85) (1-(2-((2-(1-(Cyclopropylsulfonyl)-1H-pyrazol-4-yl)pyrimidin-4-yl)amino)-5-fluoropyridin-4-yl)-4-methylpiperidin-4-yl)methanol;
(86) Cyclopropyl(6-((2-(1-(cyclopropylsulfonyl)-1H-pyrazol-4-yl)pyrimidin-4-yl)amino)-4-(((1s,4s)-4-hydroxy-4-hydroxymethyl)cyclohexyl)amino)pyridin-3-yl)methanone;
(87) Cyclopropyl(6-((2-(1-(cyclopropylsulfonyl)-1H-pyrazol-4-yl)pyrimidin-4-yl)amino)-4-((4-fluoro-4-(hydroxymethyl)cyclohexyl)amino)pyridin-3-yl)methanone;
(88) Cyclopropyl(6-((2-(1-(cyclopropylsulfonyl)-1H-pyrazol-4-yl)pyrimidin-4-yl)amino)-4-((((1r,4r)-4-(methylamino)cyclohexyl)methyl)amino)pyridin-3-yl)methanone; and
(89) Cyclopropyl(6-((2-(1-(cyclopropylsulfonyl)-1H-pyrazol-4-yl)pyrimidin-4-yl)amino)-4-((((1r,4r)-4-((methylamino)methyl)cyclohexyl)methyl)amino)pyridin-3-yl)methanone.

Further representative compounds of Formula (I) are listed below:

(3) Cyclopropyl(6-((2-(1-(cyclopropylsulfonyl)-1H-pyrazol-4-yl)pyrimidin-4-yl)amino)-4-((2-fluoroethyl)amino)pyridin-3-yl)methanone;

(8) (S)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone;

(9) Cyclopropyl(6-((2-(1-(cyclopropylsulfonyl)-1H-pyrazol-4-yl)pyrimidin-4-yl)amino)-4-((3-hydroxypropyl)amino)pyridin-3-yl)methanone;

(12) Cyclopropyl(6-((2-(1-(cyclopropylsulfonyl)-1H-pyrazol-4-yl)pyrimidin-4-yl)amino)-4-((3-hydroxy-2-methylbutan-2-yl)amino)pyridin-3-yl)methanone;

(13) Cyclopropyl(6-((2-(1-(cyclopropylsulfonyl)-1H-pyrazol-4-yl)pyrimidin-4-yl)amino)-4-((3-(hydroxymethyl)cyclopentyl)amino)pyridin-3-yl)methanone;

(15) Cyclopropyl(6-((2-(1-(cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)methanone;

(22) Cyclopropyl(6-((2-(1-(cyclopropylsulfonyl)-1H-pyrazol-4-yl)pyrimidin-4-yl)amino)-4-(((1S,3S)-3-hydroxycyclohexyl)amino)pyridin-3-yl)methanone;

(23) Cyclopropyl(6-((2-(1-(cyclopropylsulfonyl)-1H-pyrazol-4-yl)pyrimidin-4-yl)amino)-4-(((1s,4s)-4-hydroxycyclohexyl)amino)pyridin-3-yl)methanone;

(24) Cyclopropyl(6-((2-(1-(cyclopropylsulfonyl)-1H-pyrazol-4-yl)pyrimidin-4-yl)amino)-4-(((1S,3S)-3-hydroxycyclopentyl)amino)pyridin-3-yl)methanone;

(25) Cyclopropyl(6-((2-(1-(cyclopropylsulfonyl)-1H-pyrazol-4-yl)pyrimidin-4-yl)amino)-4-(((1S,3R)-3-hydroxycyclopentyl)amino)pyridin-3-yl)methanone;

(27) Cyclopropyl(6-((2-(1-(cyclopropylsulfonyl)-1H-pyrazol-4-yl)pyrimidin-4-yl)amino)-4-(((1R,3S)-3-hydroxycyclohexyl)amino)pyridin-3-yl)methanone;

(30) Cyclopropyl(6-((2-(1-(cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)methanone;

(33) Cyclopropyl(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)methanone;

(36) Cyclopropyl(6-((2-(1-(cyclopropylsulfonyl)-1H-pyrazol-4-yl)pyrimidin-4-yl)amino)-4-(((3S,4R)-3,4-dihydroxycyclohexyl)amino)pyridin-3-yl)methanone;

(47) 1-(6-((2-(1-Cyclopropylsulfonylpyrazol-4-yl)pyrimidin-4-yl)amino)-4-((3-(hydroxymethyl)cyclopentyl)amino)-3-pyridyl)ethanone;

(49) 1-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)-2,2-difluoroethan-1-one;

(54) Cyclopropyl(6-((2-(1-(cyclopropylsulfonyl)-1H-pyrazol-4-yl)pyrimidin-4-yl)amino)-4-((4-((4-methylpiperazin-1-yl)amino)cyclohexyl)amino)pyridin-3-yl)methanone;

(58) Cyclopropyl(6-((2-(1-(cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)methanone;

(63) 1-(6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)ethan-1-one;

(66) Cyclopropyl(6-((2-(1-(cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)methanone;

(68) N-(((1r,4r)-4-(((5-(Cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)acetamide;

(69) Cyclopropyl(6-((2-(1-(cyclopropylsulfonyl)-1H-pyrazol-4-yl)pyrimidin-4-yl)amino)-4-((((1r,4r)-4-((isopropylamino)methyl)cyclohexyl)methyl)amino)pyridin-3-yl)methanone;

(75) 6-((2-(1-(Cyclopropylsulfonyl)-1H-pyrazol-4-yl)pyrimidin-4-yl)amino)-N-(2-fluoroethyl)-4-(((1R,3S)-3-(hydroxymethyl)cyclopentyl)amino)nicotinamide;

(81) 6-((2-(1-(Cyclopropylsulfonyl)-1H-pyrazol-4-yl)pyrimidin-4-yl)amino)-N-(2,2-difluoroethyl)-4-((((1r,4r)-4-((dimethylamino)methyl)cyclohexyl)methyl)amino)nicotinamide; and

(83) 6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)-N-(2-fluoroethyl)nicotinamide.

Further preferable representative compounds of Formula (I) are listed below:

(3) Cyclopropyl(6-((2-(1-(cyclopropylsulfonyl)-1H-pyrazol-4-yl)pyrimidin-4-yl)amino)-4-((2-fluoroethyl)amino)pyridin-3-yl)methanone;

(8) (S)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone;

(9) Cyclopropyl(6-((2-(1-(cyclopropylsulfonyl)-1H-pyrazol-4-yl)pyrimidin-4-yl)amino)-4-((3-hydroxypropyl)amino)pyridin-3-yl)methanone;

(12) Cyclopropyl(6-((2-(1-(cyclopropylsulfonyl)-1H-pyrazol-4-yl)pyrimidin-4-yl)amino)-4-((3-hydroxy-2-methylbutan-2-yl)amino)pyridin-3-yl)methanone;

(13) Cyclopropyl(6-((2-(1-(cyclopropylsulfonyl)-1H-pyrazol-4-yl)pyrimidin-4-yl)amino)-4-((3-(hydroxymethyl)cyclopentyl)amino)pyridin-3-yl)methanone;

(23) Cyclopropyl(6-((2-(1-(cyclopropylsulfonyl)-1H-pyrazol-4-yl)pyrimidin-4-yl)amino)-4-(((1s,4s)-4-hydroxycyclohexyl)amino)pyridin-3-yl)methanone;

(58) Cyclopropyl(6-((2-(1-(cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)methanone;

(66) Cyclopropyl(6-((2-(1-(cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)methanone; and

(69) Cyclopropyl(6-((2-(1-(cyclopropylsulfonyl)-1H-pyrazol-4-yl)pyrimidin-4-yl)amino)-4-((((1r,4r)-4-((isopropylamino)methyl)cyclohexyl)methyl)amino)pyridin-3-yl)methanone.

Single stereochemical isomers, enantiomers, diastereomers, and pharmaceutically acceptable salts of the above exemplified compounds are also within the scope of the present invention. Pharmaceutically acceptable salts may be, for example, derived from suitable inorganic and organic acids and bases.

Acid addition salts can be prepared by reacting the purified compound in its free-based form, if possible, with a suitable organic or inorganic acid and isolating the salt thus formed. Examples of pharmaceutically acceptable acid addition salts include, without limitations, salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid.

Base addition salts can be prepared by reacting the purified compound in its acid form with a suitable organic or inorganic base and isolating the salt thus formed. Such salts include, without limitations, alkali metal (e.g., sodium, lithium, and potassium), alkaline earth metal (e.g., magnesium and calcium), ammonium and $N^+(C_{1-4}alkyl)_4$ salts.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, and valerate salts.

The compounds of the present invention may be synthesized by methods known in the art or by methods illustrated in Examples 1-89 below.

Pharmaceutical Compositions, Methods and Use

In one embodiment, the present invention relates to a method for treating protein kinase-mediated disease in a subject in need thereof, comprising administering to said subject a therapeutically effective amount of a compound of Formula (I) or a pharmaceutically acceptable salt, diastereomers, enantiomers, racemates, tautomers, prodrugs, hydrates, or solvates thereof In specific embodiment, the protein kinase-mediated disease is a cancer or immune disease.

As used herein, the term "cancer" refers to an abnormal growth of cells which tend to proliferate in an uncontrolled way and, in some cases, to metastasize. The types of cancer include, but is not limited to, solid tumors, such as those of the bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, or other endocrine organ (thyroid cancer), prostate cancer, skin (melanoma) or hematological tumors (such as the leukemias). In another embodiment, the cancer is non-small cell lung cancer (NSCLC).

In one embodiment, the method disclosed herein relates to treatment of cancer, wherein the cancer results from at least one mutation of EGFR.

In one embodiment, the method of treatment of cancer is particularly useful for patient who is resistant to a kinase inhibitor other that a compound of the invention, or a pharmaceutically acceptable salt, solvate, ester, or prodrug thereof. In another embodiment, the kinase inhibitor is a mutated EGFR inhibitor.

The invention also relates to a method for inhibiting at least one mutant of EGFR selectively as compared to wild type EGFR, in biological sample or in a patient, comprising contacting the biological sample with or administering to the patient a compound to the patient a therapeutically effective amount of a compound of the invention, or a pharmaceutically acceptable salt thereof.

In one embodiment, the at least one mutant is at least one single mutant selected from Table 1 shown below.

In one embodiment, the at least one mutant is at least one double mutant selected from Table 1 shown below.

In one embodiment, the at least one mutant is at least one triple mutant selected from Table 1 shown below.

TABLE 1

| Number (#) | Mutation type |
| --- | --- |
| 1 | EGFR Del19 (Del E746-A750) |
| 2 | EGFR L858R |
| 3 | EGFR Del19/T790M |
| 4 | EGFR Del19/C797S |
| 5 | EGFR Del19/C797X (X = G, N) |
| 6 | EGFR Del19/L792X (X = F, H, P, R, V, Y) |
| 7 | EGFR Del19/L718X (X = Q, V) |
| 8 | EGFR L858R/T790M |
| 9 | EGFR L858R/C797S |
| 10 | EGFR L858R/C797X (X = G, N) |
| 11 | EGFR L858R/L792X (X = F, H, P, R, V, Y) |
| 12 | EGFR L858R/L718X (X = Q, V) |
| 13 | EGFR Del19/T790M/C797S |
| 14 | EGFR Del19/T790M/C797X (X = G, N) |
| 15 | EGFR Del19/T790M/L792X (X = F, H, P, R, V, Y) |
| 16 | EGFR Del19/T790M/L718X (X = Q, V) |
| 17 | EGFR L858R/T790M/C797S |
| 18 | EGFR L858R/T790M/C797X (X = G, N) |
| 19 | EGFR L858R/T790M/L792X (X = F, H, P, R, V, Y) |
| 20 | EGFR L858R/T790M/L718X (X = Q, V) |

The invention further relates to therapeutic methods and uses comprising administering the compounds of the invention, or a pharmaceutically acceptable salt, diastereomers, enantiomers, racemates, tautomers, prodrugs, hydrates, or solvates thereof alone or in combination with other therapeutic or palliative agents.

A further embodiment of the invention relates to a compound of the invention for use as a medicament, and in particular for use in the treatment of diseases where the inhibition of mutated EGFR protein (e.g., those described in Table 1) activity may induce benefit, such as cancer. A still further embodiment of the present invention relates to the use of the compounds of the invention, or a pharmaceutically acceptable salt, diastereomers, enantiomers, racemates, tautomers, prodrugs, hydrates, or solvates thereof, for the manufacture of a drug having an EGFR inhibitory activity for the treatment of EGFR mediated diseases and/or conditions, in particular the diseases and/or conditions listed above.

The term "therapeutically effective amount" refers to that amount of a compound being administered which will relieve to some extent one or more of the symptoms of the disorder being treated. Regarding the treatment of cancer, a therapeutically effective amount refers to that amount which has the effect of reducing the size of the tumor, inhibiting (i.e., slowing or stopping) tumor metastases, inhibiting (i.e. slowing or stopping) tumor growth or tumor invasiveness, and/or relieving to some extent one or more signs or symptoms related to the cancer.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

The term "treating", as used herein, unless otherwise indicated, means reversing, alleviating, inhibiting the progress of, or preventing the disorder or condition to which such term applies, or one or more symptoms of such disorder or condition. The term "treatment" also refers to the act of treating as "treating" is defined immediately above. The term "treating" also includes adjuvant treatment of a mammal.

As used herein, the term "subject" or "patient" encompasses mammals and nonmammals. Examples of mammals include, but are not limited to, humans, chimpanzees, apes monkeys, cattle, horses, sheep, goats, swine; rabbits, dogs, cats, rats, mice, guineapigs, and the like. Examples of non-mammals include, but are not limited to, birds, fish and the like.

As used herein, the term "biological sample" encompasses cells, tissues, and body fluids obtained (isolated) from mammals, such as humans (e.g., patients having cancers) or nonmammals exemplified hereinabove, and cultures thereof.

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Also provided herein, in other aspects, is a pharmaceutical composition comprising a compound of t Formula (I), a pharmaceutically acceptable salt, diastereomers, enantiomers, racemates, tautomers, prodrugs, hydrates, or solvates thereof as an active ingredient, and pharmaceutically acceptable excipients. In one embodiment, the pharmaceutical composition is for treating a protein kinase-mediated disease. In another embodiment, the pharmaceutical composition is for selectively inhibiting at least one mutant of EGFR as compared to wild type EGFR.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid.

Examples of carriers, excipients and diluents that can be included in the composition, may include lactose, dextrose, sucrose, sorbitol, mannitol, xylitol, erythritol, maltitol, starch, arabic gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil, but are not limited thereto. When formulated into a preparation, a diluting agent or an excipient, such as commonly-used fillers, stabilizing agents, binding agents, disintegrating agents, and surfactants can be used. Solid preparations for oral administration include tablets, pills, powders, granules, capsules, and the like, and these solid preparations may be prepared by mixing the compound of the present invention with at least one excipient, for example, starch, microcrystalline cellulose, sucrose, lactose, low-substituted hydroxypropyl cellulose, hypromellose or the like. In addition to the simple excipient, a lubricant such as magnesium stearate and talc are also used. Liquid preparations for oral administration include a suspension, a liquid for internal use, an emulsion, a syrup, etc. In addition to a commonly used simple diluent such as water and liquid paraffin, various excipients such as a humectant, a sweetener, an aromatic, a preservative, etc. may also be contained. Formulations for parenteral administration include a sterilized aqueous solution, a non-aqueous solution, a suspension, an emulsion, a lyophilized formulation and a suppository. The non-aqueous solution or suspension may contain propylene glycol, polyethylene glycol, a vegetable oil such as olive oil, an injectable ester such as ethyl oleate, etc. As a base of the suppository, witepsol, macrogol, tween 61, cocoa butter, laurin butter, glycerogelatin, etc. may be used. In order to formulate the formulation for parenteral administration, the compound of Formula I or a pharmaceutically acceptable salt thereof may be mixed in water together with sterilized and/or contain adjuvants such as preservatives, stabilizers, auxiliary agents such as wettable powder or emulsifying accelerators, salt for controlling osmotic pressure and/or buffers and the like, and other therapeutically useful substances, to prepare a solution or suspension, which is then manufactured in the form of an ampoule or vial unit administration.

General Reaction Scheme and Summary of the Synthesis Route

The present invention includes, within its scope, a process for preparing a compound of formula (I) or a pharmaceutically acceptable salt, diastereomers, enantiomers, racemates, tautomers, prodrugs, hydrates, or solvates thereof, in accordance with the following Scheme 1:

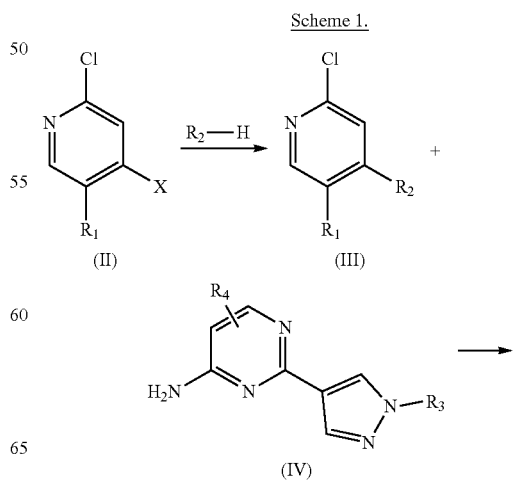

-continued

[Structure of formula (I)]

wherein, $R_1$, $R_2$, $R_3$, and $R_4$ are the same as defined in the above; X is halogen.

Specifically, the compound of formula (I) or its pharmaceutically acceptable salt may be prepared using a process which comprises: reacting a compound of formula (II) with $R_2$—H to obtain a compound of formula (III), reacting the compound of formula (III) with a compound of formula (IV) to obtain a compound of formula (I).

In the processes of Scheme 1, the compounds of formula (II), $R_2$—H and (IV) are commercially available. The reaction of the compound of formula (II) and $R_2$—H may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C.

The compound of formula (III) is coupled with a compound of formula (IV) to obtain a compound of formula (I) by Buchwald-Hartwig reaction. The reaction of the compound of formula (III) and (IV) may be performed in the presence of a base such as sodium carbonate potassium carbonate, cesium carbonate, etc. Further, the reaction may be performed in the presence of a palladium catalyst such as $Pd(OAc)_2$, $Pd_2(dba)_3$, $Pd(PPh_3)_4$, $Pd(dppf)C_{1-2}$, BrettPhos Pd G1 methyl t-butyl ether adduct, etc. and a ligand such as BINAP, SPhos, XPhos, Xantphos, BrettPhos, etc. Further, the reaction may be carried out in an anhydrous organic solvent, e.g., 1,4-dioxane or toluene under heating, e.g. at a temperature of 80-120° C.

Alternately, the compound of formula (II) may be prepared in accordance with the following Scheme 2:

Scheme 2.

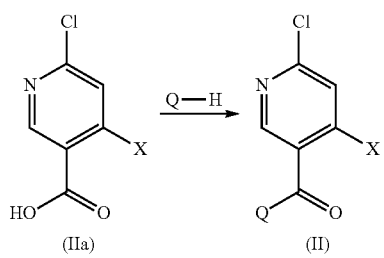

wherein, X is halogen; Q is $NHC_{1-6}$alkyl optionally substituted by one or more substituents selected from the group consisting of OH and halogen, $NHC_{3-6}$cycloalkyl optionally substituted by one or more substituents selected from the group consisting of OH, halogen and —$N(C_{1-6}alkyl)_2$ or 3-7 membered heterocyclyl optionally substituted by one or more substituents selected from the group consisting of OH, halogen, $C_{1-6}$alkyl, and $C_{1-6}$hydroxyalkyl.

Specifically, the compound of formula (II) may be prepared using a process which comprises: reacting a compound of formula (IIa) with Q-H to obtain a compound of formula (II).

In the processes of Scheme 2, the compounds of formula (II), (IIa) and Q-H are commercially available. The reaction of the compound of formula (IIa) and Q-H may be performed in the presence of a base, such as TEA, DIPEA, etc. and a amide coupling reagent such as HOBt, HBTU, BOP, PyBOP, HATU, etc. Further, the reaction may be carried out in an anhydrous organic solvent, e.g., DCM, DMF, acetonitrile, etc. at room temperature or under heating, e.g. at a temperature of 40-120° C.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+ (ESI-MS (cation), which is represented by the (M+H)+ peak). Column chromatography was carried out on silica gel (Merck, 70-230 mesh). (W. C. Still, J. Org. Chem., 43, 2923, 1978). Further, the starting materials in each Example are known compounds, which were synthesized according to literatures or obtained from the market such as Sigma-Aldrich. Further, the abbreviations used in the following examples are as follows:

TABLE 2

| List of abbreviations | |
|---|---|
| DCM | Methylene chloride |
| DIPEA | N,N-Diisopropylethylamine |
| DMA | N,N- Dimethylacetamide |
| DMF | N,N-Dimethylformamide |
| DMSO | Dimethyl sulfoxide |
| EA | Ethyl acetate |
| HATU | Hexafluorophosphate azabenzotriazole tetramethyl uronium |
| $K_2CO_3$ | Potassium carbonate |
| MeCN | Acetonitrile |
| MeOH | Methanol |
| $MgSO_4$ | Magnesium sulfate |
| n-Hex | n-Hexane |
| sat. $NaHCO_3$ soln. | saturated sodium bicarbonate solution |
| TFA | Trifluoroacetic acid |
| XPhos | [2-Dicyclohexylphosphino-2',4',6'-triisopropylbiphenyl] |

Reference Example 1. 4-((5-(Cyclopropanecarbonyl)-2-((2-(1-cyclopropylsulfonylpyrazol-4-yl)pyrimidin-4-yl)amino)-4-pyridyl)amino)cyclohexanone

Step 1. 4-((2-Chloro-5-(cyclopropanecarbonyl)-4-pyridyl)amino)cyclohexanone The reaction mixture of cyclopropyl(4,6-dichloropyridin-3-yl)methanone (1.00 g, 4.628 mmol), 4-aminocyclohexanone HCl (1.04 g, 6.943 mmol) and DIPEA (4.03 mL, 23.142 mmol) in DMF (16 mL) was stirred at 90° C. overnight. The reaction mixture was cooled, diluted in EA, washed by water, dried over MgSO$_4$, and then concentrated. The crude product was purified by column chromatography (EA/n-Hex=0-50%) to yield 4-((2-chloro-5-(cyclopropanecarbonyl)-4-pyridyl)amino)cyclohexanone (489 mg) as an off-white solid. MS (ESI) m/z=293.0 (M+H)$^+$

Step 2. 4-((5-(Cyclopropanecarbonyl)-2-((2-(1-cyclopropylsulfonylpyrazol-4-yl)pyrimidin-4-yl)amino)-4-pyridyl)amino)cyclohexanone The suspension of 2-(1-(cyclopropylsulfonyl)-1H-pyrazol-4-yl)pyrimidin-4-amine (250 mg, 0.943 mmol), tris(dibenzylideneacetone)dipalladium(0) (86 mg, 0.090 mmol), Xphos (90 mg, 0.170 mmol), cesium carbonate (921 mg, 2.833 mmol) and 4-((2-chloro-5-(cyclopropanecarbonyl)-4-pyridyl)amino)cyclohexanone (303 mg, 1.038 mmol) prepared in Step 1 in 1,4-dioxane (5 mL) was stirred at 110° C. overnight. The mixture was diluted in DCM, filtered through Celite, and then concentrated. The crude product was crystallised by EA/n-Hex and triturated with EA/isopropyl ether to yield 4-((5-(cyclopropanecarbonyl)-2-((2-(1-cyclopropylsulfonylpyrazol-4-yl)pyrimidin-4-yl)amino)-4-pyridyl)amino)cyclohexanone (113 mg) as an off-white solid. $^1$H-NMR (CDCl$_3$, 400 MHz) δ 9.72 (d, 1H), 8.87 (s, 1H), 8.64 (s, 1H), 8.44 (s, 1H), 8.42 (d, 1H), 8.25 (s, 1H), 7.42 (s, 1H), 6.99 (d, 1H), 3.39 (brs, 1H), 2.86-2.82 (m, 1H), 2.61-2.57 (m, 1H), 2.09-2.05 (m, 2H), 1.77-1.71 (m, 4H), 1.54-1.51 (m, 2H), 1.43-1.33 (m, 2H), 1.28-1.21 (m, 4H), 1.05-1.00 (m, 2H)

Reference Example 2. (6-Chloro-4-((((1r,4r)-4-((dimethylamino)methyl)cyclohexyl)methyl)amino)pyridin-3-yl)(cyclopropyl)methanone

Step 1. tert-Butyl (((1r,4r)-4-(((2-chloro-5-(cyclopropanecarbonyl)pyridin-4-yl)amino)methyl)cyclohexyl)methyl)carbamate The reaction mixture of cyclopropyl-(4,6-dichloro-3-pyridyl)methanone (481 mg, 2.228 mmol), tert-butyl (((1r,4r)-4-(aminomethyl)cyclohexyl)methyl)carbamate (600 mg, 2.476 mmol) and cesium carbonate (2.02 g, 6.189 mmol) in DMF (5 mL) was stirred at 100° C. for 5 hours. The reaction mixture was cooled, diluted in DCM, washed by water, dried over MgSO$_4$, and then concentrated. The crude product was crystallised by DCM and triturated with isopropyl ether to yield tert-butyl (((1r,4r)-4-(((2-chloro-5-(cyclopropanecarbonyl)pyridin-4-yl)amino)methyl)cyclohexyl)methyl)carbamate (403 mg) as a white solid. MS (ESI) m/z=422.2 (M+H)$^+$

Step 2. (4-((((1r,4r)-4-(Aminomethyl)cyclohexyl)methyl)amino)-6-chloropyridin-3-yl)(cyclopropyl)methanone The reaction mixture of tert-butyl (((1r,4r)-4-(((2-chloro-5-(cyclopropanecarbonyl)pyridin-4-yl)amino)methyl)cyclohexyl)methyl)carbamate (533 mg, 1.263 mmol) prepared in Step 1 and TFA (1.45 mL, 18.943 mmol) in DCM (12.63 mL) was stirred at room temperature overnight, and then concentrated. The residue was diluted in DCM, added 1 N NaOH soln. (>pH 8), washed by water, dried over MgSO$_4$, and then concentrated. The crude product was purified by column chromatography (MeOH/DCM=0-20%) to yield (4-((((1r,4r)-4-(aminomethyl)cyclohexyl)methyl)amino)-6-chloropyridin-3-yl)(cyclopropyl)methanone (60 mg) as a white solid. MS (ESI) m/z=322.2 (M+H)$^+$

Step 3. (6-Chloro-4-((((1r,4r)-4-((dimethylamino)methyl)cyclohexyl)methyl)amino)pyridin-3-yl)(cyclopropyl)methanone The reaction mixture of (4-((((1r,4r)-4-(aminomethyl)cyclohexyl)methyl)amino)-6-chloropyridin-3-yl)(cyclopropyl)methanone (350 mg, 1.087 mmol) prepared in Step 2, formaldehyde (2.43 mL, 32.625 mmol) and sodium triacetoxyborohydride (691.5 mg, 3.262 mmol) in MeOH (10 mL) was stirred at 70° C. overnight. The reaction mixture was cooled, concentrated, diluted in DCM, washed by water, dried over MgSO$_4$, and then concentrated. The crude product was purified by column chromatography (MeOH/DCM=0-20%) to yield (6-chloro-4-((((1r,4r)-4-((dimethylamino)methyl)cyclohexyl)methyl)amino)pyridin-3-yl)(cyclopropyl)methanone (34 mg) as a colorless oil. MS (ESI) m/z=350.2 (M+H)$^+$

Reference Example 3. 4,6-Dichloro-N-(2-fluoroethyl)pyridine-3-carboxamide

The reaction mixture of 4,6-dichloropyridine-3-carboxylic acid (500 mg, 2.604 mmol), 2-fluoroethylamine HCl (259 mg, 2.604 mmol), HATU (1.49 g, 3.906 mmol) and DIPEA (1.36 mL, 7.812 mmol) in DMA (20 mL) was stirred at room temperature overnight. The reaction mixture was cooled at 0° C., sat. NaHCO$_3$ sol. was added thereto, and the mixture was extracted with EA. The organic layer was washed by water, dried over MgSO$_4$, and then concentrated. The crude product was purified by column chromatography (EA/n-Hex=0-50%) to yield 4,6-dichloro-N-(2-fluoroethyl)pyridine-3-carboxamide (318 mg) as a pale yellow liquid. MS (ESI) m/z=238.0 (M+H)$^+$

Reference Example 4. 4,6-Dichloro-N-(2,2-difluoroethyl)pyridine-3-carboxamide The title compound as a pale yellow liquid (452 mg) was prepared in the same fashion as Reference Example 3, except that 2,2-difluoroethylamine (211 mg, 2.604 mmol) was used instead of 2-fluoroethylamine HCl. MS (ESI) m/z=255.0 (M+H)$^+$

Example 1. Cyclopropyl(6-((2-(1-(cyclopropylsulfonyl)-1H-pyrazol-4-yl)pyrimidin-4-yl)amino)-4-(isopropylamino)pyridin-3-yl)methanone

Step 1. (6-Chloro-4-(isopropylamino)-3-pyridyl)cyclopropylmethanone

The reaction mixture of cyclopropyl(4,6-dichloropyridin-3-yl)methanone (200 mg, 0.926 mmol), isopropylamine (60 mg, 1.018 mmol) and K$_2$CO$_3$ (256 mg, 1.851 mmol) in DMF (2 mL) was stirred at 80° C. overnight. The reaction mixture was cooled, diluted in EA, washed by water, dried over MgSO$_4$, and then concentrated. The crude product was purified by column chromatography (EA/n-Hex=0-50%) to yield (6-chloro-4-(isopropylamino)-3-pyridyl)cyclopropylmethanone (160 mg) as an off-white solid. MS (ESI) m/z=238.9 (M+H)+

Step 2. Cyclopropyl(6-((2-(1-(cyclopropylsulfonyl)-1H-pyrazol-4-yl)pyrimidin-4-yl)amino)-4-(isopropylamino)pyridin-3-yl)methanone The suspension of 2-(1-(cyclopropylsulfonyl)-1H-pyrazol-4-yl)pyrimidin-4-amine (67 mg, 0.251 mmol), tris(dibenzylideneacetone)dipalladium(0) (10 mg, 0.01 mmol), BINAP (13 mg, 0.021 mmol), cesium carbonate (205 mg, 0.628 mmol) and (6-chloro-4-(isopropylamino)-3-pyridyl)cyclopropylmethanone (50 mg, 0.209 mmol) prepared in Step 1 in 1,4-dioxane (1.5 mL) was stirred at 110° C. overnight. The mixture was diluted in DCM, filtered through Celite, and then concentrated. The crude product was crystallised by EA/Hex and triturated with EA/isopropyl ether to yield cyclopropyl-(6-((2-(1-cyclopropylsulfonylpyrazol-4-yl)pyrimidin-4-yl)amino)-4-(isopropylamino)-3-pyridyl)methanone (21 mg) as an off-white solid. $^1$H-NMR (CDCl$_3$, 400 MHz) δ 9.30 (d, 1H), 8.82 (s, 1H), 8.64 (s, 1H), 8.45 (s, 1H), 8.44 (d, 1H), 8.18 (s, 1H), 7.44 (s, 1H), 7.04 (d, 1H), 3.86-3.82 (m, 1H), 2.85-2.82 (m, 1H), 2.60-2.56 (m, 1H), 1.54-1.51 (m, 2H), 1.37 (d, 6H), 1.26-1.19 (m, 4H), 1.01-0.99 (m, 2H); MS (ESI) m/z=468.2 (M+H)+

Example 2. Cyclopropyl(4-(cyclopropylamino)-6-((2-(1-(cyclopropylsulfonyl)-1H-pyrazol-4-yl)pyrimidin-4-yl)amino)pyridin-3-yl)methanone Step 1. (6-Chloro-4-(cyclopropylamino)-3-pyridyl)cyclopropylmethanone The title compound as a solid (169 mg) was prepared in the same fashion as Step 1 in Example 1 except that cyclopropylamine (58 mg, 1.018 mmol) was used instead of isopropylamine. MS (ESI) m/z=236.9 (M+H)+

Step 2. Cyclopropyl(4-(cyclopropylamino)-6-((2-(1-(cyclopropylsulfonyl)-1H-pyrazol-4-yl)pyrimidin-4-yl)amino)pyridin-3-yl)methanone The title compound (16 mg) was prepared in the same fashion as Step 2 in Example 1, except that (6-chloro-4-(cyclopropylamino)-3-pyridyl)cyclopropylmethanone (50 mg, 0.211 mmol) prepared in Step 1 was used instead of (6-chloro-4-(isopropylamino)-3-pyridyl)cyclopropylmethanone. $^1$H-NMR (CDCl$_3$, 400 MHz) δ 9.26 (d, 1H), 8.84 (s, 1H), 8.65 (s, 1H), 8.46 (s, 1H), 8.45 (d, 1H), 8.00 (s, 1H), 7.59 (s, 1H), 7.17 (d, 1H), 2.82-2.79 (m, 1H), 2.63-2.58 (m, 2H), 1.52-1.50 (m, 2H), 1.24-1.17 (m, 4H), 1.01-0.99 (m, 2H), 0.93-0.90 (m, 2H), 0.63-0.60 (m, 2H); MS (ESI) m/z=466.2 (M+H)+

Example 3. Cyclopropyl(6-((2-(1-(cyclopropylsulfonyl)-1H-pyrazol-4-yl)pyrimidin-4-yl)amino)-4-((2-fluoroethyl)amino)pyridin-3-yl)methanone Step 1. (6-Chloro-4-(2-fluoroethylamino)-3-pyridyl)cyclopropylmethanone The title compound as a solid (141 mg) was prepared in the same fashion as Step 1 in Example 1 except that 2-fluoroethanamine HCl (101 mg, 1.018 mmol) was used instead of isopropylamine. MS (ESI) m/z=243.1 (M+H)+

Step 2. Cyclopropyl(6-((2-(1-(cyclopropylsulfonyl)-1H-pyrazol-4-yl)pyrimidin-4-yl)amino)-4-((2-fluoroethyl)amino)pyridin-3-yl)methanone The title compound (13 mg) was prepared in the same fashion as Step 2 in Example 1, except that (6-chloro-4-(2-fluoroethylamino)-3-pyridyl)cyclopropylmethanone (50 mg, 0.206 mmol) prepared in Step 1 was used instead of (6-chloro-4-(isopropylamino)-3-pyridyl)cyclopropylmethanone. $^1$H-NMR (CDCl$_3$, 400 MHz) δ 9.58 (d, 1H), 8.88 (s, 1H), 8.67 (s, 1H), 8.44 (s, 2H), 8.08 (s, 1H), 7.44 (s, 1H), 7.01 (d, 1H), 4.76 (d, 2H), 3.65 (dd, 2H), 2.87-2.81 (m, 1H), 2.62-2.57 (m, 1H), 1.56-1.53 (m, 2H), 1.24-1.22 (m, 4H), 1.05-1.01 (m, 2H); MS (ESI) m/z=472.2 (M+H)+

Example 4. Cyclopropyl(6-((2-(1-(cyclopropylsulfonyl)-1H-pyrazol-4-yl)pyrimidin-4-yl)amino)-4-((4-fluorobutyl)amino)pyridin-3-yl)methanone Step 1. (6-Chloro-4-(4-fluorobutylamino)-3-pyridyl)cyclopropylmethanone The title compound as a solid (201 mg) was prepared in the same fashion as Step 1 in Example 1 except that 4-fluorobutan-1-amine HCl (130 mg, 1.018 mmol) was used instead of isopropylamine. MS (ESI) m/z=271.1 (M+H)+

Step 2. Cyclopropyl(6-((2-(1-(cyclopropylsulfonyl)-1H-pyrazol-4-yl)pyrimidin-4-yl)amino)-4-((4-fluorobutyl)amino)pyridin-3-yl)methanone The title compound (14 mg) was prepared in the same fashion as Step 2 in Example 1, except that (6-chloro-4-(4-fluorobutylamino)-3-pyridyl)cyclopropylmethanone (50 mg, 0.185 mmol) prepared in Step 1 was used instead of (6-chloro-4-(isopropylamino)-3-pyridyl)cyclopropylmethanone $^1$H-NMR (CDCl$_3$, 400 MHz) δ 9.29 (d, 1H), 8.87 (s, 1H), 8.66 (s, 1H), 8.45 (s, 2H), 7.58 (s, 1H), 7.36 (d, 1H), 7.15 (d, 1H), 4.57 (d, 1H), 4.45 (d, 1H), 3.42-3.35 (m, 2H), 2.86-2.81 (m, 1H), 2.64-2.58 (m, 1H), 1.93-1.82 (m, 4H), 1.61-1.53 (m, 2H), 1.26-1.21 (m, 4H), 1.05-1.01 (m, 2H)

Example 5. Cyclopropyl(6-((2-(1-(cyclopropylsulfonyl)-1H-pyrazol-4-yl)pyrimidin-4-yl)amino)-4-((4,4-difluorobutyl)amino)pyridin-3-yl)methanone Step 1. (6-Chloro-4-(4,4-difluorobutylamino)-3-pyridyl)cyclopropylmethanone The title compound as a solid (187 mg) was prepared in the same fashion as Step 1 in Example 1 except that 4,4-difluorobutan-1-amine HCl (148 mg, 1.018 mmol) was used instead of isopropylamine. MS (ESI) m/z=289.1 (M+H)+

Step 2. Cyclopropyl(6-((2-(1-(cyclopropylsulfonyl)-1H-pyrazol-4-yl)pyrimidin-4-yl)amino)-4-((4,4-difluorobutyl)amino)pyridin-3-yl)methanone The title compound (19 mg) was prepared in the same fashion as Step 2 in Example 1, except that (6-chloro-4-(4,4-difluorobutylamino)-3-pyridyl)cyclopropylmethanone (50 mg, 0.173 mmol) prepared in Step 1 was used instead of (6-chloro-4-(isopropylamino)-3-pyridyl)cyclopropylmethanone. ¹H-NMR (CDCl₃, 400 MHz) δ 9.31 (s, 1H), 8.88 (s, 1H), 8.65 (s, 1H), 8.45 (s, 2H), 7.54 (s, 1H), 7.36 (d, 1H), 7.12 (s, 1H), 5.89 (t, 1H), 3.42-3.36 (m, 2H), 2.86-2.79 (m, 1H), 2.65-2.60 (m, 1H), 2.03-1.91 (m, 2H), 1.55-1.52 (m, 2H), 1.26-1.21 (m, 4H), 1.14-1.13 (m, 2H), 1.05-1.01 (m, 2H)

Example 6. Cyclopropyl(6-((2-(1-(cyclopropylsulfonyl)-1H-pyrazol-4-yl)pyrimidin-4-yl)amino)-4-((2-(tetrahydrofuran-3-yl)ethyl)amino)pyridin-3-yl)methanone Step 1. (6-Chloro-4-(2-tetrahydrofuran-3-ylethylamino)-3-pyridyl)cyclopropylmethanone The title compound as a solid (181 mg) was prepared in the same fashion as Step 1 in Example 1 except that 2-tetrahydrofuran-3-ylethanamine (117 mg, 1.100 mmol) was used instead of isopropylamine. MS (ESI) m/z=295.1 (M+H)⁺

Step 2. Cyclopropyl(6-((2-(1-(cyclopropylsulfonyl)-1H-pyrazol-4-yl)pyrimidin-4-yl)amino)-4-((2-(tetrahydrofuran-3-yl)ethyl)amino)pyridin-3-yl)methanone The title compound (3 mg) was prepared in the same fashion as Step 2 in Example 1, except that (6-chloro-4-(2-tetrahydrofuran-3-ylethylamino)-3-pyridyl)cyclopropylmethanone (50 mg, 0.17 mmol) prepared in Step 1 was used instead of (6-chloro-4-(isopropylamino)-3-pyridyl)cyclopropylmethanone. ¹H-NMR (CDCl₃, 400 MHz) δ 9.28 (s, 1H), 8.87 (s, 1H), 8.65 (s, 1H), 8.43 (s, 2H), 7.80 (s, 1H), 7.36 (d, 1H), 7.11 (d, 1H), 3.98-3.73 (m, 3H), 3.43-3.32 (m, 4H), 2.84-2.81 (m, 1H), 2.69-2.61 (m, 1H), 2.40-2.33 (m, 1H), 2.13-2.09 (m, 2H), 1.86-1.80 (m, 2H), 1.62-1.55 (m, 2H), 1.25-1.20 (m, 4H), 1.04-0.99 (m, 2H)

Example 7. (R)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone Step 1. (R)-(6-Chloro-4-((4-hydroxybutan-2-yl)amino)pyridin-3-yl)(cyclopropyl)methanone The title compound as a solid (220 mg) was prepared in the same fashion as Step 1 in Example 1 except that (3R)-3-aminobutan-1-ol (91 mg, 1.018 mmol) was used instead of isopropylamine. MS (ESI) m/z=269.1 (M+H)⁺

Step 2. (R)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone The title compound (3 mg) was prepared in the same fashion as Step 2 in Example 1, except that (R)-(6-chloro-4-((4-hydroxybutan-2-yl)amino)pyridin-3-yl)(cyclopropyl)methanone (50 mg, 0.186 mmol) prepared in Step 1 was used instead of (6-chloro-4-(isopropylamino)-3-pyridyl)cyclopropylmethanone. ¹H-NMR (CDCl₃, 400 MHz) δ 9.29 (d, 1H), 8.82 (s, 1H), 8.68 (s, 1H), 8.46 (s, 1H), 8.39 (s, 1H), 7.71 (s, 1H), 7.44 (d, 1H), 6.78 (s, 1H), 4.07-3.99 (m, 1H), 3.80 (s, 2H), 2.87-2.82 (m, 1H), 2.60-2.54 (m, 1H), 1.97-1.82 (m, 2H), 1.56-1.51 (m, 2H), 1.35 (d, 3H), 1.28-1.19 (m, 2H), 1.04-0.99 (m, 2H)

Example 8. (S)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone Step 1. (6-Chloro-4-(((1S)-3-hydroxy-1-methylpropyl)amino)-3-pyridyl)cyclopropylmethanone The title compound as a solid (220 mg) was prepared in the same fashion as Step 1 in Example 1 except that (3S)-3-aminobutan-1-ol (91 mg, 1.018 mmol) was used instead of isopropylamine. MS (ESI) m/z=269.1 (M+H)⁺

Step 2. (S)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone The title compound (5 mg) was prepared in the same fashion as Step 2 in Example 1, except that (6-chloro-4-(((1S)-3-hydroxy-1-methylpropyl)amino)-3-pyridyl)cyclopropylmethanone (50 mg, 0.186 mmol) prepared in Step 1 was used instead of (6-chloro-4-(isopropylamino)-3-pyridyl)cyclopropylmethanone. ¹H-NMR (CDCl₃, 400 MHz) δ 9.30 (d, 1H), 8.81 (s, 1H), 8.67 (s, 1H), 8.45 (s, 1H), 8.37 (s, 1H), 7.79 (s, 1H), 7.46 (s, 1H), 6.95 (s, 1H), 4.07-4.00 (m, 1H), 3.81 (s, 2H), 2.89-2.82 (m, 1H), 2.61-2.54 (m, 1H), 1.99-1.92 (m, 1H), 1.89-1.82 (m, 1H), 1.56-1.51 (m, 2H), 1.35 (d, 3H), 1.23-1.18 (m, 4H), 1.01-0.99 (m, 2H)

Example 9. Cyclopropyl(6-((2-(1-(cyclopropylsulfonyl)-1H-pyrazol-4-yl)pyrimidin-4-yl)amino)-4-((3-hydroxypropyl)amino)pyridin-3-yl)methanone Step 1. (6-Chloro-4-(3-hydroxypropylamino)-3-pyridyl)cyclopropylmethanone The title compound as a solid (204 mg) was prepared in the same fashion as Step 1 in Example 1 except that 3-amino-1-propanol (76.5 mg, 1.018 mmol) was used instead of isopropylamine. MS (ESI) m/z=255.0 (M+H)⁺

Step 2. Cyclopropyl(6-((2-(1-(cyclopropylsulfonyl)-1H-pyrazol-4-yl)pyrimidin-4-yl)amino)-4-((3-hydroxypropyl)amino)pyridin-3-yl)methanone The title compound (1 mg) was prepared in the same fashion as Step 2 in Example 1, except that (6-chloro-4-(3-hydroxypropylamino)-3-pyridyl)cyclopropylmethanone (50 mg, 0.196 mmol) prepared in Step 1 was used instead of (6-chloro-4-(isopropylamino)-3-pyridyl)cyclopropylmethanone. ¹H-NMR (CDCl₃, 400 MHz) δ 9.30 (s, 1H), 8.83 (s, 1H), 8.67 (s, 1H), 8.47 (s, 1H), 8.42 (s, 1H), 7.72 (s, 1H), 7.43 (s, 1H), 6.99 (s, 1H), 3.85 (t, 2H), 3.48 (t, 2H), 2.88-2.81 (m, 1H), 2.61-2.55 (m, 1H), 2.04-2.01 (m, 2H), 1.56-1.51 (m, 2H), 1.24-1.19 (m, 4H), 1.02-0.99 (m, 2H)

Example 10. Cyclopropyl(6-((2-(1-(cyclopropylsulfonyl)-1H-pyrazol-4-yl)pyrimidin-4-yl)amino)-4-(((tetrahydro-2H-pyran-2-yl)methyl)amino)pyridin-3-yl)methanone Step 1. (6-Chloro-4-(tetrahydropyran-2-ylmethylamino)-3-pyridyl)cyclopropylmethanone The title compound as a solid (209 mg) was prepared in the same fashion as Step 1 in Example 1 except that 2-(aminomethyl)tetrahydropyran (117 mg, 1.018 mmol) was used instead of isopropylamine. MS (ESI) m/z=295.1 (M+H)⁺

Step 2. Cyclopropyl(6-((2-(1-(cyclopropylsulfonyl)-1H-pyrazol-4-yl)pyrimidin-4-yl)amino)-4-(((tetrahydro-2H-pyran-2-yl)methyl)amino)pyridin-3-yl) methanone The title compound (15 mg) was prepared in the same fashion as Step 2 in Example 1, except that (6-chloro-4-(tetrahydropyran-2-ylmethylamino)-3-pyridyl)cyclopropylmethanone (49 mg, 0.166 mmol) prepared in Step 1 was used instead of (6-chloro-4-(isopropylamino)-3-pyridyl)cyclopropylmethanone. ¹H-NMR (CDCl₃, 400 MHz) δ 9.39 (s, 1H), 8.86 (s, 1H), 8.67 (s, 1H), 8.46 (s, 2H), 7.68 (s, 1H), 7.23 (s, 1H), 7.10 (s, 1H), 4.06-4.03 (m, 1H), 3.65-3.62 (m, 1H), 3.52-3.47 (m, 1H), 3.36-3.30 (m, 2H), 2.86-2.81 (m, 1H), 2.59-2.55 (m, 1H), 1.90-1.88 (m, 1H), 1.67-1.46 (m, 5H), 1.24-1.19 (m, 4H), 1.15-1.13 (m, 2H), 1.02-0.99 (m, 2H); MS (ESI) m/z=524.2 (M+H)⁺

Example 11. (R)-Cyclopropyl(6-((2-(1-(cyclopropylsulfonyl)-1H-pyrazol-4-yl)pyrimidin-4-yl)amino)-4-((3-hydroxybutyl)amino)pyridin-3-yl)methanone Step 1. (6-Chloro-4-(((3R)-3-hydroxybutyl)amino)-3-pyridyl)cyclopropylmethanone The title compound as a solid (191 mg) was prepared in the same fashion as Step 1 in Example 1 except that (2R)-4-aminobutan-2-ol (136 mg, 1.527 mmol) was used instead of isopropylamine. MS (ESI) m/z=269.1 (M+H)⁺

Step 2. (R)-Cyclopropyl(6-((2-(1-(cyclopropylsulfonyl)-1H-pyrazol-4-yl)pyrimidin-4-yl)amino)-4-((3-hydroxybutyl)amino)pyridin-3-yl)methanone The title compound (20 mg) was prepared in the same fashion as Step 2 in Example 1, except that (6-chloro-4-(((3R)-3-hydroxybutyl)amino)-3-pyridyl)cyclopropylmethanone (61 mg, 0.226 mmol) prepared in Step 1 was used instead of (6-chloro-4-(isopropylamino)-3-pyridyl)cyclopropylmethanone. ¹H-NMR (CDCl₃, 400 MHz) δ 9.29 (s, 1H), 8.81 (s, 1H), 8.66 (s, 1H), 8.46 (s, 1H), 8.40 (s, 1H), 7.85 (s, 1H), 7.40 (s, 1H), 6.99 (s, 1H), 4.06-4.01 (m, 1H), 3.50-3.42 (m, 2H), 2.87-2.82 (m, 1H), 2.58-2.55 (m, 1H), 1.89-1.75 (m, 2H), 1.53-1.46 (m, 2H), 1.29 (s, 3H), 1.28-1.13 (m, 4H), 1.02-0.99 (m, 2H); MS (ESI) m/z=498.2 (M+H)⁺

Example 12. Cyclopropyl(6-((2-(1-(cyclopropylsulfonyl)-1H-pyrazol-4-yl)pyrimidin-4-yl)amino)-4-((3-hydroxy-2-methylbutan-2-yl)amino)pyridin-3-yl) methanone Step 1. (6-Chloro-4-((2-hydroxy-1,1-dimethyl-propyl)amino)-3-pyridyl)cyclopropylmethanone The title compound as a solid (127 mg) was prepared in the same fashion as Step 1 in Example 1 except that 3-amino-3-methylbutan-2-ol (158 mg, 1.527 mmol) was used instead of isopropylamine. MS (ESI) m/z=283.1 (M+H)⁺

Step 2. Cyclopropyl(6-((2-(1-(cyclopropylsulfonyl)-1H-pyrazol-4-yl)pyrimidin-4-yl)amino)-4-((3-hydroxy-2-methylbutan-2-yl)amino)pyridin-3-yl) methanone The title compound (33 mg) was prepared in the same fashion as Step 2 in Example 1, except that (6-chloro-4-((2-hydroxy-1,1-dimethyl-propyl)amino)-3-pyridyl)cyclopropylmethanone (64 mg, 0.226 mmol) prepared in Step 1 was used instead of (6-chloro-4-(isopropylamino)-3-pyridyl)cyclopropylmethanone. ¹H-NMR (CDCl₃, 400 MHz) δ 9.81 (s, 1H), 8.88 (s, 1H), 8.72 (s, 1H), 8.48 (s, 1H), 8.45 (s, 1H), 7.30 (s, 1H), 7.24 (s, 2H), 4.08-4.03 (m, 1H), 2.87-2.80 (m, 1H), 2.62-2.56 (m, 1H), 1.69-1.63 (m, 2H), 1.52 (s, 6H), 1.48 (s, 3H), 1.27-1.21 (m, 4H), 1.03-1.00 (m, 2H); MS (ESI) m/z=512.2 (M+H)⁺

Example 13. Cyclopropyl(6-((2-(1-(cyclopropylsulfonyl)-1H-pyrazol-4-yl)pyrimidin-4-yl)amino)-4-((3-(hydroxymethyl)cyclopentyl)amino)pyridin-3-yl) methanone Step 1. (6-Chloro-4-((3-(hydroxymethyl)cyclopentyl)amino)-3-pyridyl)cyclopropylmethanone The title compound as a solid (238 mg) was prepared in the same fashion as Step 1 in Example 1 except that (3-aminocyclopentyl)methanol (176 mg, 1.527 mmol) was used instead of isopropylamine. MS (ESI) m/z=295.1 (M+H)⁺

Step 2. Cyclopropyl(6-((2-(1-(cyclopropylsulfonyl)-1H-pyrazol-4-yl)pyrimidin-4-yl)amino)-4-((3-(hydroxymethyl)cyclopentyl)amino)pyridin-3-yl)methanone The title compound (11.5 mg) was prepared in the same fashion as Step 2 in Example 1, except that (6-chloro-4-((3-(hydroxymethyl)cyclopentyl)amino)-3-pyridyl)cyclopropylmethanone (67 mg, 0.226 mmol) prepared in Step 1 was used instead of (6-chloro-4-(isopropylamino)-3-pyridyl)cyclopropylmethanone. ¹H-NMR (CDCl₃, 400 MHz) δ 9.37 (s, 1H), 8.85 (s, 1H), 8.66 (s, 1H), 8.45 (s, 2H), 7.69 (s, 1H), 7.22 (s, 1H), 7.12 (s, 1H), 4.01-3.97 (m, 1H), 3.63-3.58 (m, 2H), 2.87-2.82 (m, 1H), 2.63-2.55 (m, 1H), 2.46-2.38 (m, 1H), 2.34-2.26 (m, 1H), 2.15-2.09 (m, 1H), 1.94-1.86 (m, 1H), 1.78-1.71 (m, 1H), 1.67-1.53 (m, 3H), 1.43-1.36 (m, 1H), 1.23-1.19 (m, 4H), 1.03-1.00 (m, 2H); MS (ESI) m/z=524.2 (M+H)⁺

Example 14. Cyclopropyl(6-((2-(1-(cyclopropylsulfonyl)-1H-pyrazol-4-yl)pyrimidin-4-yl)amino)-4-((2-(dimethylamino)ethyl)amino)pyridin-3-yl)methanone Step 1. (6-Chloro-4-(2-(dimethylamino)ethylamino)-3-pyridyl)cyclopropylmethanone The title compound as a solid (382 mg) was prepared in the same fashion as Step 1 in Example 1 except that 2-(dimethylamino)ethylamine (224 mg, 2.546 mmol) was used instead of isopropylamine. MS (ESI) m/z=268.1 (M+H)⁺

Step 2. Cyclopropyl(6-((2-(1-(cyclopropylsulfonyl)-1H-pyrazol-4-yl)pyrimidin-4-yl)amino)-4-((2-(dimethylamino)ethyl)amino)pyridin-3-yl)methanone The title compound (43 mg) was prepared in the same fashion as Step 2 in Example 1, except that (6-chloro-4-(2-

(dimethylamino)ethylamino)-3-pyridyl)cyclopropylmethanone (91 mg, 0.339 mmol) prepared in Step 1 was used instead of (6-chloro-4-(isopropylamino)-3-pyridyl)cyclopropylmethanone. $^1$H-NMR (CDCl$_3$, 400 MHz) δ 9.32 (s, 1H), 8.86 (s, 1H), 8.66 (s, 1H), 8.45 (s, 2H), 7.70 (s, 1H), 7.19 (s, 1H), 7.16 (s, 1H), 3.38-3.35 (m, 2H), 2.86-2.81 (m, 1H), 2.68-2.65 (m, 2H), 2.61-2.56 (m, 1H), 2.31 (s, 6H), 1.54-1.51 (m, 2H), 1.25-1.22 (m, 4H), 1.00-0.98 (m, 2H); MS (ESI) m/z=497.2 (M+H)$^+$ Example 15. Cyclopropyl(6-((2-(1-(cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)methanone Step 1. (6-Chloro-4-((((1r,4r)-4-(hydroxymethyl)cyclohexyl)methyl)amino)pyridin-3-yl)(cyclopropyl)methanone The title compound as a solid (618 mg) was prepared in the same fashion as Step 1 in Example 1 except that ((1r,4r)-4-(aminomethyl)cyclohexyl)methanol HCl (457 mg, 2.546 mmol) was used instead of isopropylamine. $^1$H-NMR (CDCl$_3$, 400 MHz) δ 9.26 (s, 1H), 8.84 (s, 1H), 6.57 (s, 1H), 3.49 (m, 2H), 3.05 (m, 2H), 2.60 (m, 1H), 1.89 (m, 4H), 1.50 (m, 1H), 1.36 (m, 1H) 1.22 (m, 2H), 1.06 (m, 6H); MS (ESI) m/z=323.2 (M+H)$^+$ Step 2. Cyclopropyl(6-((2-(1-(cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)methanone The suspension of 2-(1-(cyclopropylsulfonyl)-1H-pyrazol-4-yl)pyrimidin-4-amine (100 mg, 0.377 mmol), tris(dibenzylideneacetone)dipalladium(0) (17 mg, 0.019 mmol), Xphos (18 mg, 0.038 mmol), cesium carbonate (307 mg, 0.942 mmol) and (6-chloro-4-((((1r,4r)-4-(hydroxymethyl)cyclohexyl)methyl)amino)pyridin-3-yl)(cyclopropyl)methanone (146 mg, 0.452 mmol) prepared in Step 1 in 1,4-dioxane (1.5 mL) was stirred at 110° C. overnight. The mixture was diluted in DCM, filtered through Celite, and then concentrated. The crude product was crystallised by EA/Hex and triturated with EA/isopropyl ether to yield cyclopropyl(6-((2-(1-(cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)methanone (22 mg) as an off-white solid. $^1$H-NMR (CDCl$_3$, 400 MHz) δ 9.32 (s, 1H), 8.86 (s, 1H), 8.67 (s, 1H), 8.45 (s, 2H), 7.62 (s, 1H), 7.26 (s, 1H), 7.06 (s, 1H), 3.49-3.46 (m, 2H), 3.17-3.13 (m, 2H), 2.85-2.80 (m, 1H), 2.63-2.58 (m, 1H), 1.96-1.84 (m, 5H), 1.54-1.49 (m, 3H), 1.26-1.21 (m, 6H), 1.15-1.09 (m, 2H), 1.06-1.00 (m, 2H); MS (ESI) m/z=552.2 (M+H)$^+$ Example 16. Cyclopropyl(6-((2-(1-(difluoromethyl)-1H-pyrazol-4-yl)pyrimidin-4-yl)amino)-4-((4-((dimethylamino)methyl)benzyl)amino)pyridin-3-yl)methanone Step 1. (6-Chloro-4-((4-((dimethylamino)methyl)benzyl)amino)pyridin-3-yl)(cyclopropyl)methanone The title compound as a solid (338 mg) was prepared in the same fashion as Step 1 in Example 1 except that (4-((dimethylamino)methyl)phenyl)methanamine (251 mg, 1.527 mmol) was used instead of isopropylamine. $^1$H-NMR (CDCl$_3$, 400 MHz) δ 9.50 (s, 1H), 8.87 (s, 1H), 7.32-7.24 (m, 4H), 6.58 (s, 1H), 4.40 (d, 1H), 3.42 (s, 2H), 2.64-2.57 (m, 1H), 2.25 (s, 6H), 1.23-1.21 (m, 2H), 1.08-1.04 (m, 2H)

Step 2. Cyclopropyl(6-((2-(1-(difluoromethyl)-1H-pyrazol-4-yl)pyrimidin-4-yl)amino)-4-((4-((dimethylamino)methyl)benzyl)amino)pyridin-3-yl)methanone The title compound (42 mg) was prepared in the same fashion as Step 2 in Reference Example 1, except that (6-chloro-4-((4-((dimethylamino)methyl)benzyl)amino)pyridin-3-yl)(cyclopropyl)methanone (100 mg, 0.291 mmol) prepared in Step 1 and 2-(1-(difluoromethyl)-1H-pyrazol-4-yl)pyrimidin-4-amine (68 mg, 0.320 mmol) were used instead of 4-((2-chloro-5-(cyclopropanecarbonyl)-4-pyridyl)amino)cyclohexanone and 2-(1-(cyclopropylsulfonyl)-1H-pyrazol-4-yl)pyrimidin-4-amine. $^1$H-NMR (CDCl$_3$, 400 MHz) δ 9.62 (t, 1H), 8.90 (s, 1H), 8.48 (s, 1H), 8.41 (d, 1H), 8.25 (s, 1H), 7.93 (s, 1H), 7.30 (s, 4H), 7.20 (t, 1H), 7.18 (d, 1H), 7.01 (s, 1H), 4.51 (d, 2H), 3.42 (s, 2H), 2.65-2.59 (m, 1H), 2.24 (s, 6H), 1.23-1.19 (m, 2H), 1.05-1.00 (m, 2H).

Example 17. Cyclopropyl(6-((2-(1-(cyclopropylsulfonyl)-1H-pyrazol-4-yl)pyrimidin-4-yl)amino)-4-(((1-(2-fluoroethyl)-1H-pyrazol-4-yl)methyl)amino)pyridin-3-yl)methanone Step 1. (6-Chloro-4-(((1-(2-fluoroethyl)-1H-pyrazol-4-yl)methyl)amino)pyridin-3-yl)(cyclopropyl)methanone The title compound as a solid (243 mg) was prepared in the same fashion as Step 1 in Example 1 except that (1-(2-fluoroethyl)pyrazol-4-yl)methanamine (166 mg, 1.157 mmol) was used instead of isopropylamine. $^1$H-NMR (CDCl$_3$, 400 MHz) δ 9.28 (s, 1H), 8.85 (s, 1H), 7.52 (s, 1H), 7.46 (s, 1H), 6.63 (s, 1H), 4.82 (t, 1H), 4.70 (t, 1H), 4.43 (t, 1H), 4.36 (t, 1H), 4.27 (d, 2H), 2.62-2.55 (m, 1H), 1.21-1.17 (m, 2H), 1.07-1.02 (m, 2H)

Step 2. Cyclopropyl(6-((2-(1-(cyclopropylsulfonyl)-1H-pyrazol-4-yl)pyrimidin-4-yl)amino)-4-(((1-(2-fluoroethyl)-1H-pyrazol-4-yl)methyl)amino)pyridin-3-yl)methanone The title compound (6 mg) was prepared in the same fashion as Step 2 in Reference Example 1, except that (6-chloro-4-(((1-(2-fluoroethyl)-1H-pyrazol-4-yl)methyl)amino)pyridin-3-yl)(cyclopropyl)methanone (61 mg, 0.188 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.42 (s, 1H), 8.90 (s, 1H), 8.67 (s, 1H), 8.47 (d, 1H), 8.42 (s, 1H), 7.62 (s, 1H), 7.58 (s, 1H), 7.54 (s, 1H), 7.26 (s, 1H), 7.17 (d, 1H), 4.84-4.80 (m, 1H), 4.71-4.68 (m, 1H), 4.44-4.41 (m, 3H), 4.38-4.35 (m, 1H), 2.82-2.76 (m, 1H), 2.64-2.59 (m, 1H), 1.50-1.48 (m, 2H), 1.22-1.19 (m, 4H), 1.04-1.00 (m, 2H)

Example 18. Cyclopropyl(4-(((1-(cyclopropylmethyl)piperidin-4-yl)methyl)amino)-6-((2-(1-(cyclopropylsulfonyl)-1H-pyrazol-4-yl)pyrimidin-4-yl)amino)pyridin-3-yl)methanone Step 1. (6-Chloro-4-(((1-(cyclopropylmethyl)piperidin-4-yl)methyl)amino)pyridin-3-yl)(cyclopropyl)methanone The title compound as a solid (279 mg) was prepared in the same fashion as Step 1 in Example 1 except that (1-(cyclopropylmethyl)-4-piperidyl)methanamine (195 mg, 1.157 mmol) was used instead of isopropylamine. $^1$H-NMR (CDCl$_3$, 400 MHz) δ 9.26 (s, 1H), 8.83 (s, 1H), 6.57 (s, 1H), 3.12-3.06 (m, 3H), 2.61-2.57 (m, 1H), 2.25 (d, 2H), 1.96 (t, 2H), 1.80 (d, 2H), 1.65-1.61 (m, 1H), 1.44-1.37 (m, 2H), 1.12-1.19 (m, 2H), 1.07-1.02 (m, 2H), 0.88-0.85 (m, 1H), 0.54-0.49 (m, 2H), 0.12-0.08 (m, 2H)

Step 2. Cyclopropyl(4-(((1-(cyclopropylmethyl)piperidin-4-yl)methyl)amino)-6-((2-(1-(cyclopropylsulfonyl)-1H-pyrazol-4-yl)pyrimidin-4-yl)amino)pyridin-3-yl)methanone The title compound (12 mg) was prepared in the same fashion as Step 2 in Reference Example 1, except that (6-chloro-4-(((1-(cyclopropylmethyl)piperidin-4-yl)methyl)amino)pyridin-3-yl)(cyclopropyl)methanone (66 mg, 0.188 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.34 (s, 1H), 8.89 (s, 1H), 8.68 (s, 1H), 8.48 (d, 1H), 8.45 (s, 1H), 7.56 (s, 1H), 7.35 (d, 1H), 6.98 (s, 1H), 3.21-3.18 (m, 2H), 3.15-3.12 (m, 2H), 2.88-2.82 (m, 1H), 2.65-2.60 (m, 1H), 2.28-2.26 (m, 2H), 2.03-1.97 (m, 2H), 1.87-1.83 (m, 2H), 1.73-1.67 (m, 1H), 1.56-1.51 (m, 2H), 1.51-1.43 (m, 2H), 1.26-1.21 (m, 4H), 1.05-1.00 (m, 2H), 0.90-0.86 (m, 1H), 0.54-0.52 (m, 2H), 0.12-0.11 (m, 2H)

Example 19. Cyclopropyl(6-((2-(1-(cyclopropylsulfonyl)-1H-pyrazol-4-yl)pyrimidin-4-yl)amino)-4-(((6-((dimethylamino)methyl)pyridin-3-yl)methyl)amino)pyridin-3-yl)methanone

Step 1. (6-Chloro-4-(((6-((dimethylamino)methyl)pyridin-3-yl)methyl)amino)pyridin-3-yl)(cyclopropyl)methanone The title compound as a solid (240 mg) was prepared in the same fashion as Step 1 in Example 1 except that (6-((dimethylamino)methyl)-3-pyridyl)methanamine (210 mg, 1.273 mmol) was used instead of isopropylamine. $^1$H-NMR (CDCl$_3$, 400 MHz) δ 9.53 (s, 1H), 8.88 (s, 1H), 8.54 (d, 1H), 7.61 (dd, 1H), 7.42 (d, 1H), 6.57 (s, 1H), 4.43-4.42 (m, 2H), 3.61 (s, 2H), 2.64-2.58 (m, 1H), 2.31 (s, 6H), 1.24-1.20 (m, 2H), 1.09-1.05 (m, 2H)

Step 2. Cyclopropyl(6-((2-(1-(cyclopropylsulfonyl)-1H-pyrazol-4-yl)pyrimidin-4-yl)amino)-4-(((6-((dimethylamino)methyl)pyridin-3-yl)methyl)amino)pyridin-3-yl)methanone The title compound (18 mg) was prepared in the same fashion as Step 2 in Reference Example 1, except that (6-chloro-4-(((6-((dimethylamino)methyl)pyridin-3-yl)methyl)amino)pyridin-3-yl)(cyclopropyl)methanone (50 mg, 0.145 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.62 (s, 1H), 8.93 (s, 1H), 8.66 (s, 1H), 8.58 (d, 1H), 8.46 (d, 1H), 8.41 (s, 1H), 7.67 (t, 2H), 7.40 (d, 1H), 7.31 (d, 1H), 6.99 (s, 1H), 4.53 (d, 2H), 3.60 (s, 2H), 2.84-2.81 (m, 1H), 2.66-2.61 (m, 1H), 2.30 (s, 1H), 1.51-1.48 (m, 2H), 1.27-1.20 (m, 4H), 1.06-1.03 (m, 2H)

Example 20. Cyclopropyl(6-((2-(1-(cyclopropylsulfonyl)-1H-pyrazol-4-yl)pyrimidin-4-yl)amino)-4-(((5-((dimethylamino)methyl)thiophen-2-yl)methyl)amino)pyridin-3-yl)methanone

Step 1. (6-Chloro-4-(((5-((dimethylamino)methyl)thiophen-2-yl)methyl)amino)pyridin-3-yl)(cyclopropyl)methanone The title compound as a solid (196 mg) was prepared in the same fashion as Step 1 in Example 1 except that 1-(5-(aminomethyl)thiophen-2-yl)-N,N-dimethylmethanamine (189 mg, 1.111 mmol) was used instead of isopropylamine. MS (ESI) m/z=350.1 (M+H)$^+$

Step 2. Cyclopropyl(6-((2-(1-(cyclopropylsulfonyl)-1H-pyrazol-4-yl)pyrimidin-4-yl)amino)-4-(((5-((dimethylamino)methyl)thiophen-2-yl)methyl)amino)pyridin-3-yl)methanone The title compound (13 mg) was prepared in the same fashion as Step 2 in Reference Example 1, except that (6-chloro-4-(((5-((dimethylamino)methyl)thiophen-2-yl)methyl)amino)pyridin-3-yl)(cyclopropyl)methanone (66 mg, 0.188 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.61 (t, 1H), 8.91 (s, 1H), 8.67 (s, 1H), 8.46 (d, 1H), 8.41 (s, 1H), 7.54 (s, 1H), 7.35 (d, 1H), 6.95 (s, 1H), 6.87 (d, 1H), 6.75 (d, 1H), 4.63 (d, 2H), 3.56 (s, 2H), 2.84-2.78 (m, 1H), 2.65-2.59 (m, 1H), 2.25 (s, 6H), 1.53-1.48 (m, 2H), 1.22-1.18 (m, 4H), 1.04-1.00 (m, 2H)

Example 21. Cyclopropyl(6-((2-(1-(cyclopropylsulfonyl)-1H-pyrazol-4-yl)pyrimidin-4-yl)amino)-4-((2-(4-(dimethylamino)piperidin-1-yl)ethyl)amino)pyridin-3-yl)methanone

Step 1. (6-Chloro-4-(2-(4-(dimethylamino)-1-piperidyl)ethylamino)-3-pyridyl)cyclopropylmethanone The title compound as a solid (205 mg) was prepared in the same fashion as Step 1 in Example 1 except that 1-(2-aminoethyl)-N,N-dimethylpiperidin-4-amine (190 mg, 1.111 mmol) was used instead of isopropylamine. MS (ESI) m/z=351.1 (M+H)$^+$

Step 2. Cyclopropyl(6-((2-(1-(cyclopropylsulfonyl)-1H-pyrazol-4-yl)pyrimidin-4-yl)amino)-4-((2-(4-(dimethylamino)piperidin-1-yl)ethyl)amino)pyridin-3-yl)methanone The title compound (18 mg) was prepared in the same fashion as Step 2 in Reference Example 1, except that (6-chloro-4-(2-(4-(dimethylamino)-1-piperidyl)ethylamino)-3-pyridyl)cyclopropylmethanone (66 mg, 0.188 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.38 (t, 1H), 8.86 (s, 1H), 8.67 (s, 1H), 8.45 (d, 2H), 7.65 (s, 1H), 7.17 (d, 2H), 3.39 (dd, 2H), 2.99 (d, 2H), 2.84-2.78 (m, 1H), 2.72 (t, 2H), 2.63-2.59 (m, 1H), 2.29 (s, 6H), 2.10-2.05 (m, 3H), 1.82-1.79 (m, 2H), 1.61-1.53 (m, 4H), 1.29-1.19 (m, 4H), 1.01-0.97 (m, 2H)

Example 22. Cyclopropyl(6-((2-(1-(cyclopropylsulfonyl)-1H-pyrazol-4-yl)pyrimidin-4-yl)amino)-4-(((1S,3S)-3-hydroxycyclohexyl)amino)pyridin-3-yl)methanone Step 1. (6-Chloro-4-(((1S,3S)-3-hydroxycyclohexyl)amino)pyridin-3-yl)(cyclopropyl)methanone The title compound as a solid (191 mg) was prepared in the same fashion as Step 1 in Example 1 except that (1S,3S)-3-aminocyclohexanol HCl (168 mg, 1.111 mmol) was used instead of isopropylamine. MS (ESI) m/z=295.1 (M+H)$^+$ Step 2. Cyclopropyl(6-((2-(1-(cyclopropylsulfonyl)-1H-pyrazol-4-yl)pyrimidin-4-yl)amino)-4-(((1S,3S)-3-hydroxycyclohexyl)amino)pyridin-3-yl)methanone The title compound (13 mg) was prepared in the same fashion as Step 2 in Reference Example 1, except that (6-chloro-4-(((1S,3S)-3-hydroxycyclohexyl)amino)pyridin-3-yl)(cyclopropyl)methanone (56 mg, 0.188 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.41 (d, 1H), 8.87 (s, 1H), 8.67 (s, 1H), 8.50 (s, 1H), 8.45 (d, 1H), 7.62 (s, 1H), 7.17 (d, 2H), 4.14-4.10 (m, 1H), 4.05-4.00 (m, 1H), 2.89-2.82 (m, 1H), 2.63-2.57 (m, 1H), 2.02-1.91 (m, 2H), 1.85-1.73 (m, 4H), 1.56-1.52 (m, 4H), 1.23-1.18 (m, 4H), 1.03-0.99 (m, 2H); MS (ESI) m/z=524.2 (M+H)$^+$ Example 23. Cyclopropyl(6-((2-(1-(cyclopropylsulfonyl)-1H-pyrazol-4-yl)pyrimidin-4-yl)amino)-4-(((1s,4s)-4-hydroxycyclohexyl)amino)pyridin-3-yl)methanone Step 1. (6-Chloro-4-(((1s,4s)-4-hydroxycyclohexyl)amino)pyridin-3-yl)(cyclopropyl)methanone The title compound as a solid (203 mg) was prepared in the same fashion as Step 1 in Example 1 except that cis-4-aminocyclohexanol HCl (168 mg, 1.111 mmol) was used instead of isopropylamine. MS (ESI) m/z=295.1 (M+H)$^+$ Step 2. Cyclopropyl(6-((2-(1-(cyclopropylsulfonyl)-1H-pyrazol-4-yl)pyrimidin-4-yl)amino)-4-(((1s,4s)-4-hydroxycyclohexyl)amino)pyridin-3-yl)methanone The title compound (13 mg) was prepared in the same fashion as Step 2 in Reference Example 1, except that (6-chloro-4-(((1s,4s)-4-hydroxycyclohexyl)amino)pyridin-3-yl)(cyclopropyl)methanone (56 mg, 0.188 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.58 (d, 1H), 8.88 (s, 1H), 8.64 (s, 1H), 8.45 (t, 2H), 7.67 (brs, 1H), 7.22 (brs, 1H), 7.13 (d, 1H), 3.88-3.84 (m, 1H), 3.73-3.68 (m, 1H), 2.87-2.80 (m, 1H), 2.64-2.57 (m, 1H), 1.96-1.90 (m, 2H), 1.87-1.80 (m, 4H), 1.73-1.65 (m, 2H), 1.56-1.52 (m, 2H), 1.24-1.20 (m, 4H), 1.03-0.99 (m, 2H); MS (ESI) m/z=524.2 (M+H)$^+$ Example 24. Cyclopropyl(6-((2-(1-(cyclopropylsulfonyl)-1H-pyrazol-4-yl)pyrimidin-4-yl)amino)-4-(((1S,3S)-3-hydroxycyclopentyl)amino)pyridin-3-yl)methanone Step 1. (6-Chloro-4-(((1S,3S)-3-hydroxycyclopentyl)amino)-3-pyridyl)cyclopropylmethanone The title compound as a solid (221 mg) was prepared in the same fashion as Step 1 in Example 1 except that (1S,3S)-3-aminocyclopentan-1-ol HCl (153 mg, 1.111 mmol) was used instead of isopropylamine. MS (ESI) m/z=281.1 (M+H)$^+$ Step 2. Cyclopropyl(6-((2-(1-(cyclopropylsulfonyl)-1H-pyrazol-4-yl)pyrimidin-4-yl)amino)-4-(((1S,3S)-3-hydroxycyclopentyl)amino)pyridin-3-yl)methanone The title compound (8 mg) was prepared in the same fashion as Step 2 in Reference Example 1, except that (6-chloro-4-(((1S,3S)-3-hydroxycyclopentyl)amino)-3-pyridyl)cyclopropylmethanone (53 mg, 0.188 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.35 (d, 1H), 8.86 (s, 1H), 8.68 (s, 1H), 8.49 (s, 1H), 8.46 (d, 1H), 7.61 (s, 1H), 7.27 (s, 1H), 7.11 (d, 1H), 4.53-4.48 (m, 1H), 4.31-4.22 (m, 1H), 2.90-2.83 (m, 1H), 2.64-2.57 (m, 1H), 2.46-2.37 (m, 1H), 2.28-2.22 (m, 1H), 2.15-2.06 (m, 1H), 1.89-1.83 (m, 1H), 1.80-1.72 (m, 2H), 1.57-1.53 (m, 2H), 1.24-1.18 (m, 4H), 1.04-0.99 (m, 2H); MS (ESI) m/z=510.2 (M+H)$^+$ Example 25. Cyclopropyl(6-((2-(1-(cyclopropylsulfonyl)-1H-pyrazol-4-yl)pyrimidin-4-yl)amino)-4-(((1S,3R)-3-hydroxycyclopentyl)amino)pyridin-3-yl)methanone Step 1. (6-Chloro-4-(((1S,3R)-3-hydroxycyclopentyl)amino)-3-pyridyl)cyclopropylmethanone The title compound as a solid (259 mg) was prepared in the same fashion as Step 1 in Example 1 except that (1S,3R)-3-aminocyclopentan-1-ol HCl (287 mg, 2.083 mmol) was used instead of isopropylamine. MS (ESI) m/z=281.1 (M+H)$^+$ Step 2. Cyclopropyl(6-((2-(1-(cyclopropylsulfonyl)-1H-pyrazol-4-yl)pyrimidin-4-yl)amino)-4-(((1S,3R)-3-hydroxycyclopentyl)amino)pyridin-3-yl)methanone The title compound (23 mg) was prepared in the same fashion as Step 2 in Reference Example 1, except that (6-chloro-4-(((1S,3R)-3-hydroxycyclopentyl)amino)-3-pyridyl)cyclopropylmethanone (116 mg, 0.415 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.57 (d, 1H), 8.84 (s, 1H), 8.65 (s, 1H), 8.44 (s, 1H), 8.42 (d, 1H), 8.27 (s, 1H), 7.29 (s, 1H), 7.06 (d, 1H), 4.49-4.45 (m, 1H), 4.08-4.03 (m, 1H), 2.86-2.79 (m, 1H), 2.59-2.53 (m, 1H), 2.37-2.30 (m, 1H), 2.21-2.15 (m, 2H), 2.02-1.78 (m, 3H), 1.54-1.49 (m, 2H), 1.23-1.17 (m, 4H), 0.99-0.95 (m, 2H); MS (ESI) m/z=510.2 (M+H)$^+$ Example 26. Cyclopropyl(6-((2-(1-(cyclopropylsulfonyl)-1H-pyrazol-4-yl)pyrimidin-4-yl)amino)-4-(((1R,3R)-3-hydroxycyclopentyl)amino)pyridin-3-yl)methanone Step 1. (6-Chloro-4-(((1R,3R)-3-hydroxycyclopentyl)amino)-3-pyridyl)cyclopropylmethanone The title compound as a solid (323 mg) was prepared in the same fashion as Step 1 in Example 1 except that (1R,3R)-3-aminocyclopentan-1-ol HCl (287 mg, 2.083 mmol) was used instead of isopropylamine. MS (ESI) m/z=281.1 (M+H)$^+$ Step 2. Cyclopropyl(6-((2-(1-(cyclopropylsulfonyl)-1H-pyrazol-4-yl)pyrimidin-4-yl)amino)-4-(((1R,3R)-3-hydroxycyclopentyl)amino)pyridin-3-yl)methanone The title compound (8 mg) was prepared in the same fashion as Step 2 in Reference Example 1, except that (6-chloro-4-(((1R,3R)-3-hydroxycyclopentyl)amino)-3-pyridyl)cyclopropylmethanone (116 mg, 0.415 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.34 (d, 1H), 8.86 (s, 1H), 8.68 (s, 1H), 8.49 (s, 1H), 8.45 (d, 1H), 7.68 (s, 1H), 7.26 (s, 1H), 7.11 (d, 1H), 4.51-4.49 (m, 1H), 4.29-4.24 (m, 1H), 2.89-2.83 (m, 1H), 2.63-2.57 (m, 1H), 2.45-2.36 (m, 1H), 2.27-2.22 (m, 1H), 2.13-2.07 (m, 3H), 1.88-1.82 (m, 1H), 1.78-1.72 (m, 2H), 1.57-1.53 (m, 2H), 1.24-1.18 (m, 4H), 1.03-0.99 (m, 2H)

Example 27. Cyclopropyl(6-((2-(1-(cyclopropylsulfonyl)-1H-pyrazol-4-yl)pyrimidin-4-yl)amino)-4-(((1R,3S)-3-hydroxycyclohexyl)amino)pyridin-3-yl)methanone Step 1. (6-Chloro-4-(((1R,3S)-3-hydroxycyclohexyl)amino)-3-pyridyl)cyclopropylmethanone The title compound as a solid (407.5 mg) was prepared in the same fashion as Step 1 in Example 1 except that (1R,3S)-3-aminocyclohexanol (240 mg, 2.083 mmol) was used instead of isopropylamine. MS (ESI) m/z=295.1 (M+H)$^+$ Step 2. Cyclopropyl(6-((2-(1-(cyclopropylsulfonyl)-1H-pyrazol-4-yl)pyrimidin-4-yl)amino)-4-(((1R,3S)-3-hydroxycyclohexyl)amino)pyridin-3-yl)methanone The title compound (15 mg) was prepared in the same fashion as Step 2 in Reference Example 1, except that (6-chloro-4-(((1R,3S)-3-hydroxycyclohexyl)amino)-3-pyridyl)cyclopropylmethanone (122 mg, 0.415 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.42 (d, 1H), 8.88 (s, 1H), 8.65 (s, 1H), 8.46 (s, 1H), 8.45 (d, 1H), 7.79 (s, 1H), 7.25 (d, 1H), 7.03 (s, 1H), 3.82-3.76 (m, 1H), 3.57-3.49 (m, 1H), 2.86-2.80 (m, 1H), 2.62-2.56 (m, 1H), 2.38-2.35 (m, 1H), 2.05-1.95 (m, 2H), 1.89-1.86 (m, 1H), 1.55-1.51 (m, 2H), 1.45-1.32 (m, 4H), 1.23-1.18 (m, 4H), 1.02-0.97 (m, 2H), 1.03-0.99 (m, 2H)

Example 28. Cyclopropyl(6-((2-(1-(cyclopropylsulfonyl)-1H-pyrazol-4-yl)pyrimidin-4-yl)amino)-4-((3-hydroxy-2,2-dimethylpropyl)amino)pyridin-3-yl)methanone Step 1. (6-Chloro-4-((3-hydroxy-2,2-dimethyl-propyl)amino)-3-pyridyl)cyclopropylmethanone The title compound as a solid (511 mg) was prepared in the same fashion as Step 1 in Example 1 except that 3-amino-2,2-dimethyl-1-propanol (358 mg, 3.471 mmol) was used instead of isopropylamine. MS (ESI) m/z=283.1 (M+H)$^+$ Step 2. Cyclopropyl(6-((2-(1-(cyclopropylsulfonyl)-1H-pyrazol-4-yl)pyrimidin-4-yl)amino)-4-((3-hydroxy-2,2-dimethylpropyl)amino)pyridin-3-yl)methanone The title compound (20 mg) was prepared in the same fashion as Step 2 in Reference Example 1, except that (6-chloro-4-((3-hydroxy-2,2-dimethylpropyl)amino)-3-pyridyl)cyclopropylmethanone (59 mg, 0.207 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.50 (d, 1H), 8.85 (s, 1H), 8.68 (s, 1H), 8.51 (s, 1H), 8.44 (d, 1H), 7.60 (s, 1H), 7.33 (s, 1H), 7.09 (d, 1H), 3.51 (s, 2H), 3.26-3.24 (m, 2H), 2.87-2.81 (m, 1H), 2.64-2.57 (m, 1H), 1.56-1.52 (m, 2H), 1.26-1.20 (m, 4H), 1.07 (s, 6H), 1.05-0.99 (m, 2H), 1.03-0.99 (m, 2H); MS (ESI) m/z=512.2 (M+H)$^+$ Example 29. Cyclopropyl(6-((2-(1-(cyclopropylsulfonyl)-1H-pyrazol-4-yl)pyrimidin-4-yl)amino)-4-((2-(1-hydroxycyclopropyl)ethyl)amino)pyridin-3-yl)methanone Step 1. (6-Chloro-4-(2-(1-hydroxycyclopropyl)ethylamino)-3-pyridyl)cyclopropylmethanone The title compound as a solid (523 mg) was prepared in the same fashion as Step 1 in Example 1 except that 1-(2-aminoethyl)cyclopropan-1-ol (351 mg, 3.471 mmol) was used instead of isopropylamine. MS (ESI) m/z=281.1 (M+H)$^+$ Step 2. Cyclopropyl(6-((2-(1-(cyclopropylsulfonyl)-1H-pyrazol-4-yl)pyrimidin-4-yl)amino)-4-((2-(1-hydroxycyclopropyl)ethyl)amino)pyridin-3-yl)methanone The title compound (8 mg) was prepared in the same fashion as Step 2 in Reference Example 1, except that (6-chloro-4-(2-(1-hydroxycyclopropyl)ethylamino)-3-pyridyl)cyclopropylmethanone (58 mg, 0.207 mmol) prepared in Step 1 was used instead of 4-((2-chloro-5-(cyclopropanecarbonyl)-4-pyridyl)amino)cyclohexanone.
$^1$H-NMR (CDCl$_3$, 400 MHz) δ 9.37 (t, 1H), 8.83 (s, 1H), 8.68 (s, 1H), 8.49 (s, 1H), 8.43 (d, 1H), 7.64 (s, 1H), 7.47 (s, 1H), 6.98 (d, 1H), 3.62-3.48 (m, 2H), 2.86-2.80 (m, 1H), 2.62-2.56 (m, 1H), 2.01 (t, 2H), 1.56-1.52 (m, 2H), 1.26-1.18 (m, 4H), 1.02-0.97 (m, 2H), 0.87-0.84 (m, 2H), 0.61-0.59 (m, 2H); MS (ESI) m/z=510.2 (M+H)$^+$ Example 30. Cyclopropyl(6-((2-(1-(cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)methanone Step 1. (6-Chloro-4-(((1s,4s)-4-(2-hydroxypropan-2-yl)cyclohexyl)amino)-3-pyridyl)(cyclopropyl)methanone The title compound as a solid (331 mg) was prepared in the same fashion as Step 1 in Example 1 except that 2-((1s,4s)-4-aminocyclohexyl)propan-2-ol (237 mg, 1.504 mmol) was used instead of isopropylamine. MS (ESI) m/z=337.1 (M+H)$^+$ Step 2. Cyclopropyl(6-((2-(1-(cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)methanone The title compound (40 mg) was prepared in the same fashion as Step 2 in Reference Example 1, except that (6-chloro-4-(((1s,4s)-4-(2-hydroxypropan-2-yl)cyclohexyl)amino)pyridin-3-yl)(cyclopropyl)methanone (140 mg, 0.415 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.72 (d, 1H), 8.91 (s, 1H), 8.65 (s, 1H), 8.50-8.46 (m, 2H), 7.35 (s, 1H), 7.30 (s, 1H), 7.14 (d, 1H), 4.05-3.99 (m, 1H), 2.85-2.79 (m, 1H), 2.64-2.43 (m, 6H), 2.37-2.29 (m, 2H), 2.10-2.02 (m, 2H), 1.71 (s, 6H), 1.55-1.51 (m, 2H), 1.27-1.21 (m, 4H), 1.06-1.00 (m, 2H)

Example 31. Cyclopropyl(6-((2-(1-(cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)methanone Step 1. (6-Chloro-4-(((1s,4s)-4-((2-fluoroethyl)amino)cyclohexyl)amino)pyridin-3-yl)(cyclopropyl)methanone The title compound as a solid (343 mg) was prepared in the same fashion as Step 1 in Example 1 except that (1s,4s)-N$^1$-(2-fluoroethyl)cyclohexane-1,4-diamine (241 mg, 1.504 mmol) was used instead of isopropylamine. MS (ESI) m/z=340.1 (M+H)$^+$ Step 2. Cyclopropyl(6-((2-(1-(cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)methanone The title compound (5 mg) was prepared in the same fashion as Step 2 in Reference Example 1, except that (6-chloro-4-(((1s,4s)-4-((2-fluoroethyl)amino)cyclohexyl)amino)pyridin-3-yl)(cyclopropyl)methanone (140 mg, 0.415 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.65 (d, 1H), 8.87 (s, 1H), 8.64 (s, 1H), 8.45 (s, 1H), 8.44 (s, 1H), 7.64 (s, 1H), 7.32 (s, 1H), 7.06 (d, 1H), 4.62 (t, 1H), 4.50 (t, 1H), 3.83 (brs, 1H), 2.98 (t, 1H), 2.91 (t, 1H), 2.90-2.87 (m, 1H), 2.81-2.69 (m, 2H), 2.68-2.57 (m, 2H), 2.05-1.97 (m, 2H), 1.84-1.77 (m, 4H), 1.56-1.47 (m, 4H), 1.26-1.21 (m, 4H), 1.03-0.98 (m, 2H)

Example 32. Cyclopropyl-(6-((2-(1-(cyclopropylsulfonyl)-1H-pyrazol-4-yl)pyrimidin-4-yl)amino)-4-(((1s,4s)-4-(methylamino)cyclohexyl)amino)pyridin-3-yl)methanone Step 1 (6-Chloro-4-(((1s,4s)-4-(methylamino)cyclohexyl)amino)pyridin-3-yl)(cyclopropyl)methanone The title compound as a solid (331 mg) was prepared in the same fashion as Step 1 in Example 1 except that (1s,4s)-N$^1$-methylcyclohexane-1,4-diamine (267 mg, 2.083 mmol) was used instead of isopropylamine. MS (ESI) m/z=308.2 (M+H)$^+$ Step 2. Cyclopropyl(6-((2-(1-(cyclopropylsulfonyl)-1H-pyrazol-4-yl)pyrimidin-4-yl)amino)-4-(((1s,4s)-4-(methylamino)cyclohexyl)amino)pyridin-3-yl)methanone The title compound (41 mg) was prepared in the same fashion as Step 2 in Reference Example 1, except (6-chloro-4-(((1s,4s)-4-(methylamino)cyclohexyl)amino)pyridin-3-yl)(cyclopropyl)methanone (116 mg, 0.377 mmol) prepared in Step 1 was used instead of 4-((2-chloro-5-(cyclopropanecarbonyl)-4-pyridyl)amino)cyclohexanone. MS (ESI) m/z=537.2 (M+H)$^+$ Example 33. Cyclopropyl(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)methanone Step 1. (6-Chloro-4-(((1s,4s)-4-hydroxy-4-methylcyclohexyl)amino)pyridin-3-yl)(cyclopropyl)methanone The title compound as a solid (521 mg) was prepared in the same fashion as Step 1 in Example 1 except that cis-4-amino-1-methylcyclohexanol (359 mg, 2.777 mmol) was used instead of isopropylamine. MS (ESI) m/z=309.1 (M+H)$^+$ Step 2. Cyclopropyl(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)methanone The title compound (46 mg) was prepared in the same fashion as Step 2 in Reference Example 1, except (6-chloro-4-(((1s,4s)-4-hydroxy-4-methylcyclohexyl)amino)pyridin-3-yl)(cyclopropyl)methanone (116 mg, 0.377 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.37 (d, 1H), 8.88 (s, 1H), 8.66 (s, 1H), 8.47 (s, 1H), 8.46 (d, 1H), 7.68 (s, 1H), 7.24 (d, 1H), 7.08 (s, 1H), 3.51-3.45 (m, 1H), 2.86-2.79 (m, 1H), 2.63-2.57 (m, 1H), 1.97-1.93 (m, 2H), 1.84-1.71 (m, 4H), 1.62-1.58 (m, 2H), 1.56-1.52 (m, 2H), 1.30 (s, 3H), 1.25-1.18 (m, 4H), 1.03-0.98 (m, 2H); MS (ESI) m/z=538.1 (M+H)$^+$ Example 34. Cyclopropyl(6-((2-(1-(cyclopropylsulfonyl)-1H-pyrazol-4-yl)pyrimidin-4-yl)amino)-4-((tetrahydro-2H-pyran-3-yl)amino)pyridin-3-yl)methanone Step 1. (6-Chloro-4-((tetrahydro-2H-pyran-3-yl)amino)pyridin-3-yl)(cyclopropyl)methanone The reaction mixture of cyclopropyl(4,6-dichloropyridin-3-yl)methanone (300 mg, 1.39 mmol), tetrahydropyran-3-amine HCl (210 mg, 1.53 mmol) and cesium carbonate (905 mg, 2.78 mmol) in DMF (3 mL) was stirred at 80° C. overnight. The reaction mixture was cooled, diluted in EA, washed by water, dried over MgSO$_4$, and then concentrated. The crude product was purified by column chromatography (EA/n-Hex=0-50%) to yield (6-chloro-4-((tetrahydro-2H- pyran-3-yl)amino)pyridin-3-yl)(cyclopropyl)methanone (205.2 mg) as an off-white solid. ¹H-NMR (CDCl₃, 400 MHz) δ 9.30 (s, 1H), 8.78 (s, 1H), 6.54 (s, 1H), 3.81 (m, 1H), 3.68 (m, 1H), 3.49 (m, 2H), 3.35 (m, 1H), 2.54 (m, 1H), 1.95 (m, 1H), 1.63 (m, 1H), 1.61 (m, 2H), 1.14 (m, 2H), 0.97 (m, 2H)

Step 2. Cyclopropyl(6-((2-(1-(cyclopropylsulfonyl)-1H-pyrazol-4-yl)pyrimidin-4-yl)amino)-4-((tetrahydro-2H-pyran-3-yl)amino)pyridin-3-yl)methanone The suspension of 2-(1-(cyclopropylsulfonyl)-1H-pyrazol-4-yl)pyrimidin-4-amine (100 mg, 0.377 mmol), tris(dibenzylideneacetone)dipalladium(0) (34.52 mg, 0.038 mmol), Xantphos (43.62 mg, 0.075 mmol), cesium carbonate (245.64 mg, 0.754 mmol) and (6-chloro-4-((tetrahydro-2H-pyran-3-yl)amino)pyridin-3-yl)(cyclopropyl)methanone (106 mg, 0.377 mmol) prepared in Step 1 in 1,4-dioxane (1.5 mL) was stirred at 110° C. overnight. The mixture was diluted in DCM, filtered through Celite, and then concentrated. The crude product was crystallised by EA/Hex and triturated with EA/isopropyl ether to yield cyclopropyl(6-((2-(1-(cyclopropylsulfonyl)-1H-pyrazol-4-yl)pyrimidin-4-yl)amino)-4-((tetrahydro-2H-pyran-3-yl)amino)pyridin-3-yl)methanone (54 mg) as an off-white solid. ¹H-NMR (DMSO-d₆, 400 MHz) δ 10.30 (m, 1H), 9.01 (s, 1H), 8.64 (s, 1H), 8.45 (m, 2H), 7.45 (m, 3H), 3.83 (m, 1H), 3.69-3.49 (m, 4H), 2.89 (m, 1H), 1.97 (m, 1H), 1.77-1.64 (m, 4H), 1.35 (m, 4H), 1.02 (m, 4H); MS (ESI) m/z=510.0 (M+H)⁺

Example 35. Cyclopropyl(6-((2-(1-(cyclopropylsulfonyl)-1H-pyrazol-4-yl)pyrimidin-4-yl)amino)-4-((tetrahydro-2H-pyran-4-yl)amino)pyridin-3-yl)methanone

Step 1. (6-Chloro-4-((tetrahydro-2H-pyran-4-yl)amino)pyridin-3-yl)(cyclopropyl)methanone The title compound as a solid (221 mg) was prepared in the same fashion as Step 1 in Example 34 except that 4-aminotetrahydropyran (154.5 mg, 1.52 mmol) was used instead of tetrahydropyran-3-amine HCl. ¹H-NMR (CDCl₃, 400 MHz) δ 9.29 (s, 1H), 8.84 (s, 1H), 6.58 (s, 1H), 3.97 (m, 2H), 3.55 (m, 3H), 2.58 (m, 1H), 1.93 (m, 2H), 1.60 (m, 2H), 1.19 (m, 2H), 1.04 (m, 2H); MS (ESI) m/z=281.1 (M+H)⁺

Step 2. Cyclopropyl(6-((2-(1-(cyclopropylsulfonyl)-1H-pyrazol-4-yl)pyrimidin-4-yl)amino)-4-((tetrahydro-2H-pyran-4-yl)amino)pyridin-3-yl)methanone The title compound as an off-white solid (15 mg) was prepared in the same fashion as Step 2 in Example 34 except that (6-chloro-4-((tetrahydro-2H-pyran-4-yl)amino)pyridin-3-yl)(cyclopropyl)methanone (106 mg, 0.377 mmol) prepared in Step 1 was used instead of (6-chloro-4-((tetrahydro-2H-pyran-3-yl)amino)pyridin-3-yl)(cyclopropyl)methanone. ¹H-NMR (DMSO-d₆, 400 MHz) δ 10.28 (s, 1H), 9.28 (m, 1H), 9.01 (m, 1H), 8.67 (s, 1H), 8.47 (m, 1H), 7.53 (s, 1H), 7.36 (m, 1H), 3.81 (m, 2H), 3.73 (m, 1H), 3.72 (m, 2H), 3.25 (m, 1H), 2.90 (m, 1H), 2.00 (m, 2H), 1.49 (m, 2H), 1.47 (m, 2H), 1.26 (m, 1H), 1.04-0.95 (m, 4H); MS (ESI) m/z=510.2 (M+H)⁺

Example 36. Cyclopropyl(6-((2-(1-(cyclopropylsulfonyl)-1H-pyrazol-4-yl)pyrimidin-4-yl)amino)-4-(((3S,4R)-3,4-dihydroxycyclohexyl)amino)pyridin-3-yl)methanone

Step 1. (6-Chloro-4-(((3S,4R)-3,4-dihydroxycyclohexyl)amino)pyridin-3-yl)(cyclopropyl)methanone The title compound as a solid (249 mg) was prepared in the same fashion as Step 1 in Example 1 except that (1R,2S)-4-aminocyclohexane-1,2-diol HCl (256 mg, 1.53 mmol) was used instead of isopropylamine. ¹H-NMR (CDCl₃, 400 MHz) δ 9.49-9.16 (m, 1H), 8.78 (s, 1H), 6.63-6.53 (m, 1H), 4.05 (m, 1H), 3.75 (m, 1H), 3.49 (m, 1H), 3.34 (m, 1H), 3.31 (m, 1H), 2.55 (m, 1H), 2.46 (m, 1H), 2.20 (m, 1H), 1.93 (m, 2H), 1.88-1.78 (m, 3H), 1.73 (m, 1H), 1.01 (m, 2H)

Step 2. Cyclopropyl(6-((2-(1-(cyclopropylsulfonyl)-1H-pyrazol-4-yl)pyrimidin-4-yl)amino)-4-(((3S,4R)-3,4-dihydroxycyclohexyl)amino)pyridin-3-yl)methanone The title compound as an off-white solid (19 mg) was prepared in the same fashion as Step 2 in Example 34 except that (6-chloro-4-(((3S,4R)-3,4-dihydroxycyclohexyl)amino)pyridin-3-yl)(cyclopropyl)methanone (117 mg, 0.377 mmol) prepared in Step 1 was used instead of (6-chloro-4-((tetrahydro-2H-pyran-3-yl)amino)pyridin-3-yl)(cyclopropyl)methanone. ¹H-NMR (DMSO-d₆, 400 MHz) δ 10.25 (m, 1H), 9.35-9.33 (m, 1H), 9.21-8.19 (m, 1H), 8.65 (s, 1H), 8.46 (m, 2H), 7.63-7.52 (m, 1H), 7.33-7.18 (m, 1H), 4.57-5.35 (m, 2H), 3.81-3.56 (m, 3H), 2.87 (m, 2H), 1.96 (m, 2H), 1.72-1.53 (m, 5H), 1.34-1.24 (m, 2H), 0.99-0.93 (m, 5H); MS (ESI) m/z=540.0 (M+H)⁺

Example 37. Cyclopropyl(6-((2-(1-(cyclopropylsulfonyl)-1H-pyrazol-4-yl)pyrimidin-4-yl)amino)-4-((1-(2-(dimethylamino)ethyl)piperidin-4-yl)amino)pyridin-3-yl)methanone

Step 1. (6-Chloro-4-((1-(2-(dimethylamino)ethyl)piperidin-4-yl)amino)pyridin-3-yl)(cyclopropyl)methanone The title compound as a solid (182 mg) was prepared in the same fashion as Step 1 in Example 1 except that 1-(2-(dimethylamino)ethyl)piperidin-4-amine (262 mg, 1.53 mmol) was used instead of isopropylamine. ¹H-NMR (CDCl₃, 400 MHz) δ 9.15-9.13 (m, 1H), 8.71 (s, 1H), 6.44 (s, 1H), 3.41 (m, 1H), 3.29 (m, 1H), 2.73 (m, 2H), 2.47 (m, 1H), 2.39-2.33 (m, 4H), 2.14 (m, 1H), 2.14 (s, 6H), 1.90 (m, 2H), 1.54 (m, 2H), 1.08 (m, 2H), 0.92 (m, 2H)

Step 2. Cyclopropyl(6-((2-(1-(cyclopropylsulfonyl)-1H-pyrazol-4-yl)pyrimidin-4-yl)amino)-4-((1-(2-(dimethylamino)ethyl)piperidin-4-yl)amino)pyridin-3-yl)methanone The title compound as an off-white solid (32 mg) was prepared in the same fashion as Step 2 in Example 34 except that (6-chloro-4-((1-(2-(dimethylamino)ethyl)piperidin-4-yl)amino)pyridin-3-yl)(cyclopropyl)methanone (119 mg, 0.339 mmol) prepared in Step 1 was used instead of (6-chloro-4-((tetrahydro-2H-pyran-3-yl)amino)pyridin-3-yl)(cyclopropyl)methanone. ¹H-NMR (CDCl₃, 400 MHz) δ 9.38 (m, 1H), 8.88 (s, 1H), 8.65 (s, 1H), 8.44 (s, 2H), 7.96

(s, 1H), 7.31 (m, 1H), 6.97 (s, 1H), 3.54 (m, 1H), 2.77 (m, 3H), 2.58 (m, 1H), 2.49-2.33 (m, 4H), 2.33 (m, 2H), 2.25 (s, 6H), 2.20 (m, 1H), 2.08 (m, 1H), 1.71 (m, 2H), 1.53 (m, 2H), 1.19 (m, 4H), 0.99 (m, 2H); MS (ESI) m/z=580.1 (M+H)$^+$

Example 38. Cyclopropyl(6-((2-(1-(cyclopropylsulfonyl)-1H-pyrazol-4-yl)pyrimidin-4-yl)amino)-4-((1-(oxetan-3-yl)piperidin-4-yl)amino)pyridin-3-yl)methanone

Step 1. (6-Chloro-4-((1-(oxetan-3-yl)piperidin-4-yl)amino)pyridin-3-yl)(cyclopropyl)methanone The title compound as a solid (256 mg) was prepared in the same fashion as Step 1 in Example 1 except that 1-(oxetan-3-yl)piperidin-4-amine oxalic acid (376 mg, 1.53 mmol) was used instead of isopropylamine. $^1$H-NMR (CDCl$_3$, 400 MHz) δ 9.22 (s, 1H), 8.77 (s, 1H), 6.50 (d, 1H), 4.61-4.52 (m, 4H), 3.46-3.37 (m, 2H), 2.55-2.52 (m, 3H), 2.05-1.95 (m, 4H), 1.58 (m, 2H), 1.14 (m, 2H), 0.97 (m, 2H)

Step 2. Cyclopropyl(6-((2-(1-(cyclopropylsulfonyl)-1H-pyrazol-4-yl)pyrimidin-4-yl)amino)-4-((1-(oxetan-3-yl)piperidin-4-yl)amino)pyridin-3-yl)methanone The title compound as an off-white solid (39 mg) was prepared in the same fashion as Step 2 in Example 34 except that (6-chloro-4-((1-(oxetan-3-yl)piperidin-4-yl)amino)pyridin-3-yl)(cyclopropyl)methanone (114 mg, 0.339 mmol) prepared in Step 1 was used instead of (6-chloro-4-((tetrahydro-2H-pyran-3-yl)amino)pyridin-3-yl)(cyclopropyl)methanone. $^1$H-NMR (DMSO-d$_6$, 400 MHz) δ 10.27 (s, 1H), 9.27 (s, 1H), 9.00 (s, 1H), 8.66 (s, 1H), 8.48 (m, 2H), 7.49 (s, 1H), 7.36 (s, 1H), 4.51 (m, 2H), 4.41 (m, 2H), 3.58 (m, 1H), 3.39 (m, 1H), 3.26 (m, 2H), 2.89 (m, 1H), 2.07-1.98 (m, 4H), 1.51 (m, 2H), 1.36-1.25 (m, 4H), 1.04 (m, 2H), 1.01 (m, 2H); MS (ESI) m/z=565.1 (M+H)$^+$

Example 39. Cyclopropyl(6-((2-(1-(cyclopropylsulfonyl)-1H-pyrazol-4-yl)pyrimidin-4-yl)amino)-4-((1-(2-fluoroethyl)piperidin-3-yl)amino)pyridin-3-yl)methanone

Step 1. (6-Chloro-4-((1-(2-fluoroethyl)piperidin-3-yl)amino)pyridin-3-yl)(cyclopropyl)methanone The title compound as a solid (296 mg) was prepared in the same fashion as Step 1 in Example 1 except that 1-(2-fluoroethyl)piperidin-3-amine 2HCl (335 mg, 1.53 mmol) was used instead of isopropylamine. $^1$H-NMR (CDCl$_3$, 400 MHz) δ 9.35 (s, 1H), 8.84 (s, 1H), 6.62 (s, 1H), 4.66 (m, 1H), 4.54 (m, 1H), 3.62 (m, 1H), 2.89-2.35 (m, 7H), 1.82 (m, 2H), 1.65 (m, 1H), 1.63 (m, 1H), 1.27 (m, 2H), 1.22 (m, 2H); MS (ESI) m/z=326.1 (M+H)$^+$

Step 2. Cyclopropyl(6-((2-(1-(cyclopropylsulfonyl)-1H-pyrazol-4-yl)pyrimidin-4-yl)amino)-4-((1-(2-fluoroethyl)piperidin-3-yl)amino)pyridin-3-yl)methanone The title compound as an off-white solid (28 mg) was prepared in the same fashion as Step 2 in Example 34 except that (6-chloro-4-((1-(2-fluoroethyl)piperidin-3-yl)amino)pyridin-3-yl)(cyclopropyl)methanone (110.5 mg, 0.339 mmol) prepared in Step 1 was used instead of (6-chloro-4-((tetrahydro-2H-pyran-3-yl)amino)pyridin-3-yl)(cyclopropyl)methanone. $^1$H-NMR (CDCl$_3$, 400 MHz) δ 9.48 (s, 1H), 8.89 (s, 1H), 8.66 (s, 1H), 8.47 (s, 2H), 7.53 (m, 1H), 7.27 (m, 1H), 7.03 (m, 1H), 4.64-4.52 (m, 2H), 3.76 (m, 1H), 2.92-2.58 (m, 8H), 1.64-1.53 (m, 7H), 1.23 (m, 2H), 1.15 (m, 3H), 1.12 (m, 2H); MS (ESI) m/z=555.0 (M+H)$^+$

Example 40. 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2-(tetrahydro-2H-pyran-4-yl)ethan-1-one

Step 1. 1-(6-Chloro-4-(((1s,4s)-4-hydroxy-4-methylcyclohexyl)amino)pyridin-3-yl)-2-(tetrahydro-2H-pyran-4-yl)ethan-1-one The title compound as a solid (110 mg) was prepared in the same fashion as Step 1 in Example 1 except that 1-(4,6-dichloropyridin-3-yl)-2-(tetrahydro-2H-pyran-4-yl)ethan-1-one (159 mg, 0.580 mmol) and cis-4-amino-1-methylcyclohexan-1-ol (50 mg, 0.387 mmol) were used instead of cyclopropyl(4,6-dichloropyridin-3-yl)methanone and isopropylamine. $^1$H-NMR (CDCl$_3$, 400 MHz) δ 9.28 (d, 1H), 8.68 (s, 1H), 6.60 (s, 1H), 3.96-3.92 (m, 1H), 3.44-3.37 (m, 2H), 3.32-3.28 (m, 1H), 2.81 (d, 2H), 2.18-2.11 (m, 1H), 1.88-1.35 (m, 12H), 1.27 (s, 3H); MS (ESI) m/z=367.0 (M+H)$^+$

Step 2. 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2-(tetrahydro-2H-pyran-4-yl)ethan-1-one The title compound as a white solid (6 mg) was prepared in the same fashion as Step 2 in Example 34, except that 1-(6-chloro-4-(((1s,4s)-4-hydroxy-4-methylcyclohexyl)amino)pyridin-3-yl)-2-(tetrahydro-2H-pyran-4-yl)ethan-1-one (28 mg, 0.075 mmol) prepared in Step 1 was used instead of (6-chloro-4-((tetrahydro-2H-pyran-3-yl)amino)pyridin-3-yl)(cyclopropyl)methanone. $^1$H-NMR (CDCl$_3$, 400 MHz) δ 9.43 (d, 1H), 8.65 (s, 2H), 8.45 (d, 2H), 7.88 (brs, 1H), 7.21 (d, 1H), 7.11 (s, 1H), 3.99-3.95 (m, 2H), 3.48-3.40 (m, 3H), 2.86-2.80 (m, 3H), 2.24-2.18 (m, 1H), 1.98-1.93 (m, 2H), 1.84-1.39 (m, 12H), 1.27 (s, 3H), 1.23-1.20 (m, 2H); MS (ESI) m/z=596.2 (M+H)$^+$

Example 41. N$^2$-(2-(1-(Cyclopropylsulfonyl)-1H-pyrazol-4-yl)pyrimidin-4-yl)-5-fluoro-N$^4$-isopropylpyridine-2,4-diamine

Step 1. 2-Chloro-5-fluoro-N-isopropylpyridin-4-amine

The mixture of 2-chloro-5-fluoro-4-iodopyridine (1.00 g, 3.880 mmol), isopropylamine (0.4 mL, 4.660 mmol), palladium(II) acetate (44 mg, 0.190 mmol), Xantphos (225 mg, 0.390 mmol) and cesium carbonate (2.53 g, 7.770 mmol) in 1,4-dioxane (20 mL) was purged with nitrogen for 10 minutes. The reaction mixture was stirred at 110° C. overnight. The reaction mixture was cooled, diluted in EA, washed by water, dried by MgSO$_4$, and then concentrated. The crude product was purified by column chromatography (EA/n-Hex=0-25%) to yield 2-chloro-5-fluoro-N-isopropylpyridin-4-amine (262 mg) as a yellow solid. $^1$H-NMR (CDCl$_3$, 400 MHz) δ 7.86 (d, 1H), 6.52 (d, 1H), 4.40 (m, 1H), 3.63 (m, 1H), 1.27 (d, 6H); MS (ESI) m/z=189.1 (M+H)$^+$

Step 2. N²-(2-(1-(Cyclopropylsulfonyl)-1H-pyrazol-4-yl)pyrimidin-4-yl)-5-fluoro-N⁴-isopropylpyridine-2,4-diamine The title compound as an off-white solid (36 mg) was prepared in the same fashion as Step 2 in Example 34 except that 2-chloro-5-fluoro-N-isopropylpyridin-4-amine (65.5 mg, 0.347 mmol) prepared in Step 1 was used instead of (6-chloro-4-((tetrahydro-2H-pyran-3-yl)amino)pyridin-3-yl)(cyclopropyl)methanone. ¹H-NMR (CDCl$_3$, 400 MHz) δ 8.63 (s, 2H), 8.43 (s, 1H), 8.34 (d, 1H), 7.84 (s, 1H), 7.42 (s, 1H), 6.95 (s, 1H), 4.42 (m, 1H), 3.80 (m, 1H), 2.83 (m, 1H), 1.51 (m, 2H), 1.35 (d, 6H), 1.26-1.20 (m, 2H); MS (ESI) m/z=418.2 (M+H)⁺

Example 42. N-(6-((2-(1-(Cyclopropylsulfonyl)-1H-pyrazol-4-yl)pyrimidin-4-yl)amino)-4-isopropoxypyridin-3-yl)cyclopropanecarboxamide

Step 1. 2-(1-(Cyclopropylsulfonyl)-1H-pyrazol-4-yl)-N-(4-isopropoxy-5-nitropyridin-2-yl)pyrimidin-4-amine The title compound as an off-white solid (1.72 g) was prepared in the same fashion as Step 2 in Example 34 except that 2-chloro-4-isopropoxy-5-nitropyridine (1.50 g, 6.925 mmol) was used instead of (6-chloro-4-((tetrahydro-2H-pyran-3-yl)amino)pyridin-3-yl)(cyclopropyl)methanone. ¹H-NMR (CDCl$_3$, 400 MHz) δ 8.86 (d, 1H), 8.63 (s, 1H), 8.52 (m, 1H), 8.44 (d, 1H), 7.95 (s, 1H), 7.71 (s, 1H), 6.93 (m, 1H), 4.93 (m, 1H), 2.83 (m, 1H), 1.65-1.55 (m, 6H+2H), 1.24 (m, 2H); MS (ESI) m/z=446.1 (M+H)⁺

Step 2. N²-(2-(1-(Cyclopropylsulfonyl)-1H-pyrazol-4-yl)pyrimidin-4-yl)-4-isopropoxypyridine-2,5-diamine The reaction mixture of 2-(1-(cyclopropylsulfonyl)-1H-pyrazol-4-yl)-N-(4-isopropoxy-5-nitropyridin-2-yl)pyrimidin-4-amine (1.72 g, 3.87 mmol) prepared in Step 1, iron powder (1.30 g, 23.22 mmol) and ammonium chloride (0.14 g, 2.71 mmol) in ethanol (96 mL) and water (32 mL) was stirred at 100° C. for 2 hours. The reaction mixture was diluted in DCM and filtered through Celite. The filtrate was washed by water, dried over MgSO$_4$, and then concentrated. The crude product was purified by column chromatography (MeOH/EA=0-10%) and triturated by isopropyl ether/EA to yield N²-(2-(1-(cyclopropylsulfonyl)-1H-pyrazol-4-yl)pyrimidin-4-yl)-4-isopropoxypyridine-2,5-diamine (1.07 g) as pale yellow solid. ¹H-NMR (CDCl$_3$, 400 MHz) δ 8.62 (s, 1H), 8.43 (s, 1H), 8.33 (d, 1H), 7.74 (s, 1H), 7.53 (s, 2H), 6.91 (s, 1H), 4.77 (m, 1H), 3.61 (s, 2H), 2.62 (m, 1H), 1.49 (s, 6H+2H), 1.14 (m, 2H); MS (ESI) m/z=416.2 (M+H)⁺

Step 3. N-(6-((2-(1-(Cyclopropylsulfonyl)-1H-pyrazol-4-yl)pyrimidin-4-yl)amino)-4-isopropoxypyridin-3-yl)cyclopropanecarboxamide O-(7-Azabenzotriazol-1-yl)-N,N,N',N'-tetramethyluronium hexafluorophosphate (30 mg, 0.080 mmol) was added to the suspension of N²-(2-(1-(cyclopropylsulfonyl)-1H-pyrazol-4-yl)pyrimidin-4-yl)-4-isopropoxypyridine-2,5-diamine (30 mg, 0.070 mmol) prepared in Step 2, DIPEA (0.02 mL, 0.090 mmol), and cyclopropanecarboxylic acid (0.01 mL, 0.080 mmol) in MeCN (5 mL) at 0° C. The reaction mixture was stirred overnight while being slowly warmed to room temperature. The reaction was diluted in DCM and quenched by water. The organic layer was dried over MgSO$_4$ and concentrated. The crude product was purified by column chromatography (EA/n-Hex=50-100%) to yield N-(6-((2-(1-(cyclopropylsulfonyl)-1H-pyrazol-4-yl)pyrimidin-4-yl)amino)-4-isopropoxypyridin-3-yl)cyclopropanecarboxamide (33 mg) as off-white solid. ¹H-NMR (CDCl$_3$, 400 MHz) δ 9.18 (s, 1H), 9.11 (brs, 1H), 8.59 (s, 1H), 8.41 (s, 1H), 8.35 (d, 1H), 7.99 (s, 1H), 7.72 (s, 1H), 6.68 (s, 1H), 4.87 (m, 1H), 2.84 (m, 1H), 1.63 (m, 1H), 1.54 (m, 6H+2H), 1.44 (m, 2H), 0.91 (m, 2H), 0.90 (m, 2H); MS (ESI) m/z=484.2 (M+H)⁺

Example 43. (4-((((1r,4r)-4-((1H-Imidazol-1-yl)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone

Step 1. ((1r,4r)-4-(((2-Chloro-5-(cyclopropanecarbonyl)pyridin-4-yl)amino)methyl)cyclohexyl)methyl methanesulfonate To a solution of (6-chloro-4-((((1r,4r)-4-(hydroxymethyl)cyclohexyl)methyl)amino)pyridin-3-yl)(cyclopropyl)methanone (578 mg, 1.700 mmol) prepared in Step 1 in Example 15 in DCM (10 mL) was added triethylamine (0.47 mL, 3.400 mmol) and the reaction mixture was cooled to 0° C. Methanesulfonyl chloride (0.16 mL, 2.040 mmol) was added dropwise to the above cooled solution. The reaction was warmed to room temperature and stirred for additional 1 hour. On completion, reaction mixture was diluted with DCM, washed with water, dried by Na$_2$SO$_4$ and concentrated in-vacuo. The resulting solid was triturated with isopropyl ether to yield ((1r,4r)-4-(((2-chloro-5-(cyclopropanecarbonyl)pyridin-4-yl)amino)methyl)cyclohexyl)methyl methanesulfonate (687 mg) as a white solid. ¹H-NMR (CDCl$_3$, 400 MHz) δ 9.27 (s, 1H), 8.84 (s, 1H), 6.56 (s, 1H), 4.07 (m, 2H), 3.06 (m, 5H), 2.60 (m 1H), 1.92 (m, 4H), 1.80 (m, 1H), 1.62 (s, 2H), 1.22 (m, 2H), 1.08 (m, 6H); MS (ESI) m/z=401.1 (M+H)⁺

Step 2. (4-((((1r,4r)-4-((1H-Imidazol-1-yl)methyl)cyclohexyl)methyl)amino)-6-chloropyridin-3-yl)(cyclopropyl)methanone Sodium hydride, 60% in mineral oil (21 mg, 0.860 mmol) was added to the solution of imidazole (0.04 mL, 0.690 mmol) in DMF (2 mL) at 0° C. and the reaction mixture was stirred for 30 minutes. After ((1r,4r)-4-(((2-chloro-5-(cyclopropanecarbonyl)pyridin-4-yl)amino)methyl)cyclohexyl)methyl methanesulfonate (229 mg, 0.5700 mmol) prepared in Step 1 being added, the reaction mixture was stirred at 70° C. overnight. The reaction mixture was diluted in DCM, washed by water, dried over MgSO$_4$, and then concentrated. The crude product was purified by column chromatography (EA/n-Hex=40-100%, MeOH/EA=0-10%) to yield (4-((((1r,4r)-4-((1H-imidazol-1-yl)methyl)cyclohexyl)methyl)amino)-6-chloropyridin-3-yl)(cyclopropyl)methanone (74 mg) as a white solid. ¹H-NMR (CDCl$_3$, 400 MHz) δ 9.24 (s, 1H), 8.82 (s, 1H), 7.44 (s, 1H), 7.05 (s, 1H), 6.87 (s, 1H), 6.53 (s, 1H), 3.77 (m, 2H), 3.02 (m, 2H), 2.58 (m, 1H), 1.87 (m, 2H), 1.71 (m, 3H), 1.60 (m, 1H), 1.20 (m, 2H), 1.03 (m, 6H); MS (ESI) m/z=373.2 (M+H)⁺

Step 3. (4-(((((1r,4r)-4-((1H-Imidazol-1-yl)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone The title compound as an off-white solid (9 mg) was prepared in the same fashion as Step 2 in Example 34 except that (4-((((1r,4r)-4-((1H-imidazol-1-yl)methyl)cyclohexyl) methyl)amino)-6-chloropyridin-3-yl)(cyclopropyl)methanone (74 mg, 0.198 mmol) prepared in Step 2 was used instead of (6-chloro-4-((tetrahydro-2H-pyran-3-yl)amino) pyridin-3-yl)(cyclopropyl)methanone. $^1$H-NMR (CDCl$_3$, 400 MHz) δ 9.32 (brs, 1H), 8.88 (s, 1H), 8.67 (s, 1H), 8.46 (m, 2H), 7.52 (s, 1H), 7.44 (s, 1H), 7.22 (s, 1H), 7.08 (m, 2H), 6.90 (s, 1H), 3.81 (m, 2H), 3.16 (m, 2H), 2.83 (m, 1H), 2.62 (m, 1H), 2.07 (m, 2H), 1.92 (m, 4H), 1.54 (m, 2H), 1.21 (m, 6H), 1.04 (m, 4H); MS (ESI) m/z=602.2 (M+H)$^+$ Example 44. (4-((((1r,4r)-4-((1H-Pyrazol-1-yl) methyl)cyclohexyl)methyl)amino)-6-((2-(1-(cyclopropylsulfonyl)-1H-pyrazol-4-yl)pyrimidin-4-yl) amino)pyridin-3-yl)(cyclopropyl)methanone Step 1. (4-((((1r,4r)-4-((1H-Pyrazol-1-yl)methyl) cyclohexyl)methyl)amino)-6-chloropyridin-3-yl) (cyclopropyl)methanone The title compound (139 mg) was prepared in the same fashion as Step 2 in Example 43, except that pyrazole (47 mg, 0.685 mmol) was used instead of imidazole. $^1$H-NMR (CDCl$_3$, 400 MHz) δ 9.19 (s, 1H), 8.77 (d, 1H), 7.45 (s, 1H), 7.30 (s, 1H), 6.49 (s, 1H), 6.17 (s, 1H), 3.93 (d, 2H), 2.95 (m, 2H), 2.55 (m, 1H), 1.82 (m, 2H), 1.65-1.55 (m, 3H), 1.19 (m, 3H), 0.98 (m, 6H); MS (ESI) m/z=373.2 (M+H)$^+$ Step 2. (4-((((1r,4r)-4-((1H-Pyrazol-1-yl)methyl) cyclohexyl)methyl)amino)-6-((2-(1-(cyclopropylsulfonyl)-1H-pyrazol-4-yl)pyrimidin-4-yl)amino) pyridin-3-yl)(cyclopropyl)methanone The title compound as an off-white solid (30 mg) was prepared in the same fashion as Step 2 in Example 34 except that (4-((((1r,4r)-4-((1H-pyrazol-1-yl)methyl)cyclohexyl) methyl)amino)-6-chloropyridin-3-yl)(cyclopropyl)methanone (149 mg, 0.400 mmol) prepared in Step 1 was used instead of (6-chloro-4-((tetrahydro-2H-pyran-3-yl)amino) pyridin-3-yl)(cyclopropyl)methanone. $^1$H-NMR (CDCl$_3$, 400 MHz) δ 9.33 (m, 1H), 8.86 (s, 1H), 8.67 (s, 1H), 8.47 (m, 2H), 7.76 (m, 1H), 7.51 (s, 1H), 7.35 (s, 1H), 7.23 (m, 1H), 7.09 (s, 1H), 6.24 (s, 1H), 3.99 (d, 2H), 3.15 (d, 2H), 2.83 (m, 1H), 2.61 (m, 1H), 1.89 (m, 4H), 1.69 (m, 4H), 1.16 (m, 4H), 1.14 (m, 2H), 1.02 (m, 4H); MS (ESI) m/z=602.2 (M+H)$^+$ Example 45. 1-(6-((2-(1-(Cyclopropylsulfonyl)-1H-pyrazol-4-yl)pyrimidin-4-yl)amino)-4-(propylamino) pyridin-3-yl)ethan-1-one Step 1. 1-(6-Chloro-4-(propylamino)-3-pyridyl)ethanone The title compound as an off-white solid (196 mg) was prepared in the same fashion as Step 1 in Example 1, except 1-(4,6-dichloropyridin-3-yl)ethan-1-one (200 mg, 1.052 mmol) and propylamine (68 mg, 1.158 mmol) were used instead of cyclopropyl(4,6-dichloropyridin-3-yl)methanone and isopropylamine. MS (ESI) m/z=213.1 (M+H)$^+$ Step 2. 1-(6-((2-(1-(Cyclopropylsulfonyl)-1H-pyrazol-4-yl)pyrimidin-4-yl)amino)-4-(propylamino) pyridin-3-yl)ethan-1-one The title compound as an off-white solid (14 mg) was prepared in the same fashion as Step 2 in Example 1, except 1-(6-chloro-4-(propylamino)-3-pyridyl)ethanone (50 mg, 0.235 mmol) prepared in Step 1 was used instead of (6-chloro-4-(isopropylamino)-3-pyridyl)cyclopropylmethanone. $^1$H-NMR (CDCl$_3$, 400 MHz) δ 9.25 (d, 1H), 8.66 (s, 1H), 8.61 (s, 1H), 8.46 (s, 1H), 8.44 (d, 1H), 7.44 (s, 1H), 7.15 (d, 1H), 3.30 (q, 2H), 2.85-2.79 (m, 1H), 2.57 (s, 3H), 1.82-1.77 (m, 2H), 1.56-1.52 (m, 2H), 1.26-1.20 (m, 2H), 1.09-1.05 (t, 3H); MS (ESI) m/z=442.2 (M+H)

Example 46. 1-(6-((2-(1-(Cyclopropylsulfonyl)-1H-pyrazol-4-yl)pyrimidin-4-yl)amino)-4-((3-hydroxy-2-methylbutan-2-yl)amino)pyridin-3-yl)ethan-1-one Step 1. 1-(6-Chloro-4-((2-hydroxy-1,1-dimethylpropyl)amino)-3-pyridyl)ethanone The title compound as a solid (608 mg) was prepared in the same fashion as Step 1 in Example 1 except that 1-(4,6-dichloropyridin-3-yl)ethan-1-one (500 mg, 2.631 mmol) and 3-amino-3-methylbutan-2-ol (299 mg, 2.894 mmol) were used instead of cyclopropyl(4,6-dichloropyridin-3-yl)methanone and isopropylamine. MS (ESI) m/z=257.0 (M+H)$^+$ Step 2. 1-(6-((2-(1-(Cyclopropylsulfonyl)-1H-pyrazol-4-yl)pyrimidin-4-yl)amino)-4-((3-hydroxy-2-methylbutan-2-yl)amino)pyridin-3-yl)ethan-1-one The title compound (3 mg) was prepared in the same fashion as Step 2 in Example 1, except that 1-(6-chloro-4-((2-hydroxy-1,1-dimethylpropyl)amino)-3-pyridyl)ethanone (70 mg, 0.271 mmol) prepared in Step 1 was used instead of (6-chloro-4-(isopropylamino)-3-pyridyl)cyclopropylmethanone. $^1$H-NMR (CDCl$_3$, 400 MHz) δ 9.85 (s, 1H), 8.72 (s, 1H), 8.62 (s, 1H), 8.48 (s, 1H), 8.45 (d, 1H), 7.66 (s, 1H), 7.31 (s, 1H), 7.21 (d, 1H), 4.09-4.05 (m, 1H), 2.87-2.80 (m, 1H), 2.58 (s, 3H), 1.53 (s, 6H), 1.49 (s, 3H), 1.30-1.21 (m, 2H), 1.21-1.13 (m, 2H)

Example 47. 1-(6-((2-(1-Cyclopropylsulfonylpyrazol-4-yl)pyrimidin-4-yl)amino)-4-((3-(hydroxymethyl)cyclopentyl)amino)-3-pyridyl)ethanone Step 1. 1-(6-Chloro-4-((3-(hydroxymethyl)cyclopentyl)amino)-3-pyridyl)ethanone The title compound as a solid (671 mg) was prepared in the same fashion as Step 1 in Example 1 except that 1-(4,6-dichloropyridin-3-yl)ethan-1-one (500 mg, 2.631 mmol) and (3-aminocyclopentyl)methanol (333 mg, 2.894 mmol) were used instead of cyclopropyl(4,6-dichloropyridin-3-yl)methanone and isopropylamine. MS (ESI) m/z=269.1 (M+H)$^+$ Step 2. 1-(6-((2-(1-(Cyclopropylsulfonyl)-1H-pyrazol-4-yl)pyrimidin-4-yl)amino)-4-((3-(hydroxymethyl)cyclopentyl)amino)pyridin-3-yl)ethan-1-one The title compound (6.5 mg) was prepared in the same fashion as Step 2 in Example 1, except that 1-(6-chloro-4-((3-(hydroxymethyl)cyclopentyl)amino)-3-pyridyl)ethanone (122 mg, 0.452 mmol) prepared in Step 1 was used instead of (6-chloro-4-(isopropylamino)-3-pyridyl)cyclopropylmethanone. $^1$H-NMR (CDCl$_3$, 400 MHz) δ 9.37 (s, 1H), 8.66 (s, 1H), 8.60 (s, 1H), 8.44 (s, 2H), 7.64 (s, 1H), 7.24 (s, 1H), 7.11 (d, 1H), 4.03-3.99 (m, 1H), 3.65-3.58 (m, 2H), 2.86-2.82 (m, 1H), 2.56 (s, 3H), 2.44-2.38 (m, 1H), 2.35-2.29 (m, 1H), 2.15-2.08 (m, 1H), 1.95-1.88 (m, 1H), 1.80-1.72 (m, 1H), 1.53-1.46 (m, 2H), 1.39-1.31 (m, 1H), 1.30-1.21 (m, 4H)

Example 48. 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2,2-difluoroethan-1-one Step 1. 1-(6-Chloro-4-(((1s,4s)-4-hydroxy-4-methylcyclohexyl)amino)pyridin-3-yl)-2,2-difluoroethan-1-one The title compound as a pale yellow solid (204 mg) was prepared in the same fashion as Step 1 in Example 1 except that 1-(4,6-dichloro-3-pyridyl)-2,2-difluoroethanone (200 mg, 0.89 mmol) and cis-4-amino-1-methylcyclohexan-1-ol (171.5 mg, 1.330 mmol) were used instead of cyclopropyl (4,6-dichloropyridin-3-yl)methanone and isopropylamine. MS (ESI) m/z=319.1 (M+H)$^+$ Step 2. 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2,2-difluoroethan-1-one The title compound (98 mg) was prepared in the same fashion as Step 2 in Reference Example 1, except that 1-(6-chloro-4-(((1s,4s)-4-hydroxy-4-methylcyclohexyl)amino)pyridin-3-yl)-2,2-difluoroethan-1-one (132 mg, 0.415 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.07 (d, 1H), 8.76 (s, 1H), 8.66 (s, 1H), 8.48 (d, 1H), 8.47 (s, 1H), 8.10 (s, 1H), 7.32 (s, 1H), 7.14 (d, 1H), 6.28 (t, 1H), 3.57 (brs, 1H), 2.95-2.80 (m, 1H), 1.99-1.95 (m, 2H), 1.85-1.73 (m, 4H), 1.63-1.52 (m, 4H), 1.30 (s, 3H), 1.24-1.21 (m, 2H); MS (ESI) m/z=548.1 (M+H)$^+$ Example 49. 1-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)-2,2-difluoroethan-1-one Step 1. 1-(6-Chloro-4-(((1s,4s)-4-(hydroxymethyl)cyclohexyl)amino)pyridin-3-yl)-2,2-difluoroethan-1-one The title compound as a pale yellow solid (152 mg) was prepared in the same fashion as Step 1 in Example 1 except that 1-(4,6-dichloro-3-pyridyl)-2,2-difluoroethanone (200 mg, 0.890 mmol) and ((1s,4s)-4-aminocyclohexyl)methanol (171.5 mg, 1.330 mmol) were used instead of cyclopropyl (4,6-dichloropyridin-3-yl)methanone and isopropylamine. MS (ESI) m/z=319.1 (M+H)$^+$ Step 2. 1-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)-2,2-difluoroethan-1-one The title compound (77.5 mg) was prepared in the same fashion as Step 2 in Reference Example 1, except that 1-(6-chloro-4-(((1s,4s)-4-(hydroxymethyl)cyclohexyl)amino)pyridin-3-yl)-2,2-difluoroethan-1-one (132 mg, 0.415 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 9.42 (d, 1H), 8.75 (s, 1H), 8.64 (s, 1H), 8.47 (d, 1H), 8.45 (s, 1H), 8.15 (s, 1H), 7.57 (s, 1H), 6.96 (d, 1H), 6.32 (t, 1H), 4.03-4.01 (m, 1H), 3.52 (d, 2H), 2.86-2.83 (m, 1H), 2.05-2.00 (m, 2H), 1.88-1.69 (m, 6H), 1.57-1.53 (m, 2H), 1.35-1.22 (m, 4H); MS (ESI) m/z=548.1 (M+H)$^+$ Example 50. 1-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-2,2-difluoroethan-1-one Step 1. 1-(6-Chloro-4-(((1s,4s)-4-(2-hydroxypropan-2-yl)cyclohexyl)amino)pyridin-3-yl)-2,2-difluoroethan-1-one The title compound as a pale yellow solid (152 mg) was prepared in the same fashion as Step 1 in Example 1 except that 1-(4,6-dichloro-3-pyridyl)-2,2-difluoroethanone (200 mg, 0.89 mmol) and 2-((1s,4s)-4-aminocyclohexyl)propan-2-ol (209 mg, 1.330 mmol) were used instead of cyclopropyl (4,6-dichloropyridin-3-yl)methanone and isopropylamine. MS (ESI) m/z=347.1 (M+H)$^+$ Step 2. 1-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-2,2-difluoroethan-1-one The title compound (79 mg) was prepared in the same fashion as Step 2 in Reference Example 1, except that 1-(6-Chloro-4-(((1s,4s)-4-(2-hydroxypropan-2-yl)cyclohexyl)amino)pyridin-3-yl)-2,2-difluoroethan-1-one (144 mg, 0.415 mmol) prepared in Step 1 was used instead of 4-((2-chloro-5-(cyclopropanecarbonyl)-4-pyridyl)amino) cyclohexanone. $^1$H-NMR (CDCl$_3$, 400 MHz) δ 9.45 (d, 1H), 8.76 (s, 1H), 8.64 (s, 1H), 8.47 (d, 1H), 8.45 (s, 1H), 7.97 (s, 1H), 7.58 (s, 1H), 6.95 (d, 1H), 6.31 (t, 1H), 4.02 (brs, 1H), 2.88-2.82 (m, 1H), 2.11-2.08 (m, 2H), 1.83-1.81 (m, 4H), 1.57-1.53 (m, 2H), 1.49-1.32 (m, 4H), 1.26 (s, 6H); MS (ESI) m/z=576.1 (M+H)$^+$ Example 51. 1-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)-2,2-difluoroethan-1-one Step 1. 1-(6-Chloro-4-(((1s,4s)-4-((2-fluoroethyl)amino)cyclohexyl)amino)pyridin-3-yl)-2,2-difluoroethan-1-one The title compound as a pale yellow solid (236 mg) was prepared in the same fashion as Step 1 in Example 1 except that 1-(4,6-dichloro-3-pyridyl)-2,2-difluoroethanone (200 mg, 0.89 mmol) and (1s,4s)-N$^1$-(2-fluoroethyl)cyclohexane-1,4-diamine (213 mg, 1.33 mmol) were used instead of cyclopropyl(4,6-dichloropyridin-3-yl)methanone and isopropylamine. MS (ESI) m/z=350.1 (M+H)$^+$ Step 2. 1-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)-2,2-difluoroethan-1-one The title compound (117 mg) was prepared in the same fashion as Step 2 in Reference Example 1, except that 1-(6-chloro-4-(((1s,4s)-4-((2-fluoroethyl)amino)cyclohexyl)amino)pyridin-3-yl)-2,2-difluoroethan-1-one (132 mg, 0.415 mmol) prepared in Step 1 was used instead of 4-((2-chloro-5-(cyclopropanecarbonyl)-4-pyridyl)amino) cyclohexanone. $^1$H-NMR (CDCl$_3$, 400 MHz) δ 9.35 (d, 1H), 8.76 (s, 1H), 8.64 (s, 1H), 8.47 (d, 1H), 8.45 (s, 1H), 7.94 (s, 1H), 7.50 (s, 1H), 7.00 (d, 1H), 6.29 (t, 1H), 4.62 (t, 1H), 4.50 (t, 1H), 3.89 (brs, 1H), 2.99 (t, 1H), 2.92 (t, 1H), 2.86-2.83 (m, 1H), 2.69 (t, 1H), 2.02-2.00 (m, 2H), 1.88-1.82 (m, 4H), 1.57-1.55 (m, 4H), 1.27-1.23 (m, 2H); MS (ESI) m/z=579.2 (M+H)$^+$ Example 52. Cyclopropyl(6-((2-(1-(cyclopropylsulfonyl)-1H-pyrazol-4-yl)pyrimidin-4-yl)amino)-4-((4-((2-hydroxyethyl)amino)cyclohexyl)amino)pyridin-3-yl)methanone The suspension of ethanolamine (57.69 uL, 0.960 mmol) {{99.Reactant volume or quant:row 4}}_XXXXX_, DIPEA (0.33 mL, 1.920 mmol) and 4-((5-(cyclopropanecarbonyl)-2-((2-(1-cyclopropylsulfonylpyrazol-4-yl)pyrimidin-4-yl) amino)-4-pyridyl)amino)cyclohexanone (100 mg, 0.190 mmol) prepared in Reference Example 1{{99.Reactant volume or quant:row 3}}_XXXXX_ in MeOH (10 mL){{99. Solvent volume:row 1}}_XXXXX_ was stirred for 30 minutes, added sodium triacetoxyborohydride (406.33 mg, 1.92 mmol) {{99.Reactant volume or quant:row 2}}_XXXXX_ at 0° C. ice bath, and then the reaction mixture was stirred at 50° C. {{99.Reaction temp:row 1}}_XXXXX_ overnight. The reaction mixture was cooled, added to NaHCO$_3$ soln. and extracted with DCM, washed by water, dried over MgSO$_4$, and then concentrated. The crude product was purified by column chromatography (MeOH/DCM=0-100%) to yield cyclopropyl(6-((2-(1-(cyclopropylsulfonyl)-1H-pyrazol-4-yl)pyrimidin-4-yl)amino)-4-((4-((2-hydroxyethyl)amino)cyclohexyl)amino)pyridin-3-yl)methanone (46 mg) as an off-white solid. MS (ESI) m/z=567.0 (M+H)+ {{99. Stirring time:row 1}}_XXXXX_

Example 53. Cyclopropyl(6-((2-(1-(cyclopropylsulfonyl)-1H-pyrazol-4-yl)pyrimidin-4-yl)amino)-4-((4-((2-(dimethylamino)ethyl)amino)cyclohexyl) amino)pyridin-3-yl)methanone The title compound (36 mg) was prepared in the same fashion as Example 52, except that 2-(dimethylamino)ethylamine (84.5 mg, 0.959 mmol) was used instead of ethanolamine. MS (ESI) m/z=594.0 (M+H)$^+$ Example 54. Cyclopropyl(6-((2-(1-(cyclopropylsulfonyl)-1H-pyrazol-4-yl)pyrimidin-4-yl)amino)-4-((4-((4-methylpiperazin-1-yl)amino)cyclohexyl) amino)pyridin-3-yl)methanone The title compound (22 mg) was prepared in the same fashion as Example 52, except that 1-amino-4-methyl-piperazine (55 mg, 0.479 mmol) was used instead of ethanolamine. MS (ESI) m/z=620.1 (M+H)$^+$ Example 55. Cyclopropyl(6-((2-(1-(cyclopropylsulfonyl)-1H-pyrazol-4-yl)pyrimidin-4-yl)amino)-4-((4-((2-(3-fluoroazetidin-1-yl)ethyl)amino)cyclohexyl)amino)pyridin-3-yl)methanone The title compound (31 mg) was prepared in the same fashion as Example 52, except that 3-fluoroazetidine-1-ethanamine (57 mg, 0.479 mmol) was used instead of ethanolamine. MS (ESI) m/z=625.1 (M+H)$^+$ Example 56. Cyclopropyl(6-((2-(1-(cyclopropylsulfonyl)-1H-pyrazol-4-yl)pyrimidin-4-yl)amino)-4-((4-((2-(piperidin-1-yl)ethyl)amino)cyclohexyl) amino)pyridin-3-yl)methanone The title compound (26 mg) was prepared in the same fashion as Example 52, except that 1-(2-aminoethyl)-piperidine (61.5 mg, 0.479 mmol) was used instead of ethanolamine. MS (ESI) m/z=635.2 (M+H)$^+$ Example 57. Cyclopropyl(6-((2-(1-(cyclopropylsulfonyl)-1H-pyrazol-4-yl)pyrimidin-4-yl)amino)-4-((4-((2-(4-(dimethylamino)piperidin-1-yl)ethyl) amino)cyclohexyl)amino)pyridin-3-yl)methanone The title compound (26 mg) was prepared in the same fashion as Example 52, except that 1-(2-aminoethyl)-N,N-dimethylpiperidin-4-amine (82 mg, 0.479 mmol) was used instead of ethanolamine. MS (ESI) m/z=677.2 (M+H)$^+$ Example 58. Cyclopropyl(6-((2-(1-(cyclopropylsulfonyl)-1H-pyrazol-4-yl)pyrimidin-4-yl)amino)-4-((((1r,4r)-4-((dimethylamino)methyl)cyclohexyl) methyl)amino)pyridin-3-yl)methanone The suspension of 2-(1-(cyclopropylsulfonyl)-1H-pyrazol-4-yl)pyrimidin-4-amine (40 mg, 0.151 mmol), tris(dibenzylideneacetone)dipalladium(0) (7 mg, 0.008 mmol), Xphos (7 mg, 0.015 mmol), cesium carbonate (123 mg, 0.377 mmol) and (6-chloro-4-((((1r,4r)-4-((dimethylamino) methyl)cyclohexyl)methyl)amino)pyridin-3-yl)(cyclopropyl)methanone (53 mg, 0.151 mmol) prepared in Reference Example 2 in toluene (1 mL) was stirred at room temperature for 30 minutes, and then heated to 90° C. for 18 hours. The mixture was cooled to room temperature, filtered through Celite, and then concentrated. The crude product was crystallised by DCM/MeOH and triturated with EA/isopropyl ether to yield cyclopropyl(6-((2-(1-(cyclopropylsulfonyl)-1H-pyrazol-4-yl)pyrimidin-4-yl)amino)-4-((((1r, 4r)-4-((dimethylamino)methyl)cyclohexyl)methyl)amino) pyridin-3-yl)methanone (20 mg) as a white solid. $^1$H-NMR (CDCl$_3$, 400 MHz) δ 9.29 (t, 1H), 8.87 (s, 1H), 8.66 (s, 1H), 8.46-8.45 (m, 2H), 7.56 (s, 1H), 7.29 (d, 1H), 6.99 (s, 1H), 3.15-3.13 (m, 2H), 2.85-2.79 (m, 1H), 2.63-2.58 (m, 1H), 2.19 (s, 6H), 2.08-2.06 (m, 2H), 1.91-1.85 (m, 4H), 1.54-1.52 (m, 2H), 1.49-1.41 (m, 1H), 1.24-1.15 (m, 7H), 1.07-0.88 (m, 4H); MS (ESI) m/z=579.3 (M+H)$^+$ Example 59. (6-((2-(1H-Pyrazol-4-yl)pyrimidin-4-yl)amino)-4-((((1r,4r)-4-((dimethylamino)methyl) cyclohexyl)methyl)amino)pyridin-3-yl)(cyclopropyl) methanone The suspension of 2-(1-(cyclopropylsulfonyl)-1H-pyrazol-4-yl)pyrimidin-4-amine (32 mg, 0.120 mmol), tris(dibenzylideneacetone)dipalladium(0) (5 mg, 0.05 mmol), BINAP (6 mg, 0.010 mmol), cesium carbonate (98 mg, 0.300 mmol) and (6-chloro-4-((((1r,4r)-4-((dimethylamino) methyl)cyclohexyl)methyl)amino)pyridin-3-yl)(cyclopropyl)methanone (35 mg, 0.100 mmol) prepared in Reference Example 2 in toluene (1 mL) was stirred at 160° C. for 90 minutes while being irradiate by MW (600 W). The mixture was diluted in DCM, filtered through Celite, and then concentrated. The crude product was purified by column chromatography (MeOH/DCM=0-50%) to yield cyclopropyl-(6-((2-(1-cyclopropylsulfonylpyrazol-4-yl)pyrimidin-4-yl)amino)-4-(isopropylamino)-3-pyridyl)methanone (4.9 mg) as a pale yellow solid. $^1$H-NMR (DMSO-$d_6$, 400 MHz) δ 9.24 (t, 1H), 8.97 (s, 1H), 8.39 (d, 1H), 8.28 (s, 1H), 8.07 (s, 1H), 7.59 (s, 1H), 7.23 (s, 1H), 3.16 (t, 2H), 2.92-2.87 (m, 1H), 2.21 (s, 6H), 1.99 (d, 2H), 1.83-1.77 (m, 4H), 1.61 (brs, 1H), 1.38 (brs, 1H), 1.24-1.22 (m, 2H), 1.07-0.82 (m, 6H)

Example 60. Cyclopropyl(6-((2-(1-cyclopropyl-1H-pyrazol-4-yl)pyrimidin-4-yl)amino)-4-((((1r,4r)-4-((dimethylamino)methyl)cyclohexyl)methyl)amino)pyridin-3-yl)methanone The title compound (22.5 mg) was prepared in the same fashion as Example 58, except that 2-(1-cyclopropylpyrazol-4-yl)pyrimidin-4-amine (32 mg, 0.157 mmol) was used instead of 2-(1-(cyclopropylsulfonyl)-1H-pyrazol-4-yl)pyrimidin-4-amine. $^1$H-NMR (CDCl$_3$, 400 MHz) δ 9.30 (s, 1H), 8.87 (s, 1H), 8.41 (d, 1H), 8.15 (s, 2H), 7.59 (s, 1H), 7.20 (s, 1H), 7.07 (d, 1H), 3.71-3.65 (m, 1H), 3.18 (t, 2H), 2.65-2.59 (m, 1H), 2.20 (s, 6H), 2.08 (d, 2H), 1.95-1.87 (m, 4H), 1.49-1.43 (m, 1H), 1.71-1.67 (m, 1H), 1.22-1.08 (m, 8H), 1.03-0.90 (m, 4H)

Example 61. Cyclopropyl(6-((2-(1-(cyclopropylmethyl)-1H-pyrazol-4-yl)pyrimidin-4-yl)amino)-4-((((1r,4r)-4-((dimethylamino)methyl)cyclohexyl)methyl)amino)pyridin-3-yl)methanone The title compound (20 mg) was prepared in the same fashion as Example 58, except that 2-(1-(cyclopropylmethyl)pyrazol-4-yl)pyrimidin-4-amine (34 mg, 0.157 mmol) was used instead of 2-(1-(cyclopropylsulfonyl)-1H-pyrazol-4-yl)pyrimidin-4-amine. MS (ESI) m/z=529.3 (M+H)$^+$ Example 62. Cyclopropyl(4-((((1r,4r)-4-((dimethylamino)methyl)cyclohexyl)methyl)amino)-6-((2-(1-(tetrahydrofuran-3-yl)-1H-pyrazol-4-yl)pyrimidin-4-yl)amino)pyridin-3-yl)methanone The title compound (24 mg) was prepared in the same fashion as Example 58, except that 2-(1-tetrahydrofuran-3-ylpyrazol-4-yl)pyrimidin-4-amine (40 mg, 0.171 mmol) was used instead of 2-(1-(cyclopropylsulfonyl)-1H-pyrazol-4-yl)pyrimidin-4-amine. MS (ESI) m/z=545.4 (M+H)$^+$ Example 63. 1-(6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)ethan-1-one Step 1. tert-Butyl (((1r,4r)-4-(((5-acetyl-2-chloropyridin-4-yl)amino)methyl)cyclohexyl)methyl)carbamate The title compound (665 mg) was prepared in the same fashion as Step 1 in Reference Example 2, except that 1-(4,6-dichloro-3-pyridyl)ethanone (500 mg, 2.631 mmol) was used instead of cyclopropyl-(4,6-dichloro-3-pyridyl)methanone. MS (ESI) m/z=396.1 (M+H)$^+$ Step 2. 1-(6-Chloro-4-((((1r,4r)-4-((dimethylamino)methyl)cyclohexyl)methyl)amino)pyridin-3-yl)ethan-1-one The reaction mixture of tert-butyl (((1r,4r)-4-(((5-acetyl-2-chloropyridin-4-yl)amino)methyl)cyclohexyl)methyl)carbamate (300 mg, 0.758 mmol) prepared in Step 1 and TFA (0.58 mL, 7.577 mmol) in DCM (15 mL) was stirred at room temperature overnight, and then concentrated. The residue was diluted in DCM, added 1 N NaOH soln. (>pH8), washed by water, dried over MgSO$_4$, and then concentrated. The crude product (150 mg) was diluted in MeOH (5 mL), added formaldehyde (1.13 mL, 15.212 mmol) and sodium triacetoxyborohydride (322.41 mg, 2.521 mmol), and was stirred at 70° C. overnight. The reaction mixture was cooled, concentrated, diluted in DCM, washed by water, dried over MgSO$_4$, and then concentrated. The crude product was purified by column chromatography (MeOH/DCM=0-20%) to yield 1-(6-chloro-4-((((1r,4r)-4-((dimethylamino)methyl)cyclohexyl)methyl)amino)pyridin-3-yl)ethan-1-one (34 mg) as a colorless oil. MS (ESI) m/z=324.2 (M+H)$^+$ Step 3. 1-(6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)ethan-1-one The title compound (6.5 mg) was prepared in the same fashion as Example 58, except that 1-(6-chloro-4-((((1r,4r)-4-((dimethylamino)methyl)cyclohexyl)methyl)amino)pyridin-3-yl)ethan-1-one (20 mg, 0.062 mmol) prepared in Step 2 was used instead of (6-chloro-4-((((1r,4r)-4-((dimethylamino)methyl)cyclohexyl)methyl)amino)pyridin-3-yl)(cyclopropyl)methanone. $^1$H-NMR (CDCl$_3$, 400 MHz) δ 9.32 (t, 1H), 8.66 (s, 1H), 8.62 (s, 1H), 8.46 (d, 1H), 8.44 (s, 1H), 7.58 (s, 1H), 7.26 (s, 1H), 7.02 (d, 1H), 3.16 (t, 2H), 2.86-2.81 (m, 1H), 2.58 (s, 3H), 2.19 (s, 6H), 2.07 (d, 2H), 1.92-1.86 (m, 4H), 1.55-1.51 (m, 2H), 1.48-1.42 (m, 1H), 1.42-1.24 (m, 3H), 1.24-1.18 (m, 2H), 0.98-0.89 (m, 2H)

Example 64. (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(4-fluorophenyl)methanone Step 1. tert-Butyl (((1r,4r)-4-(((2-chloro-5-(4-fluorobenzoyl)pyridin-4-yl)amino)methyl)cyclohexyl)methyl)carbamate The title compound (425 mg) was prepared in the same fashion as Step 1 in Reference Example 2, except that (4,6-dichloro-3-pyridyl)-(4-fluorophenyl)methanone (300 mg, 1.111 mmol) was used instead of cyclopropyl-(4,6-dichloro-3-pyridyl)methanone. MS (ESI) m/z=476.1 (M+H)$^+$ Step 2. (6-Chloro-4-((((1r,4r)-4-((dimethylamino)methyl)cyclohexyl)methyl)amino)pyridin-3-yl)(4-fluorophenyl)methanone The title compound as a colorless oil (40 mg) was prepared in the same fashion as Step 2 in Example 63, except that tert-butyl(((1r,4r)-4-(((2-chloro-5-(4-fluorobenzoyl)pyridin-4-yl)amino)methyl)cyclohexyl)methyl)carbamate (100 mg, 0.21 mmol) prepared in Step 1 was used instead of tert-butyl (((1r,4r)-4-(((5-acetyl-2-chloropyridin-4-yl)amino)methyl)cyclohexyl)methyl)carbamate. $^1$H-NMR (CDCl$_3$, 400 MHz) δ 8.92 (t, 1H), 8.30 (s, 1H), 7.66 (q, 2H), 7.17 (t, 2H), 6.64 (s, 1H), 3.10 (t, 2H), 2.20 (s, 6H), 2.09 (d, 2H), 1.90 (brs, 4H), 1.46-1.44 (m, 1H), 1.31-1.26 (m, 1H), 1.14-1.05 (m, 2H), 0.99-0.90 (m, 2H)

Step 3. (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(4-fluorophenyl)methanone The title compound (5 mg) was prepared in the same fashion as Example 58, except that (6-chloro-4-((((1r,4r)-4-((dimethylamino)methyl)cyclohexyl)methyl)amino)pyridin-3-yl)(4-fluorophenyl)methanone (35 mg, 0.087 mmol) prepared in Step 2 was used instead of (6-chloro-4-((((1r,4r)-4-((dimethylamino)methyl)cyclohexyl)methyl)amino)pyridin-3-yl)(cyclopropyl)methanone. $^1$H-NMR (CDCl$_3$, 400 MHz) δ 9.09 (t, 1H), 8.67 (s, 1H), 8.45 (s, 1H), 8.44 (d, 1H), 8.32 (s, 1H), 7.74 (s, 1H), 7.67 (t, 1H), 7.25 (d, 1H), 7.19-7.13 (m, 3H), 3.23 (t, 2H), 2.86-2.81 (m, 1H), 2.21 (s, 6H), 2.12-2.10 (m, 2H), 1.97-1.88 (m, 5H), 1.57-1.51 (m, 3H), 1.28-1.16 (m, 4H), 1.02-0.95 (m, 2H)

Example 65. 1-(6-((2-(1-(Cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)ethan-1-one

Step 1. tert-Butyl (((1r,4r)-4-(((5-acetyl-2-chloropyridin-4-yl)oxy)methyl)cyclohexyl)methyl)carbamate Sodium hydride, 60% in mineral oil (104 mg, 2.598 mmol) was added to the solution of tert-butyl (((1r,4r)-4-(hydroxymethyl)cyclohexyl)methyl)carbamate (300 mg, 1.233 mmol) in DMF (10 mL) at 0° C. and the reaction mixture was stirred for 30 minutes. After 1-(4,6-dichloropyridin-3-yl)ethan-1-one (258 mg, 1.356 mmol) being added, the reaction mixture was stirred at 70° C. overnight. The reaction mixture was cooled, diluted in DCM, washed by water, dried over MgSO$_4$, and then concentrated. The crude product was purified by column chromatography (EA/n-Hex=0-50%) to yield tert-butyl (((1r,4r)-4-(((5-acetyl-2-chloropyridin-4-yl)oxy)methyl)cyclohexyl)methyl)carbamate (120 mg) as a white solid. MS (ESI) m/z=397.1 (M+H)$^+$

Step 2. 1-(4-(((1r,4r)-4-(Aminomethyl)cyclohexyl)methoxy)-6-chloropyridin-3-yl)ethan-1-one The title compound as a colorless oil (73 mg) was prepared in the same fashion as Step 2 in Reference Example 2, except that tert-butyl (((1r,4r)-4-(((5-acetyl-2-chloropyridin-4-yl)oxy)methyl)cyclohexyl)methyl)carbamate (97.5 mg, 0.246 mmol) prepared in Step 1 was used instead of tert-butyl (((1r,4r)-4-(((2-chloro-5-(cyclopropanecarbonyl)pyridin-4-yl)amino)methyl)cyclohexyl)methyl)carbamate. MS (ESI) m/z=269.1 (M+H)$^+$

Step 3. 1-(6-Chloro-4-(((1r,4r)-4-((dimethylamino)methyl)cyclohexyl)methoxy)pyridin-3-yl)ethan-1-one The title compound as a colorless oil (38 mg) was prepared in the same fashion as Step 3 in Reference Example 2, except that 1-(4-(((1r,4r)-4-(aminomethyl)cyclohexyl)methoxy)-6-chloropyridin-3-yl)ethan-1-one (67 mg, 0.226 mmol) prepared in Step 2 was used instead of (4-((((1r,4r)-4-(aminomethyl)cyclohexyl)methyl)amino)-6-chloropyridin-3-yl)(cyclopropyl)methanone. MS (ESI) m/z=325.2 (M+H)$^+$

Step 4. 1-(6-((2-(1-(Cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)ethan-1-one The title compound as a pale yellow oil (1 mg) was prepared in the same fashion as Step 2 in Reference Example 1, except that 1-(6-chloro-4-(((1r,4r)-4-((dimethylamino)methyl)cyclohexyl)methoxy)pyridin-3-yl)ethan-1-one (30 mg, 0.092 mmol) prepared in Step 3 was used instead of 4-((2-chloro-5-(cyclopropanecarbonyl)-4-pyridyl)amino)cyclohexanone. MS (ESI) m/z=554.2 (M+H)

Example 66. Cyclopropyl(6-((2-(1-(cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)methanone

Step 1. tert-Butyl (((1r,4r)-4-(((2-chloro-5-(cyclopropanecarbonyl)pyridin-4-yl)oxy)methyl)cyclohexyl)methyl)carbamate The title compound (1.39 g) was prepared in the same fashion as Step 1 in Example 65, except that cyclopropyl-(4,6-dichloro-3-pyridyl)methanone (1.0 g, 4.628 mmol) was used instead of 1-(4,6-dichloropyridin-3-yl)ethan-1-one. MS (ESI) m/z=423.1 (M+H)$^+$

Step 2. (6-Chloro-4-(((1r,4r)-4-((dimethylamino)methyl)cyclohexyl)methoxy)pyridin-3-yl)(cyclopropyl)methanone The title compound as a colorless oil (170 mg) was prepared in the same fashion as Step 2 in Example 63, except that tert-butyl (((1r,4r)-4-(((2-chloro-5-(cyclopropanecarbonyl)pyridin-4-yl)oxy)methyl)cyclohexyl)methyl)carbamate (280 mg, 0.867 mmol) prepare in Step 1 was used instead of tert-butyl (((1r,4r)-4-(((5-acetyl-2-chloropyridin-4-yl)amino)methyl)cyclohexyl)methyl)carbamate. MS (ESI) m/z=351.2 (M+H)$^+$

Step 3. Cyclopropyl(6-((2-(1-(cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)methanone The title compound (7 mg) was prepared in the same fashion as Step 2 in Reference Example 1, except that (6-chloro-4-(((1r,4r)-4-((dimethylamino)methyl)cyclohexyl)methoxy)pyridin-3-yl)(cyclopropyl)methanone (53 mg, 0.151 mmol) prepared in Step 2 was used instead of 4-((2-chloro-5-(cyclopropanecarbonyl)-4-pyridyl)amino)cyclohexanone. $^1$H-NMR (CDCl$_3$, 400 MHz) δ 8.66 (s, 1H), 8.50 (s, 1H), 8.48 (d, 2H), 8.43 (s, 1H), 7.72 (s, 1H), 7.59 (s, 1H), 7.16 (d, 1H), 4.05 (d, 2H), 2.87-2.80 (m, 1H), 2.80-2.74 (m, 1H), 2.21 (s, 6H), 2.11-2.10 (m, 2H), 1.96-1.90 (m, 5H), 1.56-1.52 (m, 2H), 1.49-1.41 (m, 1H), 1.28-1.22 (m, 7H), 1.02-0.97 (m, 4H); MS (ESI) m/z=580.3 (M+H)$^+$

Example 67. (4-((((1r,4r)-4-(Aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone

Step 1. tert-Butyl (((1r,4r)-4-(((5-(cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)carbamate The title compound as a pale yellow oil (72 mg) was prepared in the same fashion as Step 2 in Reference 1, except that tert-butyl (((1r,4r)-4-(((2-chloro-5-(cyclopropanecarbonyl)pyridin-4-yl)amino)methyl)cyclohexyl)methyl)carbamate (191 mg, 0.452 mmol) prepared in Step 1 in Reference Example 2 was used instead of 4-((2-chloro-5-(cyclopropanecarbonyl)-4-pyridyl)amino)cyclohexanone. MS (ESI) m/z=651.3 (M+H)$^+$ Step 2. (4-((((1r,4r)-4-(Aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone The reaction mixture of tert-butyl (((1r,4r)-4-(((5-(cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)carbamate (72 mg, 0.111 mmol) prepared in Step 1 and TFA (0.09 mL, 1.112 mmol) in DCM (2 mL) was stirred at room temperature overnight, and then concentrated. The residue was diluted in DCM, added 1 N NaOH soln. (>pH8), washed by water, dried over MgSO$_4$, and then concentrated. The crude product was purified by column chromatography (MeOH/DCM=0-20%) to yield (4-((((1r,4r)-4-(aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone (26 mg) as an off-white solid. $^1$H-NMR (CDCl$_3$, 400 MHz) δ 9.31 (s, 1H), 8.87 (s, 1H), 8.66 (s, 1H), 8.44 (s, 2H), 8.16 (s, 1H), 7.21 (s, 1H), 7.11 (s, 1H), 4.99 (s, 1H), 3.14 (m, 2H), 2.83 (brs, 1H), 2.60 (brs, 1H), 2.55-2.53 (m, 2H), 1.93-1.83 (m, 6H), 1.66 (brs, 1H), 1.52 (brs, 2H), 1.30-1.20 (m, 5H), 1.16-1.07 (m, 2H), 0.99-0.90 (m, 4H); MS (ESI) m/z=551.3 (M+H)$^+$ Example 68. N-(((1r,4r)-4-(((5-(Cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)acetamide Acetyl chloride (0.01 mL, 0.1400 mmol) was added slowly to an ice cooled solution of (4-((((1r,4r)-4-(aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone (50 mg, 0.0900 mmol) prepared in Example 67 in pyridine (0.5 mL) under a nitrogen atmosphere. After stirring at 0-5° C. for 1 hour, the reaction mixture was maintained at ambient temperature overnight. This mixture was then poured into water and extracted with EA. The combined organic phases were washed with 1 N HCl and then with a sat. NaHCO$_3$ sol. The organic layer was dried over sodium sulfate, filtered, and concentrated in vacuo to give N-(((1r,4r)-4-(((5-(cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)acetamide (14 mg) as a white solid. $^1$H-NMR (CDCl$_3$, 400 MHz) δ 9.33 (s, 1H), 8.85 (s, 1H), 8.66 (s, 1H), 8.44 (s, 2H), 7.84 (s, 1H), 7.19 (s, 1H), 7.14 (d, 1H), 5.51 (s, 1H), 3.15-3.11 (m, 2H), 2.83 (brs, 1H), 2.60 (brs, 1H), 1.99 (s, 3H), 1.92-1.89 (m, 2H), 1.83-1.80 (m, 4H), 1.52-1.47 (m, 3H), 1.26-1.21 (m, 5H), 1.16-1.07 (m, 2H), 1.00-0.97 (m, 4H); MS (ESI) m/z=593.2 (M+H)$^+$ Example 69. Cyclopropyl(6-((2-(1-(cyclopropylsulfonyl)-1H-pyrazol-4-yl)pyrimidin-4-yl)amino)-4-((((1r,4r)-4-((isopropylamino)methyl)cyclohexyl)methyl)amino)pyridin-3-yl)methanone To a solution of (4-((((1r,4r)-4-(aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone (40 mg, 0.0700 mmol) prepared in Example 67 in MeOH (0.4 mL) was added acetone (0.01 mL, 0.0700 mmol) and the reaction mixture was stirred at room temperature overnight. Sodium borohydride (6 mg, 0.1500 mmol) was added and the reaction mixture was stirred for 3.5 hours open to air. The reaction was quenched by addition of HCl (2 M) maintain a pH of 1. The aqueous layer was extracted with diethyl ether and 3 M NaOH was added resulting in a pH of 14. The aqueous layer was extracted with diethyl ether and the combined organic layers were dried with MgSO$_4$. The product was purified by flash column chromatography (30% MeOH in DCM) giving cyclopropyl(6-((2-(1-(cyclopropylsulfonyl)-1H-pyrazol-4-yl)pyrimidin-4-yl)amino)-4-((((1r,4r)-4-((isopropylamino)methyl)cyclohexyl)methyl)amino)pyridin-3-yl)methanone (10 mg) as a white solid. $^1$H-NMR (CDCl$_3$, 400 MHz) δ 8.65 (s, 1H), 8.43 (s, 1H), 8.37 (s, 1H), 7.84 (s, 1H), 7.36 (s, 1H), 6.79 (s, 1H), 6.04 (s, 1H), 3.87 (brs, 1H), 3.75-3.70 (m, 1H), 3.07 (s, 2H), 2.82 (brs, 1H), 2.74 (brs, 1H), 2.43 (brs, 2H), 1.85-1.81 (m, 4H), 1.59-1.52 (m, 4H), 1.41-1.20 (m, 3H), 1.05 (d, 6H), 1.04-0.97 (m, 2H), 0.74-0.31 (m, 4H); MS (ESI) m/z=593.3 (M+H)$^+$ Example 70. (4-((((1r,4r)-4-((Cyclopentylamino)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone The title compound (30 mg) was prepared in the same fashion as Example 69, except that cyclopentanone (6 mg, 0.073 mmol) was used instead of acetone. $^1$H-NMR (CDCl$_3$, 400 MHz) δ 9.30 (s, 1H), 8.86 (s, 1H), 8.66 (s, 1H), 8.44 (s, 2H), 7.95 (brs, 1H), 7.25 (s, 1H), 7.06 (s, 1H), 3.13 (d, 2H), 3.02 (brs, 1H), 2.82 (brs, 1H), 2.59 (brs, 1H), 2.43 (d, 2H), 1.91-1.82 (m, 6H), 1.67 (s, 3H), 1.52-1.28 (m, 4H), 1.20-1.16 (m, 3H), 1.07-1.05 (m, 4H), 1.00-0.94 (m, 2H), 0.91-0.84 (m, 4H); MS (ESI) m/z=619.3 (M+H)$^+$ Example 71. Cyclopropyl(6-((2-(1-(cyclopropylsulfonyl)-1H-pyrazol-4-yl)pyrimidin-4-yl)amino)-4-((((1r,4r)-4-(((3-hydroxy-3-methylbutan-2-yl)amino)methyl)cyclohexyl)methyl)amino)pyridin-3-yl)methanone The title compound (6 mg) was prepared in the same fashion as Example 69, except that 3-hydroxy-3-methyl-2-butanone (28 mg, 0.272 mmol) was used instead of acetone. MS (ESI) m/z=638.2 (M+H)$^+$ Example 72. N-(((1r,4r)-4-(((5-(Cyclopropanecarbonyl)-2-((2-(1-(cyclopropylsulfonyl)-1H-pyrazol-4-yl)pyrimidin-4-yl)amino)pyridin-4-yl)amino)methyl)cyclohexyl)methyl)isobutyramide The title compound (6 mg) was prepared in the same fashion as Example 68, except that isobutyryl chloride (29 mg, 0.272 mmol) was used instead of acetyl chloride. $^1$H-NMR (CDCl$_3$, 400 MHz) δ 9.33 (t, 1H), 8.86 (s, 1H), 8.67 (s, 1H), 8.46 (d, 1H), 8.45 (s, 1H), 7.72 (brs, 1H), 7.22 (d, 1H), 7.12 (d, 1H), 5.48 (brs, 1H), 3.17-3.11 (m, 4H), 2.87-2.80 (m, 1H), 2.64-2.58 (m, 1H), 2.39-2.32 (m, 1H), 1.93-1.90 (m, 2H), 1.83-1.79 (m, 2H), 1.56-1.51 (m, 2H), 1.50-1.43 (m, 1H), 1.27-1.19 (m, 4H), 1.17 (d, 6H), 1.14-1.07 (m, 2H), 1.04-0.98 (m, 4H); MS (ESI) m/z=621.3 (M+H)$^+$

Example 73. Cyclopropyl(6-((2-(1-(cyclopropylsulfonyl)-1H-pyrazol-4-yl)pyrimidin-4-yl)amino)-4-((((1r,4r)-4-(((1,1-difluoropropan-2-yl)amino) methyl)cyclohexyl)methyl)amino)pyridin-3-yl) methanone The title compound (25 mg) was prepared in the same fashion as Example 69, except that 1,1-difluoropropan-2-one (85 mg, 0.908 mmol) was used instead of acetone. $^1$H-NMR (CDCl$_3$, 400 MHz) δ 9.31 (t, 1H), 8.87 (s, 1H), 8.66 (s, 1H), 8.43 (d, 2H), 8.25 (s, 1H), 7.20 (d, 1H), 7.11 (s, 1H), 5.62 (dt, 1H), 3.14 (t, 2H), 2.89-2.81 (m, 2H), 2.60-2.46 (m, 3H), 1.92-1.83 (m, 4H), 1.66 (brs, 1H), 1.52 (brs, 2H), 1.40 (brs, 1H), 1.28-1.20 (d, 4H), 1.20-1.14 (m, 5H), 1.07-0.98 (m, 4H)

Example 74. 6-((2-(1-(Cyclopropylsulfonyl)-1H-pyrazol-4-yl)pyrimidin-4-yl)amino)-N-(2-fluoroethyl)-4-(isopropylamino)nicotinamide

Step 1. 6-Chloro-N-(2-fluoroethyl)-4-(isopropylamino)pyridine-3-carboxamide The reaction mixture of 4,6-dichloro-N-(2-fluoroethyl) pyridine-3-carboxamide (150 mg, 0.633 mmol) prepared in Reference Example 3, isopropylamine (0.11 mL, 1.266 mmol) and DIPEA (0.33 mL, 1.898 mmol) in DMA (3 mL) was stirred at 90° C. overnight. The reaction mixture was cooled, diluted in EA, washed by water, dried over MgSO$_4$, and then concentrated. The crude product was purified by column chromatography (EA/n-Hex=0-50%) to yield 6-chloro-N-(2-fluoroethyl)-4-(isopropylamino)pyridine-3-carboxamide (146 mg) as a pale yellow liquid. MS (ESI) m/z=260.1 (M+H)$^+$

Step 2. 6-((2-(1-(Cyclopropylsulfonyl)-1H-pyrazol-4-yl)pyrimidin-4-yl)amino)-N-(2-fluoroethyl)-4-(isopropylamino)nicotinamide The title compound as an off-white solid (9 mg) was prepared in the same fashion as Step 2 in Reference Example 1, except that 6-chloro-N-(2-fluoroethyl)-4-(isopropylamino)pyridine-3-carboxamide (49 mg, 0.188 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 8.63 (s, 1H), 8.44 (s, 1H), 8.41 (d, 1H), 8.29 (d, 1H), 8.25 (s, 1H), 7.77 (s, 1H), 7.29 (s, 1H), 7.03 (d, 1H), 6.50 (t, 1H), 4.68 (t, 1H), 4.56 (t, 1H), 3.82-3.76 (m, 2H), 3.71 (q, 1H), 2.86-2.82 (m, 1H), 1.55-1.51 (m, 2H), 1.36 (d, 6H), 1.25-1.21 (m, 2H); MS (ESI) m/z=489.2 (M+H)$^+$

Example 75. 6-((2-(1-(Cyclopropylsulfonyl)-1H-pyrazol-4-yl)pyrimidin-4-yl)amino)-N-(2-fluoroethyl)-4-(((1R,3S)-3-(hydroxymethyl)cyclopentyl) amino)nicotinamide

Step 1. 6-Chloro-N-(2-fluoroethyl)-4-(((1R,3S)-3-(hydroxymethyl)cyclopentyl)amino)pyridine-3-carboxamide The title compound (209 mg) was prepared in the same fashion as Step 1 in Example 74, except that ((1R,3S)-3-aminocyclopentyl)methanol (146 mg, 1.266 mmol) was used instead of isopropylamine. MS (ESI) m/z=316.1 (M+H)$^+$

Step 2. 6-((2-(1-(Cyclopropylsulfonyl)-1H-pyrazol-4-yl)pyrimidin-4-yl)amino)-N-(2-fluoroethyl)-4-(((1R,3S)-3-(hydroxymethyl)cyclopentyl)amino) nicotinamide The title compound as an off-white solid (5 mg) was prepared in the same fashion as Step 2 in Reference Example 1, except that 6-chloro-N-(2-fluoroethyl)-4-(((1R,3s)-3-(hydroxymethyl)cyclopentyl)amino)pyridine-3-carboxamide (60 mg, 0.188 mmol) prepared in Step 1 was used instead of 4-((2-chloro-5-(cyclopropanecarbonyl)-4-pyridyl)amino) cyclohexanone. $^1$H-NMR (CDCl$_3$, 400 MHz) δ 9.03 (d, 1H), 8.66 (s, 1H), 8.49 (s, 1H), 8.46 (s, 1H), 8.41 (d, 1H), 7.63 (s, 1H), 7.19 (s, 1H), 7.10 (d, 2H), 4.33 (t, 3H), 4.11-3.98 (m, 3H), 3.70-3.59 (m, 2H), 2.88-2.80 (m, 1H), 2.47-2.38 (m, 1H), 2.38-2.28 (m, 1H), 2.18-2.08 (m, 1H), 1.97-1.87 (m, 1H), 1.82-1.72 (m, 1H), 1.56-1.51 (m, 3H), 1.47-1.39 (m, 1H), 1.26-1.19 (m, 2H)

Example 76. 6-((2-(1-(Cyclopropylsulfonyl)-1H-pyrazol-4-yl)pyrimidin-4-yl)amino)-N-(2-fluoroethyl)-4-(((1s,4s)-4-hydroxy-4-methylcyclohexyl) amino)nicotinamide

Step 1. 6-Chloro-N-(2-fluoroethyl)-4-(((1s,4s)-4-hydroxy-4-methylcyclohexyl)amino)nicotinamide The title compound (169 mg) was prepared in the same fashion as Step 1 in Example 74, except that cis-4-amino-1-methylcyclohexan-1-ol (123 mg, 0.949 mmol) was used instead isopropylamine. MS (ESI) m/z=330.1 (M+H)$^+$

Step 2. 6-((2-(1-(Cyclopropylsulfonyl)-1H-pyrazol-4-yl)pyrimidin-4-yl)amino)-N-(2-fluoroethyl)-4-(((1s,4s)-4-hydroxy-4-methylcyclohexyl)amino) nicotinamide The title compound as an off-white solid (66 mg) was prepared in the same fashion as Step 2 in Reference Example 1, except that 6-chloro-N-(2-fluoroethyl)-4-(((1s,4s)-4-hydroxy-4-methylcyclohexyl)amino)nicotinamide (137 mg, 0.415 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 8.63 (s, 1H), 8.48-8.33 (m, 3H), 8.25 (s, 1H), 7.65 (s, 1H), 7.21 (d, 1H), 7.01 (s, 1H), 6.46 (t, 1H), 4.67 (t, 1H), 4.55 (t, 1H), 3.78 (q, 1H), 3.70 (q, 1H), 3.48-3.37 (m, 1H), 2.87-2.78 (m, 1H), 1.99-1.90 (m, 2H), 1.82-1.65 (m, 4H), 1.63-1.56 (m, 2H), 1.56-1.50 (m, 2H), 1.30 (s, 3H), 1.25-1.18 (m, 2H); MS (ESI) m/z=559.2 (M+H)$^+$

Example 77. 6-((2-(1-(Cyclopropylsulfonyl)-1H-pyrazol-4-yl)pyrimidin-4-yl)amino)-N-(2-fluoroethyl)-4-(((1s,4s)-4-((2-fluoroethyl)amino)cyclohexyl)amino)nicotinamide

Step 1. 6-Chloro-N-(2-fluoroethyl)-4-(((1s,4s)-4-((2-fluoroethyl)amino)cyclohexyl)amino)nicotinamide The title compound (177 mg) was prepared in the same fashion as Step 1 in Example 74, except that (1s,4s)-N'-(2-fluoroethyl)cyclohexane-1,4-diamine (152 mg, 0.949 mmol) was used instead isopropylamine. MS (ESI) m/z=361.1 (M+H)$^+$

Step 2. 6-((2-(1-(Cyclopropylsulfonyl)-1H-pyrazol-4-yl)pyrimidin-4-yl)amino)-N-(2-fluoroethyl)-4-(((1s,4s)-4-((2-fluoroethyl)amino)cyclohexyl)amino) nicotinamide The title compound as an off-white solid (88 mg) was prepared in the same fashion as Step 2 in Reference Example 1, except that 6-chloro-N-(2-fluoroethyl)-4-(((1s,4s)-4-((2-fluoroethyl)amino)cyclohexyl)amino)nicotinamide (136 mg, 0.377 mmol) prepared in Step 1 was used instead of 4-((2-chloro-5-(cyclopropanecarbonyl)-4-pyridyl)amino) cyclohexanone. $^1$H-NMR (CDCl$_3$, 400 MHz) δ 8.73 (d, 1H), 8.61 (s, 1H), 8.49-8.35 (m, 2H), 8.24 (s, 1H), 7.74 (s, 1H), 7.22 (s, 1H), 7.04 (d, 1H), 6.47 (t, 1H), 4.69 (t, 1H), 4.62 (t, 1H), 4.56 (t, 1H), 4.48 (t, 1H), 3.83-3.67 (m, 3H), 2.97 (t, 1H), 2.91 (t, 1H), 2.88-2.79 (m, 1H), 2.72-2.6 (m, 1H), 2.05-1.91 (m, 2H), 1.87-1.74 (m, 4H), 1.57-1.42 (m, 4H), 1.26-1.17 (m, 2H); MS (ESI) m/z=590.2 (M+H)$^+$

Example 78. 6-((2-(1-(Cyclopropylsulfonyl)-1H-pyrazol-4-yl)pyrimidin-4-yl)amino)-N-(2,2-difluoroethyl)-4-(isopropylamino)nicotinamide

Step 1. 6-Chloro-N-(2,2-difluoroethyl)-4-(isopropylamino)pyridine-3-carboxamide The title compound as a pale yellow liquid (172 mg) was prepared in the same fashion as Step 1 in Example 74, except that 4,6-dichloro-N-(2,2-difluoroethyl)pyridine-3-carboxamide (200 mg, 0.784 mmol) prepared in Reference Example 4 was used instead of 4,6-dichloro-N-(2-fluoroethyl)pyridine-3-carboxamide. MS (ESI) m/z=278.1 (M+H)$^+$

Step 2. 6-((2-(1-(Cyclopropylsulfonyl)-1H-pyrazol-4-yl)pyrimidin-4-yl)amino)-N-(2,2-difluoroethyl)-4-(isopropylamino)nicotinamide The title compound as an off-white solid (12 mg) was prepared in the same fashion as Step 2 in Reference Example 1, except that 6-chloro-N-(2,2-difluoroethyl)-4-(isopropylamino)pyridine-3-carboxamide (52 mg, 0.188 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 8.64 (s, 1H), 8.44 (s, 1H), 8.42 (d, 1H), 8.27 (d, 1H), 8.25 (s, 1H), 7.64 (s, 1H), 7.29 (s, 1H), 7.04 (d, 1H), 6.34 (q, 1H), 5.98 (tt, 1H), 3.82-3.75 (m, 3H), 2.87-2.81 (m, 1H), 1.56-1.51 (m, 2H), 1.37 (d, 6H), 1.25-1.22 (m, 2H)

Example 79. 6-((2-(1-(Cyclopropylsulfonyl)-1H-pyrazol-4-yl)pyrimidin-4-yl)amino)-N-(2,2-difluoroethyl)-4-(((1s,4s)-4-hydroxycyclohexyl)amino)nicotinamide

Step 1. 6-Chloro-N-(2,2-difluoroethyl)-4-(((1s,4s)-4-hydroxycyclohexyl)amino)nicotinamide The title compound as a pale yellow liquid (171 mg) was prepared in the same fashion as Step 1 in Example 74, except that 4,6-dichloro-N-(2,2-difluoroethyl)pyridine-3-carboxamide (200 mg, 0.784 mmol) prepared in Reference Example 4 and cis-4-aminocyclohexanol HCl (214 mg, 1.411 mmol) was used instead of 4,6-dichloro-N-(2-fluoroethyl)pyridine-3-carboxamide and isopropylamine. MS (ESI) m/z=334.1 (M+H)$^+$

Step 2. 6-((2-(1-(Cyclopropylsulfonyl)-1H-pyrazol-4-yl)pyrimidin-4-yl)amino)-N-(2,2-difluoroethyl)-4-(((1s,4s)-4-hydroxycyclohexyl)amino)nicotinamide The title compound as an off-white solid (6 mg) was prepared in the same fashion as Step 2 in Reference Example 1, except that 6-chloro-N-(2,2-difluoroethyl)-4-(((1s,4s)-4-hydroxycyclohexyl)amino)nicotinamide (69 mg, 0.207 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 8.64 (s, 1H), 8.60 (d, 1H), 8.43 (d, 1H), 8.27 (s, 1H), 7.62 (s, 1H), 7.18 (s, 1H), 7.12 (d, 1H), 6.34 (t, 1H), 5.98 (tt, 1H), 3.92-3.73 (m, 3H), 3.70-3.61 (m, 1H), 2.87-2.79 (m, 1H), 1.99-1.89 (m, 2H), 1.89-1.77 (m, 4H), 1.57-1.5 (m, 2H), 1.25-1.19 (m, 2H)

Example 80. 6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)-N-((1r,4r)-4-hydroxycyclohexyl)nicotinamide

Step 1. 4,6-Dichloro-N-((1r,4r)-4-hydroxycyclohexyl)nicotinamide

The title compound (529 mg) was prepared in the same fashion as Reference Example 3, except that (1r,4r)-4-aminocyclohexan-1-ol (660 mg, 5.729 mmol) used instead of 2-fluoroethylamine HCl. MS (ESI) m/z=290.9 (M+H)$^+$

Step 2. 6-Chloro-4-(((1s,4s)-4-((2-fluoroethyl)amino)cyclohexyl)amino)-N-((1r,4r)-4-hydroxycyclohexyl)nicotinamide The title compound as a pale yellow liquid (97 mg) was prepared in the same fashion as Step 1 in Example 74, except that 4,6-dichloro-N-((1r,4r)-4-hydroxycyclohexyl)nicotinamide (200 mg, 0.692 mmol) prepared in Step 1 and (1s,4s)-N$^1$-(2-fluoroethyl)cyclohexane-1,4-diamine (166 mg, 1.037 mmol) were used instead of 4,6-dichloro-N-(2-fluoroethyl)pyridine-3-carboxamide and isopropylamine. MS (ESI) m/z=413.0 (M+H)$^+$

Step 3. 6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)-N-((1r,4r)-4-hydroxycyclohexyl)nicotinamide The title compound as an off-white solid (24 mg) was prepared in the same fashion as Step 2 in Reference Example 1, except that 6-chloro-4-(((1s,4s)-4-((2-fluoroethyl)amino)cyclohexyl)amino)-N-((1r,4r)-4-hydroxycyclohexyl)nicotinamide (86 mg, 0.207 mmol) prepared in Step 2 was used instead of 4-((2-chloro-5-(cyclopropanecarbonyl)-4-pyridyl)amino)cyclohexanone. $^1$H-NMR (CDCl$_3$, 400 MHz) δ 8.76 (d, 1H), 8.60 (s, 1H), 8.53-8.32 (m, 2H), 8.14 (s, 1H), 7.62 (s, 1H), 7.19 (s, 1H), 7.07 (d, 1H), 5.86 (d, 1H), 4.62 (t, 1H), 4.51 (t, 1H), 3.99-3.87 (m, 1H), 3.82-3.73 (m, 1H), 3.73-3.62 (m, 1H), 2.99 (t, 1H), 2.91 (t, 1H), 2.88-2.79 (m, 1H), 2.72-2.61 (m, 1H), 2.18-2.09 (m, 2H), 2.09-2.02 (m, 2H), 2.02-1.93 (m, 2H), 1.89-1.75 (m, 2H), 1.58-1.41 (m, 6H), 1.41-1.19 (m, 6H); MS (ESI) m/z=642.2 (M+H)$^+$ Example 81. 6-((2-(1-(Cyclopropylsulfonyl)-1H-pyrazol-4-yl)pyrimidin-4-yl)amino)-N-(2,2-difluoroethyl)-4-((((1r,4r)-4-((dimethylamino)methyl)cyclohexyl)methyl)amino)nicotinamide Step 1. tert-Butyl ((((1r,4r)-4-(((2-chloro-5-((2,2-difluoroethyl)carbamoyl)pyridin-4-yl)amino)methyl)cyclohexyl)methyl)carbamate The title compound as an off-white solid (350 mg) was prepared in the same fashion as Step 1 in Reference Example 2, except that 4,6-dichloro-N-(2,2-difluoroethyl)pyridine-3-carboxamide (200 mg, 0.784 mmol) prepared in Reference Example 4 was used instead of cyclopropyl-(4,6-dichloro-3-pyridyl)methanone. MS (ESI) m/z=461.2 (M+H)$^+$ Step 2. 4-((((1r,4r)-4-(Aminomethyl)cyclohexyl)methyl)amino)-6-chloro-N-(2,2-difluoroethyl)nicotinamide The title compound as a colorless oil (88 mg) was prepared in the same fashion as Step 2 in Reference Example 2, except that tert-butyl ((((1r,4r)-4-(((2-chloro-5-((2,2-difluoroethyl)carbamoyl)pyridin-4-yl)amino)methyl)cyclohexyl)methyl)carbamate (350 mg, 0.758 mmol) prepared in Step 1 was used instead of tert-butyl ((((1r,4r)-4-(((2-chloro-5-(cyclopropanecarbonyl)pyridin-4-yl)amino)methyl)cyclohexyl)methyl)carbamate. MS (ESI) m/z=361.1 (M+H)$^+$ Step 3. 6-Chloro-N-(2,2-difluoroethyl)-4-((((1r,4r)-4-((dimethylamino)methyl)cyclohexyl)methyl)amino)nicotinamide The title compound as a colorless oil (46 mg) was prepared in the same fashion as Step 3 in Reference Example 2, except that 4-((((1r,4r)-4-(aminomethyl)cyclohexyl)methyl)amino)-6-chloro-N-(2,2-difluoroethyl)nicotinamide (88 mg, 0.244 mmol) prepared in Step 2 was used instead of (4-((((1r,4r)-4-(aminomethyl)cyclohexyl)methyl)amino)-6-chloropyridin-3-yl)(cyclopropyl)methanone. MS (ESI) m/z=389.2 (M+H)$^+$ Step 4. 6-((2-(1-(Cyclopropylsulfonyl)-1H-pyrazol-4-yl)pyrimidin-4-yl)amino)-N-(2,2-difluoroethyl)-4-((((1r,4r)-4-((dimethylamino)methyl)cyclohexyl)methyl)amino)nicotinamide The title compound as an off white solid (7 mg) was prepared in the same fashion as Step 2 in Reference Example 1, except that 6-chloro-N-(2,2-difluoroethyl)-4-((((1r,4r)-4-((dimethylamino)methyl)cyclohexyl)methyl)amino)nicotinamide (44 mg, 0.113 mmol) prepared in Step 3 was used instead of 4-((2-chloro-5-(cyclopropanecarbonyl)-4-pyridyl)amino)cyclohexanone. $^1$H-NMR (CDCl$_3$, 400 MHz) δ 8.66 (s, 1H), 8.44 (d, 2H), 8.36 (t, 1H), 8.26 (s, 1H), 7.49 (s, 1H), 7.29 (s, 1H), 6.96 (s, 1H), 6.27 (t, 1H), 5.98 (tt, 1H), 3.88-3.75 (m, 2H), 3.12 (t, 2H), 2.87-2.80 (m, 1H), 2.23 (s, 6H), 2.12 (d, 2H), 1.96-1.85 (m, 4H), 1.56-1.41 (m, 3H), 1.25-1.18 (m, 2H), 1.18-1.06 (m, 2H), 1.01-0.89 (m, 2H); MS (ESI) m/z=619.2 (M+H)$^+$ Example 82. (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(3,3-difluoroazetidin-1-yl)methanone Step 1. (4,6-Dichloro-3-pyridyl)-(3,3-difluoroazetidin-1-yl)methanone The title compound as a solid (449 mg) was prepared in the same fashion as Reference Example 3 except that 3,3-difluoroazetidine HCl (337 mg, 2.604 mmol) was used instead of 2-fluoroethylamine HCl. MS (ESI) m/z=268.0 (M+H)$^+$ Step 2. tert-Butyl ((((1r,4r)-4-(((2-chloro-5-(3,3-difluoroazetidine-1-carbonyl)pyridin-4-yl)amino)methyl)cyclohexyl)methyl)carbamate The title compound as an off-white solid (250 mg) was prepared in the same fashion as Step 1 in Reference Example 2, except that (4,6-dichloro-3-pyridyl)-(3,3-difluoroazetidin-1-yl)methanone (200 mg, 0.749 mmol) prepared in Step 1 was used instead of cyclopropyl-(4,6-dichloro-3-pyridyl)methanone. MS (ESI) m/z=473.2 (M+H)$^+$ Step 3. (4-((((1r,4r)-4-(Aminomethyl)cyclohexyl)methyl)amino)-6-chloropyridin-3-yl)(3,3-difluoroazetidin-1-yl)methanone The title compound as a colorless oil (140 mg) was prepared in the same fashion as Step 2 in Reference Example 2, except that tert-butyl ((((1r,4r)-4-(((2-chloro-5-(3,3-difluoroazetidine-1-carbonyl)pyridin-4-yl)amino)methyl)cyclohexyl)methyl)carbamate (250 mg, 0.529 mmol) prepared in Step 2 was used instead of tert-butyl ((((1r,4r)-4-(((2-chloro-5-(cyclopropanecarbonyl)pyridin-4-yl)amino)methyl)cyclohexyl)methyl)carbamate. MS (ESI) m/z=373.2 (M+H)$^+$ Step 4. (6-Chloro-4-((((1r,4r)-4-((dimethylamino)methyl)cyclohexyl)methyl)amino)pyridin-3-yl)(3,3-difluoroazetidin-1-yl)methanone The title compound as a colorless oil (80 mg) was prepared in the same fashion as Step 3 in Reference Example 2, except that (4-((((1r,4r)-4-(aminomethyl)cyclohexyl)methyl)amino)-6-chloropyridin-3-yl)(3,3-difluoroazetidin-1-yl)methanone (140 mg, 0.375 mmol) prepared in Step 3 was used instead of (4-((((1r,4r)-4-(aminomethyl)cyclohexyl)methyl)amino)-6-chloropyridin-3-yl)(cyclopropyl)methanone. MS (ESI) m/z=401.2 (M+H)$^+$ Step 5. (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(3,3-difluoroazetidin-1-yl)methanone The title compound as an off white solid (13 mg) was prepared in the same fashion as Step 2 in Reference Example 1, except that (6-chloro-4-((((1r,4r)-4-((dimethylamino)methyl)cyclohexyl)methyl)amino)pyridin-3-yl)(3,3-difluoroazetidin-1-yl)methanone (45 mg, 0.113 mmol) prepared in Step 4 was used instead of 4-((2-chloro-5-(cyclopropanecarbonyl)-4-pyridyl)amino)cyclohexanone. $^1$H-NMR (CDCl$_3$, 400 MHz) δ 8.65 (s, 1H), 8.44 (d, 2H), 8.14-8.02 (m, 2H), 7.84 (s, 1H), 7.30 (s, 1H), 6.97 (s, 1H), 4.57 (t, 4H), 3.09 (t, 2H), 2.86-2.79 (m, 1H), 2.22 (s, 6H), 2.11 (d, 2H), 1.96-1.81 (m, 4H), 1.72-1.61 (m, 1H), 1.55-1.40 (m, 3H), 1.24-1.17 (m, 2H), 1.17-1.04 (m, 2H), 1.01-0.88 (m, 2H); MS (ESI) m/z=631.2 (M+H)$^+$ Example 83. 6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)-N-(2-fluoroethyl)nicotinamide Step 1. tert-Butyl ((((1r,4r)-4-(((2-chloro-5-((2-fluoroethyl)carbamoyl)pyridin-4-yl)amino)methyl)cyclohexyl)methyl)carbamate The title compound as an off-white solid (129 mg) was prepared in the same fashion as Step 1 in Reference Example 2, except that 4,6-dichloro-N-(2-fluoroethyl)pyridine-3-carboxamide (150 mg, 0.633 mmol) prepared in Reference Example 3 was used instead of cyclopropyl-(4,6-dichloro-3-pyridyl)methanone. MS (ESI) m/z=443.2 (M+H)$^+$ Step 2. 6-Chloro-4-((((1r,4r)-4-((dimethylamino)methyl)cyclohexyl)methyl)amino)-N-(2-fluoroethyl)nicotinamide The title compound as a colorless oil (50 mg) was prepared in the same fashion as Step 2 in Example 63, except that tert-butyl (((1r,4r)-4-(((2-chloro-5-((2-fluoroethyl)carbamoyl)pyridin-4-yl)amino)methyl)cyclohexyl)methyl)carbamate (129 mg, 0.291 mmol prepared in Step 1 was used instead of tert-butyl (((1r,4r)-4-(((5-acetyl-2-chloropyridin-4-yl)amino)methyl)cyclohexyl)methyl)carbamate. MS (ESI) m/z=371.2 (M+H)$^+$ Step 3. 6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)-N-(2-fluoroethyl)nicotinamide The title compound as an off white solid (11 mg) was prepared in the same fashion as Step 2 in Reference Example 1, except that 6-chloro-4-((((1r,4r)-4-((dimethylamino)methyl)cyclohexyl)methyl)amino)-N-(2-fluoroethyl)nicotinamide (45 mg, 0.113 mmol) prepared in Step 2 was used instead of 4-((2-chloro-5-(cyclopropanecarbonyl)-4-pyridyl)amino)cyclohexanone. $^1$H-NMR (CDCl$_3$, 400 MHz) δ 8.66 (s, 1H), 8.45 (d, 2H), 8.39 (t, 1H), 8.26 (s, 1H), 7.41 (s, 1H), 7.31 (d, 1H), 6.91 (s, 1H), 6.38 (t, 1H), 4.68 (t, 1H), 4.56 (t, 1H), 3.79 (q, 1H), 3.72 (q, 1H), 3.12 (t, 2H), 2.87-2.79 (m, 1H), 2.20 (s, 6H), 2.08 (d, 2H), 1.98-1.83 (m, 4H), 1.75-1.65 (m, 1H), 1.56-1.50 (m, 2H), 1.49-1.40 (m, 1H), 1.25-1.18 (m, 2H), 1.12-1.04 (m, 2H), 1.01-0.88 (m, 2H); MS (ESI) m/z=601.2 (M+H)$^+$ Example 84. N$^2$-(2-(1-(Cyclopropylsulfonyl)-1H-pyrazol-4-yl)pyrimidin-4-yl)-5-(3,4-dihydro-2H-pyran-6-yl)-N$^4$-isopropylpyridine-2,4-diamine Step 1. 2-Chloro-5-(3,4-dihydro-2H-pyran-6-yl)-N-isopropylpyridin-4-amine To a solution of 2-chloro-5-iodo-N-isopropylpyridin-4-amine (250 mg, 0.843 mmol) in 1,4-dioxane (5 mL) were added potassium 3,4-dihydro-2H-pyran-6-yl(trifluoro)boranuide (182 mg, 0.957 mmol), [1,1'-Bis(diphenylphosphino)ferrocene]dichloropalladium(II), complex with dichloromethane (34 mg, 0.040 mmol) and 2M K$_2$CO$_3$ solution (1.26 mL, 2.530 mmol). The reaction mixture was stirred at 90° C. for 18 hours. The reaction mixture was cooled to room temperature, quenched with water, and then extracted with DCM. The organic layer was dried over MgSO$_4$, filtered, and concentrated. The residue was purified by flash column chromatography (EA/n-Hex=40%) to yield 2-chloro-5-(3,4-dihydro-2H-pyran-6-yl)-N-isopropylpyridin-4-amine as a colorless liquid (124 mg). MS (ESI) m/z=253.1 (M+H)$^+$ Step 2. N$^2$-(2-(1-(Cyclopropylsulfonyl)-1H-pyrazol-4-yl)pyrimidin-4-yl)-5-(3,4-dihydro-2H-pyran-6-yl)-N$^4$-isopropylpyridine-2,4-diamine The title compound as a pale yellow oil (5 mg) was prepared in the same fashion as Step 2 in Reference Example 1, except that 2-chloro-5-(3,4-dihydro-2H-pyran-6-yl)-N-isopropyl-pyridin-4-amine (52 mg, 0.207 mmol) prepared in Step 1 was used instead of 4-((2-chloro-5-(cyclopropanecarbonyl)-4-pyridyl)amino)cyclohexanone. $^1$H-NMR (CDCl$_3$, 400 MHz) δ 8.64 (s, 1H), 8.50 (s, 1H), 8.37 (d, 1H), 7.93 (s, 1H), 7.88 (s, 1H), 7.12-7.09 (m, 2H), 5.43 (d, 1H), 5.02 (t, 1H), 4.18 (t, 2H), 3.80-3.72 (m, 1H), 2.86-2.79 (m, 1H), 2.26-2.22 (m, 2H), 1.98-1.93 (m, 2H), 1.54-1.50 (m, 2H), 1.32 (d, 6H), 1.24-1.18 (m, 2H); MS (ESI) m/z=482.2 (M+H)$^+$ Example 85. (1-(2-((2-(1-(Cyclopropylsulfonyl)-1H-pyrazol-4-yl)pyrimidin-4-yl)amino)-5-fluoropyridin-4-yl)-4-methylpiperidin-4-yl)methanol Step 1. (1-(2-Chloro-5-fluoropyridin-4-yl)-4-methylpiperidin-4-yl)methanol The title compound as a white solid (120 mg) was prepared in the same fashion as Step 1 in Example 1, except that (4-methylpiperidin-4-yl)methanol (150 mg, 1.16 mmol) and 2-chloro-5-fluoro-4-iodo-pyridine (272 mg, 1.06 mmol) were used instead of isopropylamine and cyclopropyl(4,6-dichloropyridin-3-yl)methanone. $^1$H-NMR (CDCl$_3$, 400 MHz) δ 7.85 (d, 1H), 6.65 (d, 1H), 3.45-3.38 (m, 4H), 3.17-3.10 (m, 2H), 3.04 (brs, 1H), 1.66 (m, 2H), 1.42 (m, 2H), 1.00 (s, 3H); MS (ESI) m/z=259.1 (M+H)$^+$ Step 2. (1-(2-((2-(1-(Cyclopropylsulfonyl)-1H-pyrazol-4-yl)pyrimidin-4-yl)amino)-5-fluoropyridin-4-yl)-4-methylpiperidin-4-yl)methanol The title compound as an off-white solid (8 mg) was prepared in the same fashion as Step 2 in Example 1, except that (1-(2-chloro-5-fluoropyridin-4-yl)-4-methylpiperidin-4-yl)methanol (88 mg, 0.34 mmol) prepared in Step 1 was used instead of (6-chloro-4-(isopropylamino)-3-pyridyl)cyclopropylmethanone. $^1$H-NMR (DMSO-d$_6$, 400 MHz) δ 10.08 (s, 1H), 8.62 (s, 1H), 8.43-8.39 (m, 2H), 8.26 (s, 1H), 8.00 (d, 1H), 7.71 (m, 1H), 7.32 (m, 1H), 3.42 (m, 2H), 3.20-3.16 (m, 5H), 1.63 (m, 2H), 1.33-1.24 (m, 6H), 0.95 (s, 3H); MS (ESI) m/z=488.2 (M+H)$^+$ Example 86. Cyclopropyl(6-((2-(1-(cyclopropylsulfonyl)-1H-pyrazol-4-yl)pyrimidin-4-yl)amino)-4-(((1s,4s)-4-hydroxy-(4-hydroxymethyl)cyclohexyl)amino)pyridin-3-yl)methanone Step 1. (6-Chloro-4-(((1s,4s)-4-hydroxy-4-(hydroxymethyl)cyclohexyl)amino)pyridin-3-yl)(cyclopropyl)methanone The title compound as a solid (238 mg) was prepared in the same fashion as Step 1 in Example 1 except that (1s,4s)-4-amino-1-(hydroxymethyl)cyclohexan-1-ol (202 mg, 1.389 mmol) was used instead of isopropylamine. $^1$H-NMR (CDCl$_3$, 400 MHz) δ 9.21 (d, 1H), 8.80 (s, 1H), 6.56 (s, 1H), 3.47 (s, 2H), 3.36-3.27 (m, 1H), 3.22 (brs, 1H), 2.70 (brs, 1H), 2.59-2.52 (m, 1H), 1.91-1.67 (m, 6H), 1.42 (dt, 2H), 1.20-1.16 (m, 2H), 1.04-0.99 (m, 2H); MS (ESI) m/z=325.1 (M+H)$^+$ Step 2. Cyclopropyl(6-((2-(1-(cyclopropylsulfonyl)-1H-pyrazol-4-yl)pyrimidin-4-yl)amino)-4-(((1s,4s)-4-hydroxy-4-(hydroxymethyl)cyclohexyl)amino)pyridin-3-yl)methanone The title compound (87 mg) was prepared in the same fashion as Step 2 in Example 1, except that (6-chloro-4-

(((1s,4s)-4-hydroxy-4-(hydroxymethyl)cyclohexyl)amino) pyridin-3-yl)(cyclopropyl)methanone (122 mg, 0.377 mmol) prepared in Step 1 was used instead of (6-chloro-4-(isopropylamino)-3-pyridyl)cyclopropylmethanone. $^1$H-NMR (DMSO-$d_6$, 400 MHz) δ 9.18 (d, 1H), 8.97 (s, 1H), 8.65 (s, 1H), 8.49 (d, 1H), 8.45 (s, 1H), 7.60 (s, 1H), 7.23 (s, 1H), 4.49 (t, 1H), 4.06 (s, 1H), 3.28-3.22 (m, 1H), 3.19 (d, 2H), 2.92-2.86 (m, 1H), 1.83-1.81 (m, 2H), 1.60-1.40 (m, 6H), 1.36-1.32 (m, 2H), 1.32-1.27 (m, 2H), 1.03-0.99 (m, 2H), 0.96-0.93 (m, 2H); MS (ESI) m/z=554.2 (M+H)$^+$

Example 87. Cyclopropyl(6-((2-(1-(cyclopropylsulfonyl)-1H-pyrazol-4-yl)pyrimidin-4-yl)amino)-4-((4-fluoro-4-(hydroxymethyl)cyclohexyl)amino)pyridin-3-yl)methanone

Step 1. (6-Chloro-4-((4-fluoro-4-(hydroxymethyl)cyclohexyl)amino)pyridin-3-yl)(cyclopropyl)methanone The title compound as a solid (202 mg) was prepared in the same fashion as Step 1 in Example 1 except that (4-amino-1-fluoro-cyclohexyl)methanol (204 mg, 1.389 mmol) was used instead of isopropylamine. $^1$H-NMR (CDCl$_3$, 400 MHz) δ 9.24 (d, 1H), 8.85 (s, 1H), 6.58 (s, 1H), 3.62 (d, 2H), 3.38-3.36 (m, 1H), 2.61-2.55 (m, 1H), 2.15-2.09 (m, 2H), 2.01-1.98 (m, 2H), 1.73-1.43 (m, 4H), 1.23-1.21 (m, 2H), 1.07-1.04 (m, 2H); MS (ESI) m/z=327.1 (M+H)$^+$

Step 2. Cyclopropyl(6-((2-(1-(cyclopropylsulfonyl)-1H-pyrazol-4-yl)pyrimidin-4-yl)amino)-4-((4-fluoro-4-(hydroxymethyl)cyclohexyl)amino)pyridin-3-yl)methanone The title compound (79 mg) was prepared in the same fashion as Step 2 in Example 1, except that (6-chloro-4-((4-fluoro-4-(hydroxymethyl)cyclohexyl)amino)pyridin-3-yl)(cyclopropyl)methanone (136 mg, 0.415 mmol) prepared in Step 1 was used instead of (6-chloro-4-(isopropylamino)-3-pyridyl)cyclopropylmethanone. $^1$H-NMR (DMSO-$d_6$, 400 MHz) δ 10.28 (s, 1H), 9.23 (d, 1H), 9.01 (s, 1H), 8.67 (s, 1H), 8.49 (d, 1H), 8.48 (s, 1H), 7.54 (d, 1H), 7.33 (s, 1H), 4.94 (t, 1H), 3.56 (s, 1H), 3.40 (dd, 2H), 3.28-3.22 (m, 1H), 2.93-2.86 (m, 1H), 1.98-1.94 (m, 2H), 1.88-1.85 (m, 2H), 1.60-1.46 (m, 4H), 1.37-1.33 (m, 2H), 1.27-1.22 (m, 2H), 1.03-1.01 (m, 2H), 0.96-0.93 (m, 2H); MS (ESI) m/z=556.1 (M+H)$^+$

Example 88. Cyclopropyl(6-((2-(1-(cyclopropylsulfonyl)-1H-pyrazol-4-yl)pyrimidin-4-yl)amino)-4-((((1r,4r)-4-(methylamino)cyclohexyl)methyl)amino)pyridin-3-yl)methanone

Step 1. (6-Chloro-4-((((1r,4r)-4-(methylamino)cyclohexyl)methyl)amino)pyridin-3-yl)(cyclopropyl)methanone The title compound as a solid (142 mg) was prepared in the same fashion as Step 1 in Example 1 except that tert-butyl ((1r,4r)-4-(aminomethyl)cyclohexyl)(methyl)carbamate (200 mg, 0.827 mmol) was used instead of isopropylamine. $^1$H-NMR (CDCl$_3$, 400 MHz) δ 9.25 (s, 1H), 8.83 (s, 1H), 6.55 (s, 1H), 3.03 (t, 2H), 2.72 (s, 3H), 2.62-2.56 (m, 1H), 1.94-1.90 (m, 2H), 1.76-1.74 (m, 2H), 1.65-1.58 (m, 2H), 1.52-1.47 (m, 11H), 1.23-1.11 (m, 4H), 1.07-1.03 (m, 2H);

Step 2. Cyclopropyl(6-((2-(1-(cyclopropylsulfonyl)-1H-pyrazol-4-yl)pyrimidin-4-yl)amino)-4-((((1r,4r)-4-(methylamino)cyclohexyl)methyl)amino)pyridin-3-yl)methanone To a solution of 2-(1-cyclopropylsulfonylpyrazol-4-yl) pyrimidin-4-amine (70 mg, 0.260 mmol) 2-(1-cyclopropylsulfonylpyrazol-4-yl)pyrimidin-4-amine (70 mg, 0.2600 mmol)_XXXXX_ in 1,4-dioxane (6 mL) 1,4-Dioxane (6 mL) _XXXXX_ were added tris(dibenzylideneacetone)dipalladium(0) (24 mg, 0.030 mmol) Tris(dibenzylideneacetone)dipalladium(0) (24.16 mg, 0.0300 mmol) _XXXXX_, XPhos (25 mg, 0.050 mmol) XPhos (25.16 mg, 0.0500 mmol) _XXXXX_, cesium carbonate (215 mg, 0.660 mmol) Cesium carbonate (214.94 mg, 0.6600 mmol) _XXXXX_ _XXXXX_ and (6-chloro-4-((((1r,4r)-4-(methylamino)cyclohexyl)methyl)amino)pyridin-3-yl)(cyclopropyl)methanone (122 mg, 0.290 mmol) prepared in Step 1 tert-butyl N-[4-[[[2-chloro-5-(cyclopropanecarbonyl)-4-pyridyl]amino]methyl]cyclohexyl]-N-methyl-carbamate (122.47 mg, 0.2900 mmol) _XXXXX_. The reaction mixture was stirred at rt for 30 minutes, and then heated to 90° C. 90° C. _XXXXX_ for 6 hours 6 hour(s) _XXXXX_. The reaction mixture was filtered through Celite, concentrated, diluted with DCM, washed water, and the organic layer was concentrate in-vacuo. The crude residue was purified by silica gel column chromatography (MeOH/MC=0-10%), and then concentrated. The residue was diluted with DCM (5 mL), added TFA (0.5 mL), and stirred at room temperature overnight. The reaction mixture was concentrated under reduced pressure and the residue was added DCM. The residue was basified by 1N NaOH solution (>pH8), washed water, dried over MgSO$_4$, and then concentrated under reduced pressure. The crude residue was diluted in EA, slurried with isopropyl ether for an hour, and then filtered to give cyclopropyl(6-((2-(1-(cyclopropylsulfonyl)-1H-pyrazol-4-yl)pyrimidin-4-yl)amino)-4-((((1r,4r)-4-(methylamino)cyclohexyl)methyl)amino)pyridin-3-yl)methanone (78 mg, 0.141 mmol) as a pale yellow solid. $^1$H-NMR (CDCl$_3$, 400 MHz) δ 9.32 (s, 1H), 8.88 (d, 1H), 8.67 (d, 1H), 8.47-8.45 (m, 2H), 7.58 (s, 1H), 7.04 (s, 1H), 3.17-3.14 (m, 2H), 2.87-2.81 (m, 1H), 2.64-2.59 (m, 1H), 2.44 (d, 3H), 2.38-2.32 (m, 1H), 2.03-2.00 (m, 2H), 1.94-1.91 (m, 2H), 1.60-1.51 (m, 4H), 1.26-1.18 (m, 4H), 1.08-1.03 (m, 1H), 1.03-1.00 (m, 2H); MS (ESI) m/z=551.2 (M+H)$^+$

Example 89. Cyclopropyl(6-((2-(1-(cyclopropylsulfonyl)-1H-pyrazol-4-yl)pyrimidin-4-yl)amino)-4-((((1r,4r)-4-((methylamino)methyl)cyclohexyl)methyl)amino)pyridin-3-yl)methanone

Step 1. (6-Chloro-4-((((1r,4r)-4-((methylamino)methyl)cyclohexyl)methyl)amino)pyridin-3-yl)(cyclopropyl)methanone The title compound as a solid (202 mg) was prepared in the same fashion as Step 1 in Example 1 except that tert-butyl (((1r,4r)-4-(aminomethyl)cyclohexyl)methyl)(methyl)carbamate (212 mg, 0.827 mmol) was used instead of isopropylamine. $^1$H-NMR (CDCl$_3$, 400 MHz) δ 9.24 (s, 1H), 8.83 (s, 1H), 6.56 (s, 1H), 3.07-3.01 (m, 4H), 2.85 (s, 3H), 2.62-2.56 (m, 1H), 1.89-1.87 (m, 2H), 1.76-1.74 (m, 2H), 1.61-1.56 (m, 2H), 1.46 (s, 9H), 1.23-1.19 (m, 2H), 1.07-0.98 (m, 6H);

Step 2. Cyclopropyl(6-((2-(1-(cyclopropylsulfonyl)-1H-pyrazol-4-yl)pyrimidin-4-yl)amino)-4-((((1r,4r)-4-((methylamino)methyl)cyclohexyl)methyl)amino)pyridin-3-yl)methanone The title compound (26 mg) was prepared in the same fashion as Step 2 in Example 88, except that (6-chloro-4-(((((1r,4r)-4-((methylamino)methyl)cyclohexyl)methyl)amino)pyridin-3-yl)(cyclopropyl)methanone (127 mg, 0.290 mmol) prepared in Step 1 was used instead of (6-chloro-4-((((1r,4r)-4-(methylamino)cyclohexyl)methyl)amino)pyridin-3-yl)(cyclopropyl)methanone. $^1$H-NMR (CDCl$_3$, 400 MHz) δ 9.30 (t, 1H), 8.88 (s, 1H), 8.67 (s, 1H), 8.46 (d, 2H), 7.56 (s, 1H), 7.29 (d, 1H), 7.01 (s, 1H), 3.14 (t, 2H), 2.86-2.80 (m, 1H), 2.63-2.58 (m, 1H), 2.44-2.43 (m, 5H), 1.93-1.90 (m, 2H), 1.86-1.83 (m, 2H), 1.56-1.45 (m, 6H), 1.23-1.19 (m, 4H), 1.07-1.03 (m, 2H), 1.03-0.97 (m, 2H); MS (ESI) m/z=565.2 (M+H)$^+$ Biological Assays 1. Biochemical EGFR Inhibition Assays Biochemical EGFR kinase assays were conducted using Lance Ultra time-resolved fluorescence resonance energy transfer (TR-FRET) technology from Perkin-Elmer. Compounds of the invention were initially diluted to 20 mM in 100% DMSO for storage and made into kinase buffer solution to create a compound concentration ranging from 0.003 μM and 10 μM.

Briefly, each EGFR enzyme wildtype, double mutant [del19/C797S and L858R/C797S], triple mutant [del19/T790M/C797S and L858R/T790M/C797S], serial diluted EGFR inhibitors, substrate of ULight-poly-GT peptide (PerkinElmer; TRF0100-M) and different concentrations of ATP (Km and 100 μM final assay concentration) were mixed in kinase assay buffer (50 mM HEPES pH 7.4, 10 mM MgCl$_2$, 1 mM EGTA, 2 mM DTT and 0.01% Tween-20) and were added to a 384-well plate (Optiplate™ 384, white, PerkinElmer; 6007290).

Each kinase reactions were incubated at room temperature for 1 hour and then stopped by the addition of 4 μL of stop solution (10 mM EDTA). The specific Europium-labeled-anti-phosphopeptide antibody (PerkinElmer, AD0069) diluted in LANCE detection buffer was then added to a final concentration of 2 nM. After 60 minutes incubation at room temperature the LANCE signal was measured on an EnVision Multilabel Reader (Perkin-Elmer). Excitation wavelength was set at 320 nm and emission monitored at 615 nm (donor) and 665 nm (acceptor). The IC$_{50}$ values were determined using GraphPad prism software (GraphPad Software, Inc., San Diego, CA, USA).

The IC$_{50}$ values of compounds of formula (I) on the activity of each EGFR kinase evaluated as above are shown in Tables 3 to 5 below.

TABLE 3

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 1 | 3.8 | | 1.1 | | 4.5 | | 84.3 | | 565.9 | |
| 2 | 72.0 | | | | 535.9 | | | | | |
| 3 | 0.9 | | 5.4 | | 232.3 | | | | 4205.0 | |
| 4 | 1.3 | | 11.6 | | 83.6 | | | | 2399.0 | |
| 5 | 1.8 | | 18.0 | | 132.1 | | | | 2970.0 | |
| 6 | 0.6 | | 4.5 | | 78.0 | | | | 890.0 | |
| 7 | 0.5 | | 2.7 | | 49.2 | | | | 425.6 | |
| 8 | 0.4 | | 1.4 | | 61.6 | | 292.5 | | 471.2 | |
| 9 | 0.7 | | 2.5 | | 70.7 | | 479.1 | | 528.1 | |
| 10 | 2.1 | | 13.7 | | 553.1 | | | | 1167.0 | |
| 11 | 0.4 | | 2.3 | | 58.9 | | | | 187.8 | |
| 12 | 0.4 | | 0.6 | | 58.2 | | | | 228.3 | |
| 13 | 0.2 | | 0.2 | | 4.5 | | 61.7 | | 28.2 | |
| 14 | 4.7 | | 31.9 | | 458.6 | | | | 3396.0 | |
| 15 | 0.5 | | 1.2 | | 9.9 | | | | 199.0 | |
| 16 | 2.3 | | 0.4 | | 13.2 | | 30.8 | | 175.8 | |
| 17 | 10.9 | | 15.5 | | 1.0 | | | | | |
| 18 | 13.5 | | 17.2 | | 1.0 | | | | | |
| 19 | 3.1 | | 3.8 | | 159.4 | | | | 681.5 | |
| 20 | 2.2 | | 3.9 | | 414.9 | | | | 238.7 | |
| 21 | 0.4 | | 1.1 | | 72.3 | | 16.4 | | 63.5 | |
| 22 | | 0.9 | | 1.1 | | 14.0 | | 33.2 | | >10000 |
| 23 | | 0.7 | | 0.5 | | 2.4 | | 6.4 | | 3412.0 |
| 24 | | 1.5 | | 4.4 | | 70.9 | | 79.1 | | >10000 |
| 25 | | 0.9 | | 1.0 | | 11.8 | | 29.4 | | >10000 |
| 26 | | 2.9 | | 3.3 | | 55.3 | | 117.8 | | >10000 |
| 27 | | 1.3 | | 1.5 | | 19.5 | | 53.4 | | >10000 |
| 28 | | 2.6 | | 32.1 | | 176.0 | | 234.4 | | >10000 |
| 29 | | 1.8 | | 10.0 | | 3.5 | | 120.4 | | >10000 |
| 30 | | 2.1 | | 2.7 | | 19.7 | | 16.8 | | >10000 |

TABLE 4

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 31 | | 0.6 | | 2.1 | | 26.6 | | 51.7 | | >10000 |
| 32 | | 1.2 | | 2.0 | | 51.1 | | 54.7 | | >10000 |
| 33 | 1.0 | 0.8 | 0.3 | 0.8 | 1.1 | 1.7 | 0.9 | 6.5 | 13.9 | >10000 |
| 34 | | 2.0 | | 5.3 | | 123.7 | | 397.5 | | >10000 |
| 35 | | 5.2 | | 23.1 | | 602.5 | | 543.4 | | >10000 |
| 36 | | 0.5 | | 0.9 | | 5.4 | | 15.5 | | >10000 |
| 37 | 1.0 | 1.2 | 0.4 | 2.0 | 36.9 | 79.9 | 9.7 | 168.1 | 112.8 | >10000 |
| 38 | | 2.7 | | 9.9 | | 231.0 | | 199.7 | | >10000 |
| 39 | 2.9 | 3.8 | 1.9 | 5.2 | 38.4 | 38.8 | 19.0 | 450.9 | 469.7 | >10000 |
| 40 | 0.4 | 0.6 | 0.2 | 1.5 | 3.1 | 16.3 | 5.1 | 189.3 | 64.5 | >10000 |
| 41 | 1.6 | | | 5.6 | | 47.7 | | 443.6 | | 145.0 |
| 42 | 1.0 | | | 10.5 | | 212.8 | | | | 122.8 |
| 43 | 1.3 | | | 0.5 | | 10.5 | | 24.0 | | 64.1 |
| 44 | 9.0 | | | | | 242.2 | | | | 795.7 |
| 45 | 0.9 | | | 3.1 | | 205.1 | | | | 751.5 |
| 46 | 0.6 | | | 7.3 | | 290.3 | | 470.7 | | 1407.0 |
| 47 | 0.1 | | | 0.6 | | 10.5 | | 51.3 | | 144.7 |
| 48 | 0.8 | 1.0 | 0.5 | 2.4 | 15.7 | 4.4 | 26.2 | 109.5 | 552.9 | >10000 |
| 49 | 0.4 | 0.4 | 0.2 | 0.7 | 2.6 | 1.2 | 4.0 | 21.1 | 181.1 | >10000 |
| 50 | 1.6 | 2.9 | 1.1 | 6.9 | 17.2 | 8.8 | 42.8 | 157.4 | 1170.0 | >10000 |
| 51 | 1.6 | 1.8 | 1.1 | 4.5 | 45.4 | 18.9 | 47.1 | 407.4 | 1243.0 | >10000 |
| 52 | | 1.1 | | 1.8 | | 26.0 | | 15.2 | | >10000 |
| 53 | | 0.5 | | 0.5 | | 1.8 | | 1.5 | | 1896.0 |
| 54 | | 1.2 | | 3.7 | | 66.1 | | 33.8 | | >10000 |
| 55 | | 1.0 | | 1.9 | | 35.7 | | 85.0 | | >10000 |
| 56 | | 1.0 | | 1.2 | | 7.6 | | 12.2 | | 6301.0 |
| 57 | | 0.6 | | 1.0 | | 18.0 | | 10.7 | | >10000 |
| 58 | 0.1 | | 0.1 | | 0.4 | | 2.4 | | 3.6 | |
| 59 | 1.2 | | 5.7 | | 207.1 | | 67.9 | | 136.0 | |
| 60 | 5.4 | | 3.5 | | | | 115.4 | | 429.6 | |

TABLE 5

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 61 | 5.7 | | | | | | 122.8 | | 414.7 | |
| 62 | 9.8 | | 9.4 | | 363.3 | | | | | |
| 63 | 0.0 | | 0.1 | | 2.0 | | 1.1 | | 4.8 | |
| 64 | 1.5 | | 6.0 | | 54.0 | | 23.4 | | 92.7 | |
| 65 | 0.7 | | 5.8 | | 52.5 | | | | 388.8 | |
| 66 | 0.1 | | 0.4 | | 11.1 | | 100.6 | | 147.7 | |
| 67 | 0.2 | | 0.2 | | 0.7 | | 4.1 | | 9.3 | |
| 68 | 1.0 | | 0.5 | | 1.0 | | 11.8 | | 14.9 | |
| 69 | 0.1 | | 0.1 | | 0.8 | | 9.2 | | 7.5 | |
| 70 | 0.3 | | 0.4 | | 2.7 | | 14.4 | | 24.2 | |
| 71 | 0.2 | | 0.3 | | 1.0 | | 10.1 | | 20.7 | |
| 72 | 1.0 | | 1.5 | | 7.2 | | 45.8 | | 2040.0 | |
| 73 | 17.4 | | 3.1 | | 16.1 | | | | 691.5 | |
| 74 | 6.3 | 4.2 | | 5.7 | 94.6 | 181.9 | | 429.6 | 392.6 | >10000 |
| 75 | | 0.7 | | 1.3 | | 14.5 | | 30.5 | | >10000 |
| 76 | 0.2 | 0.6 | 0.1 | 0.7 | 0.9 | 2.3 | 2.7 | 28.9 | 12.0 | >10000 |
| 77 | 0.2 | 0.9 | 0.1 | 1.6 | 5.6 | 19.3 | 9.0 | 144.6 | 57.4 | >10000 |
| 78 | 14.9 | | | | 225.2 | | | | 1137.0 | |
| 79 | | 0.4 | | 0.9 | | 6.8 | | 25.4 | | >10000 |
| 80 | | 0.8 | | 2.4 | | 72.8 | | 170.5 | | >10000 |
| 81 | 0.6 | 0.8 | | 0.8 | 2.4 | 4.4 | 2.5 | 36.6 | 9.1 | 39730 |
| 82 | 2.8 | | | | 24.6 | | | | 76.2 | |
| 83 | | 0.4 | | 0.7 | | 2.8 | | 18.5 | | 1649.0 |
| 84 | | 4.5 | | | | 106.7 | | 523.2 | | >10000 |
| 85 | | 9.4 | | 21.5 | | 145.8 | | 902.5 | | >10000 |
| 86 | 0.2 | 0.2 | 0.1 | 0.3 | 1.9 | 2.9 | 4.3 | 52.9 | 47.6 | >10000 |
| 87 | | 2.2 | | 4.3 | | 25.3 | | 441.9 | | >10000 |

TABLE 5-continued

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 88 | 0.1 | 0.1 | 0.1 | 0.2 | 1.6 | 2.6 | 2.6 | 30.7 | 24.6 | 3163.0 |
| 89 | 0.2 | 0.2 | 0.1 | 0.1 | 0.5 | 0.8 | 0.7 | 7.9 | 4.9 | 532.0 |

What is claimed is:

1. A compound of formula (I) or a pharmaceutically acceptable salt thereof,

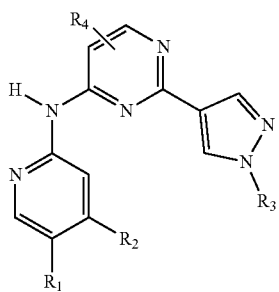

wherein
$R_1$ is selected from the group consisting of
$C_{1-6}$ alkyl optionally substituted by one or more substituents selected from the group consisting of OH, halogen, $C_{3-6}$ cycloalkyl, —$NHC_{1-6}$ alkyl, and $N(C_{1-6}$ alkyl$)_2$;
$C_{1-3}$ alkoxy;
—C(O)—$C_{1-6}$ alkyl, optionally substituted by one or more substituents selected from the group consisting of halogen, —$NHC_{1-6}$ alkyl, —$N(C_{1-6}$ alkyl$)_2$, and 4-7 membered heterocyclyl;
—C(O)—$C_{3-6}$ cycloalkyl, optionally substituted by one or more substituents selected from the group consisting of OH and halogen;
—C(O)—$C_{6-10}$ aryl optionally substituted by one or more halogens;
—C(O)-5-6 membered heteroaryl optionally substituted by one or more halogens;
—$N(C_{1-6}$ alkyl$)_2$;
—$NHC(O)C_{1-6}$ alkyl;
—$NHC(O)C_{3-6}$ cycloalkyl, optionally substituted by one or more substituents selected from the group consisting of OH and halogen;
—$C(O)NHC_{1-6}$ alkyl optionally substituted by one or more substituents selected from the group consisting of OH and halogen;
—$C(O)NHC_{3-6}$ cycloalkyl optionally substituted by one or more substituents selected from the group consisting of OH, halogen and —$N(C_{1-6}$ alkyl$)_2$;
—C(O)-3-7 membered heterocyclyl optionally substituted by one or more substituents selected from the group consisting of OH, halogen, $C_{1-6}$ alkyl, and $C_{1-6}$ hydroxyalkyl; and
4-7 membered heterocyclyl optionally substituted by one or more substituents selected from the group consisting of OH and halogen,
$R_2$ is selected from the group consisting of —$XC_{1-6}$ alkyl optionally substituted by one or more substituents selected from the group consisting of OH, halogen, and —$N(C_{1-6}$ alkyl$)_2$; and —$X(CH_2)_n$-A-$(R_{2A})_o$,
X is —NH—, —O—, bond or —C≡C—,
n is an integer of 0 to 2,
is an integer of 0 to 3,
A is selected from the group consisting of $C_{3-8}$ cycloalkyl; $C_{6-10}$ aryl; 4-11 membered heterocyclyl; and 5-6 membered heteroaryl,
$R_{2A}$ is independently selected from the group consisting of
H;
halogen;
OH;
$NH_2$;
$C_{1-6}$ alkyl optionally substituted by one or more substituents selected from the group consisting of OH, $NH_2$, halogen, $C_{3-6}$ cycloalkyl, $C_{1-3}$ alkoxy, —$NHC_{1-6}$ alkyl, —$NHC_{1-6}$ hydroxyalkyl, —$NHC_{1-6}$ haloalkyl, —$NHC_{3-6}$ cycloalkyl, —$N(C_{1-6}$ alkyl$)_2$, —$N(C_{1-6}$ haloalkyl$)_2$, —$NHC(O)C_{1-6}$ alkyl, —$C(O)NHC_{1-6}$ alkyl, —$C(O)N(C_{1-6}$ alkyl$)_2$, 3-7 membered heterocyclyl and 5-6 membered heteroaryl;
$C_{3-6}$ cycloalkyl;
$C_{1-3}$ alkoxy optionally substituted by one or more halogens;
—$C(O)NHC_{1-6}$ alkyl optionally substituted by one or more substituents selected from the group consisting of OH and halogen;
—$C(O)N(C_{1-6}$ alkyl$)_2$ optionally substituted by one or more substituents selected from the group consisting of OH and halogen;
—$NHC_{1-6}$ alkyl optionally substituted by one or more substituents selected from the group consisting of OH, halogen, —$NHC_{1-6}$ alkyl, —$N(C_{1-6}$ alkyl$)_2$, and 3-7 membered heterocyclyl optionally substituted by halogen or —$N(C_{1-6}$ alkyl$)_2$;
—$N(C_{1-6}$ alkyl$)_2$ where $C_{1-6}$ alkyl is optionally substituted by one or more halogens;
—NH-4-7 membered heterocyclyl optionally substituted by $C_{1-6}$ alkyl; and
4-7 membered heterocyclyl,
$R_3$ is selected from the group consisting of
H;
$C_{1-6}$ alkyl optionally substituted by one or more substituents selected from the group consisting of halogen and $C_{3-6}$ cycloalkyl;
$C_{3-6}$ cycloalkyl;
4-7 membered heterocyclyl;
—$S(O)_2C_{1-6}$ alkyl optionally substituted by one or more halogens; and
—$S(O)_2C_{3-6}$ cycloalkyl optionally substituted by one or more halogens, and
$R_4$ is selected from the group consisting of H, halogen and $C_{1-6}$ alkyl.

2. The compound of claim 1, or a pharmaceutically acceptable salt thereof,
wherein
$R_1$ is $C_{1-3}$ alkyl optionally substituted by one to three substituents selected from the group consisting of OH, F, Cl, $C_{3-6}$ cycloalkyl, —$NHC_{1-3}$ alkyl, and $N(C_{1-3}$ alkyl$)_2$; $C_{1-2}$ alkoxy; —C(O)—$C_{1-3}$ alkyl, optionally substituted by one to three substituents selected from the group consisting of F, and Cl, —$NHC_{1-3}$ alkyl, —$N(C_{1-3}$ alkyl$)_2$, and 4-7 membered heterocyclyl having one to three heteroatoms selected from a group consisting of N, O and S; —C(O)—$C_{3-6}$ cycloalkyl, optionally substituted by one to three substituents selected from the group consisting of OH and halogen; —C(O)phenyl optionally substituted by one to three F, or Cl; —C(O)-5-6 membered heteroaryl optionally substituted by one to three F, Br, Cl or I; —$N(C_{1-3}$ alkyl$)_2$; —NHC(O)$C_{1-3}$ alkyl; —NHC(O)$C_{3-6}$ cycloalkyl, optionally substituted by one to three substituents selected from the group consisting of OH, F, Br, Cl and I; —C(O)NH$C_{1-3}$ alkyl optionally substituted by one to three substituents selected from the group consisting of OH, F and Cl; —C(O)NH$C_{3-6}$ cycloalkyl optionally substituted by one or more substituents selected from the group consisting of OH, F, Br, Cl, I and —$N(C_{1-3}$ alkyl$)_2$; —C(O)-3-7 membered heterocyclyl optionally substituted by one to three substituents selected from the group consisting of OH, F, Cl, $C_{1-6}$ alkyl, and $C_{1-6}$ hydroxyalkyl; or 4-7 membered heterocyclyl.

3. The compound of claim 1, or a pharmaceutically acceptable salt thereof, wherein $R_1$ is —C(O)—$C_{1-6}$ alkyl, optionally substituted by one or more substituents selected from the group consisting of halogen, —NH$C_{1-6}$ alkyl, —$N(C_{1-6}$ alkyl$)_2$, and 4-7 membered heterocyclyl; —C(O)—$C_{3-6}$ cycloalkyl, optionally substituted by one or more substituents selected from the group consisting of OH and halogen; or —C(O)NH$C_{1-3}$ alkyl optionally substituted by one to three substituents selected from the group consisting of OH, F and Cl.

4. The compound of claim 3, or a pharmaceutically acceptable salt thereof, wherein $R_1$ is —C(O)—$C_{1-6}$ alkyl, optionally substituted by one or more
substituents selected from the group consisting of halogen, —NH$C_{1-6}$ alkyl, —$N(C_{1-6}$ alkyl$)_2$, and 4-7 membered heterocyclyl.

5. The compound of claim 3, or a pharmaceutically acceptable salt thereof, wherein $R_1$ is —C(O)—$C_{3-6}$ cycloalkyl, optionally substituted by one or more substituents selected from the group consisting of OH and halogen.

6. The compound of claim 3, or a pharmaceutically acceptable salt thereof, wherein $R_1$ is —C(O)NH$C_{1-3}$ alkyl optionally substituted by one to three substituents selected from the group consisting of OH, F and Cl.

7. The compound of claim 1, or a pharmaceutically acceptable salt thereof, wherein $R_1$ is selected from the group consisting of
—C(O)—$C_{1-6}$ alkyl, optionally substituted by one or more substituents selected from the group consisting of halogen and 4-7 membered heterocyclyl;
—C(O)—$C_{3-6}$ cycloalkyl;
—C(O)-phenyl optionally substituted by one or more halogens;
—NHC(O)$C_{3-6}$ cycloalkyl;
—C(O)NH$C_{1-6}$ alkyl optionally substituted by one or more halogens;
—C(O)NH$C_{3-6}$ cycloalkyl optionally substituted by one or more OHs;
—C(O)-3-7 membered heterocyclyl optionally substituted by one or more halogens; and
4-7 membered heterocyclyl.

8. The compound of claim 7, or a pharmaceutically acceptable salt thereof, wherein the 3-7 membered heterocyclyl or 4-7 membered heterocyclyl is tetrahydropyranyl, azetidinyl, or 3,4-dihydropyranyl.

9. The compound of claim 1, or a pharmaceutically acceptable salt thereof, wherein $R_2$ is —X$C_{1-6}$ alkyl optionally substituted by one or more substituents selected from the group consisting of OH, halogen, and —$N(C_{1-6}$alkyl$)_2$.

10. The compound of claim 1, or a pharmaceutically acceptable salt thereof, wherein $R_2$ is —X(CH$_2$)$_n$-A-(R$_{2A}$)$_o$.

11. The compound of claim 1, or a pharmaceutically acceptable salt thereof, wherein X is —NH—, —O—, or bond.

12. The compound of claim 1, or a pharmaceutically acceptable salt thereof, wherein A is $C_{3-6}$ cycloalkyl; phenyl; 4-10 membered heterocyclyl having one to three heteroatoms selected from a group consisting of N, O and S; or 5-6 membered heteroaryl having one to three heteroatoms selected from a group consisting of N, O and S.

13. The compound of claim 1, or a pharmaceutically acceptable salt thereof, wherein A is $C_{3-6}$ cycloalkyl.

14. The compound of claim 1, or a pharmaceutically acceptable salt thereof, wherein A is 4-10 membered heterocyclyl or 5-6 membered heteroaryl having one to three heteroatoms selected from a group consisting of N and 0.

15. The compound of claim 1, or a pharmaceutically acceptable salt thereof, wherein A is $C_{3-8}$ cycloalkyl, phenyl, pyrazolyl, pyridinyl, tetrahydrofuranyl, tetrahydropyranyl, thienyl, or piperidinyl.

16. The compound of claim 1, or a pharmaceutically acceptable salt thereof, wherein $R_{2A}$ is H; F; Cl; OH; NH$_2$; $C_{1-4}$ alkyl optionally substituted by one or more substituents selected from the group consisting of OH, NH$_2$, F, Cl, $C_{3-6}$ cycloalkyl, $C_{1-3}$ alkoxy, —NH$C_{1-3}$ alkyl, —NH$C_{1-3}$ hydroxyalkyl, —NH$C_{1-3}$ haloalkyl, —NH$C_{3-6}$ cycloalkyl, —$N(C_{1-3}$ alkyl$)_2$, —$N(C_{1-3}$ haloalkyl$)_2$, —NHC(O)$C_{1-3}$ alkyl, —C(O)NH$C_{1-3}$ alkyl, —C(O)N($C_{1-6}$ alkyl$)_2$, 3-7 membered heterocyclyl, and 5-6 membered heteroaryl having one to three heteroatoms selected from a group consisting of N, O and S; $C_{3-6}$ cycloalkyl; $C_{1-3}$ alkoxy optionally substituted by one to three F or Cl; —C(O)NH$C_{1-3}$ alkyl optionally substituted by one to three substituents selected from the group consisting of OH, F and Cl; —C(O)N($C_{1-3}$ alkyl$)_2$ optionally substituted by one to three substituents selected from the group consisting of OH, F and Cl; —NH$C_{1-3}$ alkyl optionally substituted by one to three substituents selected from the group consisting of OH, F, Cl, —NH$C_{1-3}$ alkyl, —$N(C_{1-3}$alkyl$)_2$, 3-6 membered heterocyclyl one to three heteroatoms selected from a group consisting of N, O and S optionally substituted by F, Cl or —$N(C_{1-3}$ alkyl$)_2$; —$N(C_{1-3}$ alkyl$)_2$ where $C_{1-3}$ alkyl is optionally substituted by one to three F or Cl; —NH-4-6 membered heterocyclyl one to three heteroatoms selected from a group consisting of N, O and S optionally substituted by $C_{1-3}$ alkyl; or 4-7 membered heterocyclyl.

17. The compound of claim 1, or a pharmaceutically acceptable salt thereof, wherein $R_{2A}$ is OH; $C_{1-6}$ alkyl optionally substituted by one or more substituents selected from the group consisting of OH, NH$_2$, halogen, $C_{3-6}$ cycloalkyl, $C_{1-3}$ alkoxy, —NH$C_{1-6}$ alkyl, —NH$C_{1-6}$ hydroxyalkyl, —NH$C_{1-6}$ haloalkyl, —NH$C_{3-6}$ cycloalkyl, —$N(C_{1-6}$ alkyl$)_2$, —$N(C_{1-6}$ haloalkyl$)_2$, —NHC(O)$C_{1-6}$ alkyl, —C(O)NH$C_{1-6}$ alkyl, —C(O)N($C_{1-6}$ alkyl$)_2$, 3-7 membered heterocyclyl, and 5-6 membered heteroaryl having one to three heteroatoms selected from a group consisting of N, O and S; —C(O)NHC$_{1-3}$ alkyl optionally substituted by one to three substituents selected from the group consisting of OH, F and Cl; or —NHC$_{1-3}$ alkyl optionally substituted by one to three substituents selected from the group consisting of OH, halogen, —NHC$_{1-3}$ alkyl, —N(C$_{1-3}$ alkyl)$_2$, 3-7 membered heterocyclyl one to three heteroatoms selected from a group consisting of N, O and S optionally substituted by halogen or —N(C$_{1-3}$ alkyl)$_2$.

18. The compound of claim 1, or a pharmaceutically acceptable salt thereof, wherein R$_{2A}$ is independently selected from the group consisting of H;
halogen;
OH;
C$_{1-6}$ alkyl optionally substituted by one or more substituents selected from the group consisting of OH, NH$_2$, halogen, C$_{3-6}$ cycloalkyl, —NHC$_{1-6}$ alkyl, —NHC$_{1-6}$ hydroxyalkyl, —NHC$_{1-6}$ haloalkyl, —NHC$_{3-6}$ cycloalkyl, —N(C$_{1-6}$alkyl)$_2$, —NHC(O)C$_{1-6}$ alkyl, 3-7 membered heterocyclyl, imidazolyl, and pyrazolyl;
—NHC$_{1-6}$ alkyl optionally substituted by one or more substituents selected from the group consisting of OH, halogen, —N(C$_{1-6}$alkyl)$_2$, and 3-7 membered heterocyclyl optionally substituted by halogen or —N(C$_{1-6}$alkyl)$_2$;
—N(C$_{1-6}$ alkyl)$_2$;
—NH-4-7 membered heterocyclyl optionally substituted by C$_{1-6}$ alkyl; and
4-7 membered heterocyclyl.

19. The compound of claim 18, or a pharmaceutically acceptable salt thereof, wherein the 3-7 membered heterocyclyl or 4-7 membered heterocyclyl is oxetanyl, piperazinyl, azetidinyl, or piperidinyl.

20. The compound of claim 1, or a pharmaceutically acceptable salt thereof, wherein R$_3$ is H, C$_{1-4}$ alkyl optionally substituted by one to three substituents selected from the group consisting of F, Cl and C$_{3-6}$ cycloalkyl; C$_{3-6}$ cycloalkyl; 4-6 membered heterocyclyl; —S(O)$_2$C$_{1-3}$ alkyl optionally substituted by one to three F or Cl; or —S(O)$_2$C$_{3-6}$ cycloalkyl optionally substituted by one to three F or Cl.

21. The compound of claim 1, or a pharmaceutically acceptable salt thereof, wherein R$_3$ is —S(O)$_2$C$_{1-3}$ alkyl optionally substituted by one to three F or Cl; or —S(O)$_2$C$_{3-6}$ cycloalkyl optionally substituted by one to three F or Cl.

22. The compound of claim 1, or a pharmaceutically acceptable salt thereof, wherein R$_3$ is selected from the group consisting of
H;
C$_{1-6}$ alkyl optionally substituted by one or more substituents selected from the group consisting of halogen and C$_{3-6}$ cycloalkyl;
C$_{3-6}$ cycloalkyl;
tetrahydrofuranyl; and
—S(O)$_2$C$_{3-6}$ cycloalkyl.

23. The compound of claim 1, or a pharmaceutically acceptable salt thereof, wherein R$_4$ is H.

24. A compound selected from the group consisting of the compounds as described below, or a pharmaceutically acceptable salt thereof:

(1) Cyclopropyl(6-((2-(1-(cyclopropylsulfonyl)-1H-pyrazol-4-yl)pyrimidin-4-yl)amino)-4-(isopropylamino)pyridin-3-yl)methanone;
(2) Cyclopropyl(4-(cyclopropylamino)-6-((2-(1-(cyclopropylsulfonyl)-1H-pyrazol-4-yl)pyrimidin-4-yl)amino)pyridin-3-yl)methanone;
(3) Cyclopropyl(6-((2-(1-(cyclopropylsulfonyl)-1H-pyrazol-4-yl)pyrimidin-4-yl)amino)-4-((2-fluoroethyl)amino)pyridin-3-yl)methanone;
(4) Cyclopropyl(6-((2-(1-(cyclopropylsulfonyl)-1H-pyrazol-4-yl)pyrimidin-4-yl)amino)-4-((4-fluorobutyl)amino)pyridin-3-yl)methanone;
(5) Cyclopropyl(6-((2-(1-(cyclopropylsulfonyl)-1H-pyrazol-4-yl)pyrimidin-4-yl)amino)-4-((4,4-difluorobutyl)amino)pyridin-3-yl)methanone;
(6) Cyclopropyl(6-((2-(1-(cyclopropylsulfonyl)-1H-pyrazol-4-yl)pyrimidin-4-yl)amino)-4-((2-(tetrahydrofuran-3-yl)ethyl)amino)pyridin-3-yl)methanone;
(7) (R)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone;
(8) (S)-Cyclopropyl(6-((2-(1-(cyclopropylsulfonyl)-1H-pyrazol-4-yl)pyrimidin-4-yl)amino)-4-((4-hydroxybutan-2-yl)amino)pyridin-3-yl)methanone;
(9) Cyclopropyl(6-((2-(1-(cyclopropylsulfonyl)-1H-pyrazol-4-yl)pyrimidin-4-yl)amino)-4-((3-hydroxypropyl)amino)pyridin-3-yl)methanone;
(10) Cyclopropyl(6-((2-(1-(cyclopropylsulfonyl)-1H-pyrazol-4-yl)pyrimidin-4-yl)amino)-4-(((tetrahydro-2H-pyran-2-yl)methyl)amino)pyridin-3-yl)methanone;
(11) (R)-Cyclopropyl(6-((2-(1-(cyclopropylsulfonyl)-1H-pyrazol-4-yl)pyrimidin-4-yl)amino)-4-((3-hydroxybutyl)amino)pyridin-3-yl)methanone;
(12) Cyclopropyl(6-((2-(1-(cyclopropylsulfonyl)-1H-pyrazol-4-yl)pyrimidin-4-yl)amino)-4-((3-hydroxy-2-methylbutan-2-yl)amino)pyridin-3-yl)methanone;
(13) Cyclopropyl(6-((2-(1-(cyclopropylsulfonyl)-1H-pyrazol-4-yl)pyrimidin-4-yl)amino)-4-((3-(hydroxymethyl)cyclopentyl)amino)pyridin-3-yl)methanone;
(14) Cyclopropyl(6-((2-(1-(cyclopropylsulfonyl)-1H-pyrazol-4-yl)pyrimidin-4-yl)amino)-4-((2-(dimethylamino)ethyl)amino)pyridin-3-yl)methanone;
(15) Cyclopropyl(6-((2-(1-(cyclopropylsulfonyl)-1H-pyrazol-4-yl)pyrimidin-4-yl)amino)-4-((((1r,4r)-4-(hydroxymethyl)cyclohexyl)methyl)amino)pyridin-3-yl)methanone;
(16) Cyclopropyl(6-((2-(1-(difluoromethyl)-1H-pyrazol-4-yl)pyrimidin-4-yl)amino)-4-((4-((dimethylamino)methyl)benzyl)amino)pyridin-3-yl)methanone;
(17) Cyclopropyl(6-((2-(1-(cyclopropylsulfonyl)-1H-pyrazol-4-yl)pyrimidin-4-yl)amino)-4-(((1-(2-fluoroethyl)-1H-pyrazol-4-yl)methyl)amino)pyridin-3-yl)methanone;
(18) Cyclopropyl(4-(((1-(cyclopropylmethyl)piperidin-4-yl)methyl)amino)-6-((2-(1-(cyclopropylsulfonyl)-1H-pyrazol-4-yl)pyrimidin-4-yl)amino)pyridin-3-yl)methanone;
(19) Cyclopropyl(6-((2-(1-(cyclopropylsulfonyl)-1H-pyrazol-4-yl)pyrimidin-4-yl)amino)-4-(((6-((dimethylamino)methyl)pyridin-3-yl)methyl)amino)pyridin-3-yl)methanone;
(20) Cyclopropyl(6-((2-(1-(cyclopropylsulfonyl)-1H-pyrazol-4-yl)pyrimidin-4-yl)amino)-4-(((5-((dimethylamino)methyl)thiophen-2-yl)methyl)amino)pyridin-3-yl)methanone;
(21) Cyclopropyl(6-((2-(1-(cyclopropylsulfonyl)-1H-pyrazol-4-yl)pyrimidin-4-yl)amino)-4-((2-(4-(dimethylamino)piperidin-1-yl)ethyl)amino)pyridin-3-yl)methanone;
(22) Cyclopropyl(6-((2-(1-(cyclopropylsulfonyl)-1H-pyrazol-4-yl)pyrimidin-4-yl)amino)-4-(((1S,3S)-3-hydroxycyclohexyl)amino)pyridin-3-yl)methanone;

(23) Cyclopropyl(6-((2-(1-(cyclopropylsulfonyl)-1H-pyrazol-4-yl)pyrimidin-4-yl)amino)-4-(((1s,4s)-4-hydroxycyclohexyl)amino)pyridin-3-yl)methanone;

(24) Cyclopropyl(6-((2-(1-(cyclopropylsulfonyl)-1H-pyrazol-4-yl)pyrimidin-4-yl)amino)-4-(((1S,3S)-3-hydroxycyclopentyl)amino)pyridin-3-yl)methanone;

(25) Cyclopropyl(6-((2-(1-(cyclopropylsulfonyl)-1H-pyrazol-4-yl)pyrimidin-4-yl)amino)-4-(((1S,3R)-3-hydroxycyclopentyl)amino)pyridin-3-yl)methanone;

(26) Cyclopropyl(6-((2-(1-(cyclopropylsulfonyl)-1H-pyrazol-4-yl)pyrimidin-4-yl)amino)-4-(((1R,3R)-3-hydroxycyclopentyl)amino)pyridin-3-yl)methanone;

(27) Cyclopropyl(6-((2-(1-(cyclopropylsulfonyl)-1H-pyrazol-4-yl)pyrimidin-4-yl)amino)-4-(((1R,3S)-3-hydroxycyclohexyl)amino)pyridin-3-yl)methanone;

(28) Cyclopropyl(6-((2-(1-(cyclopropylsulfonyl)-1H-pyrazol-4-yl)pyrimidin-4-yl)amino)-4-((3-hydroxy-2,2-dimethylpropyl)amino)pyridin-3-yl)methanone;

(29) Cyclopropyl(6-((2-(1-(cyclopropylsulfonyl)-1H-pyrazol-4-yl)pyrimidin-4-yl)amino)-4-((2-(1-hydroxycyclopropyl)ethyl)amino)pyridin-3-yl)methanone;

(30) Cyclopropyl(6-((2-(1-(cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)methanone;

(31) Cyclopropyl(6-((2-(1-(cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)methanone;

(32) Cyclopropyl-(6-((2-(1-(cyclopropylsulfonyl)-1H-pyrazol-4-yl)pyrimidin-4-yl)amino)-4-(((1s,4s)-4-(methylamino)cyclohexyl)amino)pyridin-3-yl)methanone;

(33) Cyclopropyl(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)methanone;

(34) Cyclopropyl(6-((2-(1-(cyclopropylsulfonyl)-1H-pyrazol-4-yl)pyrimidin-4-yl)amino)-4-((tetrahydro-2H-pyran-3-yl)amino)pyridin-3-yl)methanone;

(35) Cyclopropyl(6-((2-(1-(cyclopropylsulfonyl)-1H-pyrazol-4-yl)pyrimidin-4-yl)amino)-4-((tetrahydro-2H-pyran-4-yl)amino)pyridin-3-yl)methanone;

(36) Cyclopropyl(6-((2-(1-(cyclopropylsulfonyl)-1H-pyrazol-4-yl)pyrimidin-4-yl)amino)-4-(((3S,4R)-3,4-dihydroxycyclohexyl)amino)pyridin-3-yl)methanone;

(37) Cyclopropyl(6-((2-(1-(cyclopropylsulfonyl)-1H-pyrazol-4-yl)pyrimidin-4-yl)amino)-4-((1-(2-(dimethylamino)ethyl)piperidin-4-yl)amino)pyridin-3-yl)methanone;

(38) Cyclopropyl(6-((2-(1-(cyclopropylsulfonyl)-1H-pyrazol-4-yl)pyrimidin-4-yl)amino)-44(1-(oxetan-3-yl)piperidin-4-yl)amino)pyridin-3-yl)methanone;

(39) Cyclopropyl(6-((2-(1-(cyclopropylsulfonyl)-1H-pyrazol-4-yl)pyrimidin-4-yl)amino)-44(1-(2-fluoroethyl)piperidin-3-yl)amino)pyridin-3-yl)methanone;

(40) 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2-(tetrahydro-2H-pyran-4-yl)ethan-1-one;

(41) $N^2$-(2-(1-(Cyclopropylsulfonyl)-1H-pyrazol-4-yl)pyrimidin-4-yl)-5-fluoro-$N^4$-isopropylpyridine-2,4-diamine;

(42) N-(6-((2-(1-(Cyclopropylsulfonyl)-1H-pyrazol-4-yl)pyrimidin-4-yl)amino)-4-isopropoxypyridin-3-yl)cyclopropanecarboxamide;

(43) (4-((((1r,4r)-4-((1H-Imidazol-1-yl)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;

(44) (4-((((1r,4r)-4-((1H-Pyrazol-1-yl)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;

(45) 1-(6-((2-(1-(Cyclopropylsulfonyl)-1H-pyrazol-4-yl)pyrimidin-4-yl)amino)-4-(propylamino)pyridin-3-yl)ethan-1-one;

(46) 1-(6-((2-(1-(Cyclopropylsulfonyl)-1H-pyrazol-4-yl)pyrimidin-4-yl)amino)-4-((3-hydroxy-2-methylbutan-2-yl)amino)pyridin-3-yl)ethan-1-one;

(47) 1-(6-((2-(1-Cyclopropylsulfonylpyrazol-4-yl)pyrimidin-4-yl)amino)-44(3-(hydroxymethyl)cyclopentyl)amino)-3-pyridyl)ethanone;

(48) 1-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)-2,2-difluoroethan-1-one;

(49) 1-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)-2,2-difluoroethan-1-one;

(50) 1-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-2,2-difluoroethan-1-one;

(51) 1-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)-2,2-difluoroethan-1-one;

(52) Cyclopropyl(6-((2-(1-(cyclopropylsulfonyl)-1H-pyrazol-4-yl)pyrimidin-4-yl)amino)-4-((4-((2-hydroxyethyl)amino)cyclohexyl)amino)pyridin-3-yl)methanone;

(53) Cyclopropyl(6-((2-(1-(cyclopropylsulfonyl)-1H-pyrazol-4-yl)pyrimidin-4-yl)amino)-4-((4-((2-(dimethylamino)ethyl)amino)cyclohexyl)amino)pyridin-3-yl)methanone;

(54) Cyclopropyl(6-((2-(1-(cyclopropylsulfonyl)-1H-pyrazol-4-yl)pyrimidin-4-yl)amino)-4-((4-((4-methylpiperazin-1-yl)amino)cyclohexyl)amino)pyridin-3-yl)methanone;

(55) Cyclopropyl(6-((2-(1-(cyclopropylsulfonyl)-1H-pyrazol-4-yl)pyrimidin-4-yl)amino)-4-((4-((2-(3-fluoroazetidin-1-yl)ethyl)amino)cyclohexyl)amino)pyridin-3-yl)methanone;

(56) Cyclopropyl(6-((2-(1-(cyclopropylsulfonyl)-1H-pyrazol-4-yl)pyrimidin-4-yl)amino)-4-((4-((2-(piperidin-1-yl)ethyl)amino)cyclohexyl)amino)pyridin-3-yl)methanone;

(57) Cyclopropyl(6-((2-(1-(cyclopropylsulfonyl)-1H-pyrazol-4-yl)pyrimidin-4-yl)amino)-4-((4-((2-(4-(dimethylamino)piperidin-1-yl)ethyl)amino)cyclohexyl)amino)pyridin-3-yl)methanone;

(58) Cyclopropyl(6-((2-(1-(cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)methanone;

(59) (6-((2-(1H-Pyrazol-4-yl)pyrimidin-4-yl)amino)-4-((((1r,4r)-4-((dimethylamino)methyl)cyclohexyl)methyl)amino)pyridin-3-yl)(cyclopropyl)methanone;

(60) Cyclopropyl(6-((2-(1-cyclopropyl-1H-pyrazol-4-yl)pyrimidin-4-yl)amino)-4-((((1r,4r)-4-((dimethylamino)methyl)cyclohexyl)methyl)amino)pyridin-3-yl)methanone;

(61) Cyclopropyl(6-((2-(1-(cyclopropylmethyl)-1H-pyrazol-4-yl)pyrimidin-4-yl)amino)-4-((((1r,4r)-4-((dimethylamino)methyl)cyclohexyl)methyl)amino)pyridin-3-yl)methanone;

(62) Cyclopropyl(4-((((1r,4r)-4-((dimethylamino)methyl)cyclohexyl)methyl)amino)-6-((2-(1-(tetrahydrofuran-3-yl)-1H-pyrazol-4-yl)pyrimidin-4-yl)amino)pyridin-3-yl)methanone;

(63) 1-(6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)ethan-1-one;

(64) (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(4-fluorophenyl)methanone;

(65) 1-(6-((2-(1-(Cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)ethan-1-one;

(66) Cyclopropyl(6-((2-(1-(cyclopropylsulfonyl)-1H-pyrazol-4-yl)pyrimidin-4-yl)amino)-4-(((1r,4r)-4-((dimethylamino)methyl)cyclohexyl)methoxy)pyridin-3-yl)methanone;

(67) (4-((((1r,4r)-4-(Aminomethyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;

(68) N-(((1r,4r)-4-(((5-(Cyclopropanecarbonyl)-24(2-(1-(cyclopropylsulfonyl)-1H-pyrazol-4-yl)pyrimidin-4-yl)amino)pyridin-4-yl)amino)methyl)cyclohexyl)methyl)acetamide;

(69) Cyclopropyl(6-((2-(1-(cyclopropylsulfonyl)-1H-pyrazol-4-yl)pyrimidin-4-yl)amino)-4-((((1r,4r)-4-((isopropylamino)methyl)cyclohexyl)methyl)amino)pyridin-3-yl)methanone;

(70) (4-((((1r,4r)-4-((Cyclopentylamino)methyl)cyclohexyl)methyl)amino)-6-((2-(1-(cyclopropylsulfonyl)-1H-pyrazol-4-yl)pyrimidin-4-yl)amino)pyridin-3-yl)(cyclopropyl)methanone;

(71) Cyclopropyl(6-((2-(1-(cyclopropylsulfonyl)-1H-pyrazol-4-yl)pyrimidin-4-yl)amino)-4-((((1r,4r)-4-(((3-hydroxy-3-methylbutan-2-yl)amino)methyl)cyclohexyl)methyl)amino)pyridin-3-yl)methanone;

(72) N-(((1r,4r)-4-(((5-(Cyclopropanecarbonyl)-24(2-(1-(cyclopropylsulfonyl)-1H-pyrazol-4-yl)pyrimidin-4-yl)amino)pyridin-4-yl)amino)methyl)cyclohexyl)methyl)isobutyramide;

(73) Cyclopropyl(6-((2-(1-(cyclopropylsulfonyl)-1H-pyrazol-4-yl)pyrimidin-4-yl)amino)-4-((((1r,4r)-4-(((1,1-difluoropropan-2-yl)amino)methyl)cyclohexyl)methyl)amino)pyridin-3-yl)methanone;

(74) 6-((2-(1-(Cyclopropylsulfonyl)-1H-pyrazol-4-yl)pyrimidin-4-yl)amino)-N-(2-fluoroethyl)-4-(isopropylamino)nicotinamide;

(75) 6-((2-(1-(Cyclopropylsulfonyl)-1H-pyrazol-4-yl)pyrimidin-4-yl)amino)-N-(2-fluoroethyl)-4-(((1R,3S)-3-(hydroxymethyl)cyclopentyl)amino)nicotinamide;

(76) 6-((2-(1-(Cyclopropylsulfonyl)-1H-pyrazol-4-yl)pyrimidin-4-yl)amino)-N-(2-fluoroethyl)-4-(((1s,4s)-4-hydroxy-4-methylcyclohexyl)amino)nicotinamide;

(77) 6-((2-(1-(Cyclopropylsulfonyl)-1H-pyrazol-4-yl)pyrimidin-4-yl)amino)-N-(2-fluoroethyl)-4-(((1s,4s)-4-((2-fluoroethyl)amino)cyclohexyl)amino)nicotinamide;

(78) 6-((2-(1-(Cyclopropylsulfonyl)-1H-pyrazol-4-yl)pyrimidin-4-yl)amino)-N-(2,2-difluoroethyl)-4-(isopropylamino)nicotinamide;

(79) 6-((2-(1-(Cyclopropylsulfonyl)-1H-pyrazol-4-yl)pyrimidin-4-yl)amino)-N-(2,2-difluoroethyl)-4-(((1s,4s)-4-hydroxycyclohexyl)amino)nicotinamide;

(80) 6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)-N-((1r,4r)-4-hydroxycyclohexyl)nicotinamide;

(81) 6-((2-(1-(Cyclopropylsulfonyl)-1H-pyrazol-4-yl)pyrimidin-4-yl)amino)-N-(2,2-difluoroethyl)-4-((((1r,4r)-4-((dimethylamino)methyl)cyclohexyl)methyl)amino)nicotinamide;

(82) (6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)pyridin-3-yl)(3,3-difluoroazetidin-1-yl)methanone;

(83) 6-((2-(1-(Cyclopropylsulfonyl)-1H-pyrazol-4-yl)pyrimidin-4-yl)amino)-4-((((1r,4r)-4-((dimethylamino)methyl)cyclohexyl)methyl)amino)-N-(2-fluoroethyl)nicotinamide;

(84) $N^2$-(2-(1-(Cyclopropylsulfonyl)-1H-pyrazol-4-yl)pyrimidin-4-yl)-5-(3,4-dihydro-2H-pyran-6-yl)-$N^4$-isopropylpyridine-2,4-diamine;

(85) (1-(2-((2-(1-(Cyclopropylsulfonyl)-1H-pyrazol-4-yl)pyrimidin-4-yl)amino)-5-fluoropyridin-4-yl)-4-methylpiperidin-4-yl)methanol;

(86) Cyclopropyl(6-((2-(1-(cyclopropylsulfonyl)-1H-pyrazol-4-yl)pyrimidin-4-yl)amino)-4-(((1s,4s)-4-hydroxy-4-hydroxymethyl)cyclohexyl)amino)pyridin-3-yl)methanone;

(87) Cyclopropyl(6-((2-(1-(cyclopropylsulfonyl)-1H-pyrazol-4-yl)pyrimidin-4-yl)amino)-4-((4-fluoro-4-(hydroxymethyl)cyclohexyl)amino)pyridin-3-yl)methanone;

(88) Cyclopropyl(6-((2-(1-(cyclopropylsulfonyl)-1H-pyrazol-4-yl)pyrimidin-4-yl)amino)-4-((((1r,4r)-4-(methylamino)cyclohexyl)methyl)amino)pyridin-3-yl)methanone; and

(89) Cyclopropyl(6-((2-(1-(cyclopropylsulfonyl)-1H-pyrazol-4-yl)pyrimidin-4-yl)amino)-4-((((1r,4r)-4-((methylamino)methyl)cyclohexyl)methyl)amino)pyridin-3-yl)methanone.

25. A method of treating protein kinase-mediated disease in a subject in need thereof, comprising administering to said subject a therapeutically effective amount of a compound of claim 1 or 24, or a pharmaceutically acceptable salt thereof.

26. The method of claim 25, wherein the protein kinase-mediated disease is cancer or immune disease.

27. The method of claim 26, wherein the cancer is bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, thyroid cancer, prostate cancer, skin cancer or hematological tumors.

28. The method of claim 26, wherein the cancer is lung cancer.

29. The method of claim 26, wherein the cancer is non-small cell lung cancer.

30. A method of selectively inhibiting at least one mutant of EGFR in a patient, comprising administering to a patient a compound of claim 1 or 24, or a pharmaceutically acceptable salt thereof.

31. The method according to claim 30, wherein the at least one mutant is at least one single mutant selected from the group consisting of EGFR Del19 (Del E746-A750) and EGFR L858R.

32. The method according to claim 30, wherein the at least one mutant is at least one double mutant selected from the group consisting of EGFR Del19/T790M, EGFR Del19/C797S, EGFR Del19/C797X (X=G, N), EGFR Del19/L792X (X=F, H, P, R, V, Y), EGFR Del19/L718X (X=Q, V), EGFR L858R/T790M, EGFR L858R/C797S, EGFR L858R/C797X (X=G, N), EGFR L858R/L792X (X=F, H, P, R, V, Y) and EGFR L858R/L718X (X=Q, V).

33. The method according to claim 30, wherein the at least one mutant is at least one double mutant selected from the group consisting of EGFR Dell 9/C797S and EGFR L858R/C797S.

34. The method according to claim 30, wherein the at least one mutant is at least one triple mutant selected from the group consisting of EGFR Del19/T790M/C797S, EGFR Del19/T790M/C797X (X=G, N), EGFR Del19/T790M/L792X (X=F, H, P, R, V, Y), EGFR Del19/T790M/L718X (X=Q, V), EGFR L858R/T790M/C797S, EGFR L858R/T790M/C797X (X=G, N), EGFR L858R/T790M/L792X (X=F, H, P, R, V, Y), and EGFR L858R/T790M/L718X (X=Q, V).

35. The method according to claim 30, wherein the at least one mutant is at least one triple mutant selected from the group consisting of EGFR Dell 9/T790M/C797S and EGFR L858R/T790M/C797S.

36. A pharmaceutical composition for treating a protein kinase-mediated disease, comprising a compound of claim 1 or 24, or a pharmaceutically acceptable salt thereof as active ingredients.

37. The composition of claim 36, the protein kinase-mediated disease is cancer or immune disease.

38. The composition of claim 37, wherein the cancer is bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, thyroid cancer, prostate cancer, skin cancer or hematological tumors.

39. A pharmaceutical composition for inhibiting at least one mutant of EGFR selectively as compared to wild type EGFR, comprising a compound of claim 1 or 24, or a pharmaceutically acceptable salt thereof as active ingredients.

* * * * *

UNITED STATES PATENT AND TRADEMARK OFFICE
CERTIFICATE OF CORRECTION

PATENT NO. : 11,945,798 B2
APPLICATION NO. : 17/822438
DATED : April 2, 2024
INVENTOR(S) : Lee et al.

Page 1 of 1

It is certified that error appears in the above-identified patent and that said Letters Patent is hereby corrected as shown below:

In the Specification

Column 11, Line 3:
Please delete "N and 0." and replace with -- N and O. --

In the Claims

Column 78, Claim 14, Line 28:
Please delete "N and 0" and replace with -- N and O --

Column 81, Claim 24, Lines 52-54:
Please delete "-44(" and replace with -- -4-(( --

Column 81, Claim 24, Lines 55-57:
Please delete "-44(" and replace with -- -4-(( --

Column 82, Claim 24, Lines 16-18:
Please delete "-44(" and replace with -- -4-(( --

Column 83, Claim 24, Lines 33-36:
Please delete "-24(" and replace with -- -2-(( --

Column 83, Claim 24, Lines 50-53:
Please delete "-24(" and replace with -- -2-(( --

Column 85, Claim 33, Line 19:
Please delete "EGFR Dell 9/C797S" and replace with -- EGFR Del19/C797S --

Column 86, Claim 35, Line 6:
Please delete "EGFR Dell 9/T790M/C797S" and replace with -- EGFR Del19/T790M/C797S --

Signed and Sealed this
Eighteenth Day of June, 2024

Katherine Kelly Vidal
*Director of the United States Patent and Trademark Office*